United States Patent
Wang et al.

(10) Patent No.: US 11,802,113 B2
(45) Date of Patent: Oct. 31, 2023

(54) SUBSTITUTED PYRAZOLE COMPOUNDS, COMPOSITIONS CONTAINING SAME, AND USE THEREOF

(71) Applicant: Shenzhen TargetRx, Inc., Shenzhen (CN)

(72) Inventors: Yihan Wang, Shenzhen (CN); Xingye Ren, Shenzhen (CN)

(73) Assignee: Shenzhen TargetRx, Inc., Shenzhen (CN)

( * ) Notice: Subject to any disclaimer, the term of this patent is extended or adjusted under 35 U.S.C. 154(b) by 209 days.

(21) Appl. No.: 17/439,299

(22) PCT Filed: Feb. 26, 2020

(86) PCT No.: PCT/CN2020/076756
§ 371 (c)(1),
(2) Date: Sep. 14, 2021

(87) PCT Pub. No.: WO2020/173457
PCT Pub. Date: Sep. 3, 2020

(65) Prior Publication Data
US 2022/0251046 A1 Aug. 11, 2022

(30) Foreign Application Priority Data
Feb. 27, 2019 (CN) .......................... 201910145179.2

(51) Int. Cl.
*C07D 231/14* (2006.01)
*C07D 231/12* (2006.01)

(52) U.S. Cl.
CPC ......... *C07D 231/14* (2013.01); *C07D 231/12* (2013.01); *C07B 2200/05* (2013.01)

(58) Field of Classification Search
CPC ............................ C07D 231/12; C07D 231/14
See application file for complete search history.

(56) References Cited

U.S. PATENT DOCUMENTS 8,975,254 B2 * 3/2015 Wohlfahrt ............ C07D 498/04
548/200
10,118,933 B2 11/2018 Wohlfahrt et al.

FOREIGN PATENT DOCUMENTS

CN 102596910 A 7/2012
JP 2013-508447 A 3/2013

OTHER PUBLICATIONS

Cancer and Metastasis Reviews (1998), 17(1), 91-106.*
Science (1999), vol. 286, 531-537.*
Cancer [online], [retrieved on Jul. 6, 2007]. Retrieved from the internet, URLhttp://www.nlm.nih.gov/medlineplus/cancer.html>.*
Office Action in 2021-550056 dated Oct. 4, 2022, 3 pages.
Kaur, et al. "Deuteration as a tool for optimization of metabolic stability and toxicity of drugs." Glob. J. Pharmaceu. Sci 1 (2017): 555566.
Harbeson, et al. "Deuterium medicinal chemistry: a new approach to drug discovery and development." MedChem News 24, No. 2 (2014): 8-22.
International Search Report in PCT/US2020/076756, dated Jun. 30, 2020, 3 pages.

* cited by examiner

*Primary Examiner* — Shawquia Jackson
(74) *Attorney, Agent, or Firm* — Kilpatrick Townsend & Stockton LLP

(57) ABSTRACT

The present invention provides substituted pyrazole compounds, compositions containing same, and use thereof. The substituted pyrazole compounds comprise a compound represented by formula (I) or a tautomer, stereoisomer, prodrug, crystalline form, pharmaceutically acceptable salt, hydrate, or solvate thereof. The compound represented by formula (I) can serve as a tissue selective androgen receptor modulator (SARM), particularly serving as a drug for treating prostate cancer and other AR-dependent conditions and diseases in which AR antagonism is desired.

10 Claims, No Drawings

SUBSTITUTED PYRAZOLE COMPOUNDS, COMPOSITIONS CONTAINING SAME, AND USE THEREOF

TECHNICAL FIELD

The present invention belongs to the field of pharmaceutical technology, and in particular relates to a substituted pyrazole compound and a composition containing the compound and its use. More specifically, the present invention relates to certain deuterium-substituted N-(1-(3-(3-chloro-4-cyanophenyl)-1H-pyrazol-1-yl)-propan-2-yl)-5-(1-hydroxyethyl)-1H-pyrazole-3-carboxamide compounds and their tautomers, stereoisomers, prodrugs, crystal forms, pharmaceutically acceptable salts, hydrates or solvates. These deuterium-substituted compounds and their compositions can be used as tissue selective androgen receptor modulators (SARM), especially as medicaments for the treatment of prostate cancer and other AR-dependent conditions and diseases in which AR antagonism is desired.

BACKGROUND

Androgen receptor (AR) belongs to the nuclear receptor superfamily. AR contains 918 amino acid residues, thus constituting 3 important structural domains, namely DNA binding domain (DBD), ligand binding domain (LBD) and N-terminal domain (NTD).

Androgen that acts through AR is necessary for the initiation and progression of prostate cancer. Therefore, the treatment of advanced prostate cancer includes androgen deprivation therapy, such as surgical removal of the testicles, or hormone regulation using Gonadotropin-releasing hormone (GnRH) agonists, antiandrogens or both. Although the treatment initially leads to the regression of the disease, in the end all patients will develop into an advanced stage of castration resistance that is difficult to control with current treatments.

Castration-resistant prostate cancer (CRPC) still relies on the androgen receptor (AR) signaling axis for continued growth. The main reason for the recurrence of CRPC is the reactivation of AR through the following alternative mechanisms: 1) intracrine androgen synthesis; 2) AR splice variant (AR-SV), for example, without LBD; 3) AR-LBD mutations with potential to resist AR antagonists (i.e., mutants that are not sensitive to inhibition by AR antagonists, and in some cases, AR antagonists act as AR agonists that carry these LBD mutations); and 4) expansion of AR genes in tumors. The first generation of antiandrogens such as bicalutamide showed agonist activity in cells genetically engineered to express high AR levels. In vitro and in vivo, increased AR expression appears to make prostate cancer cell lines resistant to antiandrogen therapy. In order to overcome the problem of drug resistance, second-generation antiandrogens that can maintain antagonism in cells expressing excessive AR may be used to treat CRPC.

Darolutamide (the chemical name is N—((S)-1-(3-(3-chloro-4-cyanophenyl)-1H-pyrazol-1-yl)-prop-2-yl)-5-(1-hydroxyethyl)-1H-pyrazole-3-carboxamide, having the following structural formula) is a non-steroidal androgen receptor antagonist jointly developed by Bayer and Orion, Finland, has a high affinity for AR receptors, has a strong antagonistic effect, and can inhibit the receptor function and growth of prostate cancer cells. The drug has been granted fast-track status for the treatment of non-metastatic castration-resistant prostate cancer (nmCRPC) patients by the FDA of US. The Phase III clinical trial study named ARAMIS showed that compared with placebo, the use of Darolutamide in the male nmCRPC patient population significantly prolonged the patients' metastasis-free survival and the chance of causing treatment-related adverse events in the asymptomatic patient population is low.

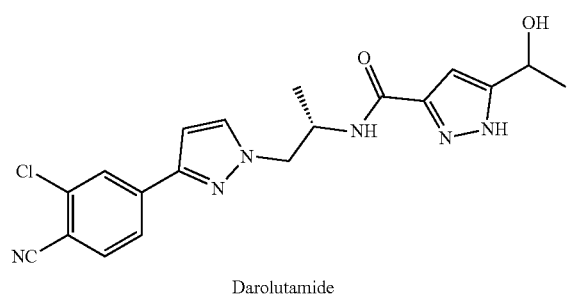 [SMILES: CC(O)c1cc(C(=O)N[C@@H](C)Cn2ccc(-c3ccc(C#N)c(Cl)c3)n2)n[nH]1]

Darolutamide

It is known that poor absorption, distribution, metabolism, and/or excretion (ADME) properties are the main reason for the failure of many drug candidates in clinical trials. Many drugs currently on the market also have limited application fields due to their poor ADME properties. The rapid metabolism of agents will lead to many agents that could have been effective in treating diseases but are hard to be real drugs because of too rapid metabolism and removal from the body. Although frequent or high-dose administration may solve the problem of rapid drug clearance, this method will bring about problems such as poor patient compliance, side effects caused by high-dose medication, and increased treatment costs. In addition, rapidly metabolizing drugs may also expose patients to undesirable toxic or reactive metabolites.

It is still challenging work to find new and effective AR antagonists that have good oral bioavailability, and can be made into medicaments. Therefore, there is still a need in the art to develop compounds that are suitable for use as AR antagonists and have selective inhibitory activity and/or better pharmacodynamics/pharmacokinetics. The present invention provides such compounds.

SUMMARY OF THE INVENTION

In view of the above technical problems, the present invention discloses a novel deuterium-substituted pyrazole compound as an effective AR antagonist, which exhibits significantly high affinity and strong antagonistic activity for androgen receptor. In addition, in cells overexpressing AR ("AR overexpressing cells"), the compounds of the present invention have high to complete AR antagonism, while showing only minimal agonism. The compounds of the present invention also effectively inhibit the proliferation of prostate cancer cell lines. In addition, the compounds of the present invention also have lower side effects, better metabolic stability and/or pharmacokinetic properties.

In this regard, the present invention adopts the following technical solutions:

In the first aspect of the present invention, a compound of formula (I) is provided:

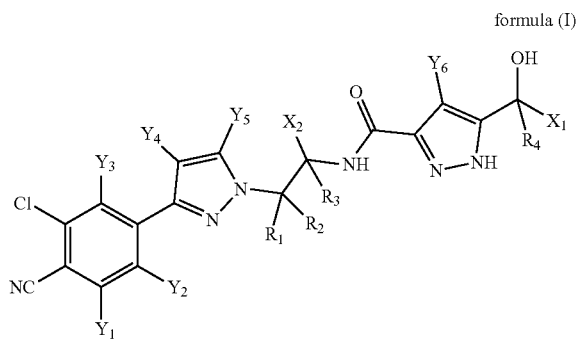

formula (I)

wherein
$Y_1$, $Y_2$, $Y_3$, $Y_4$, $Y_5$ and $Y_6$ are each independently selected from hydrogen, deuterium or halogen;
$R_1$, $R_2$, $R_3$ and $R_4$ are each independently selected from hydrogen or deuterium;
$X_1$ and $X_2$ are each independently selected from $CH_3$, $CD_3$, $CHD_2$ or $CH_2D$;
provided that the compound comprises at least one deuterium atom;
or a tautomer, stereoisomer, prodrug, crystal form, pharmaceutically acceptable salt, hydrate or solvate thereof.

In another aspect, the invention provides a pharmaceutical composition comprising a compound of the invention and a pharmaceutically acceptable excipient. In a specific embodiment, the compound of the present invention is provided in the pharmaceutical composition in an effective amount. In a specific embodiment, the compound of the invention is provided in a therapeutically effective amount. In a specific embodiment, the compound of the invention is provided in a prophylactically effective amount. In a specific embodiment, the pharmaceutical composition further comprises an additional therapeutic agent.

In another aspect, the present invention provides a method for preparing the pharmaceutical composition as described above, comprising the following step: mixing a pharmaceutically acceptable excipient with a compound of the present invention or a tautomer, stereoisomer, prodrug, crystal form, pharmaceutically acceptable salt, hydrate or solvate thereof to form a pharmaceutical composition.

In another aspect, the present invention provides use of a compound of the present invention or a tautomer, stereoisomer, prodrug, crystal form, pharmaceutically acceptable salt, hydrate or solvate thereof, or a pharmaceutical composition mentioned above, in the manufacture of medicament for treating and/or preventing androgen receptor dependent diseases.

In another aspect, the present invention further provides a method of treating and/or preventing androgen receptor (AR) dependent diseases, comprising administering a therapeutically effective amount of a compound of the present invention to a subject in need thereof. For example, AR-dependent diseases are cancers, especially AR-dependent cancers such as prostate cancer and benign prostatic hyperplasia. In a specific embodiment, the AR-dependent disease is castration resistant prostate cancer (CRPC). In specific embodiments, the compound is administered orally, subcutaneously, intravenously, or intramuscularly. In a specific embodiment, the compound is administered chronically.

Definition

Herein, unless otherwise specified, "deuterated" means that one or more hydrogen atoms in a compound or group are replaced by deuterium; and may be mono-, di-, multi-, or fully-substituted. The terms "mono- or multi-deuterated" and "substituted by one or more deuterium" are used interchangeably.

Herein, unless otherwise specified, "non-deuterated compound" refers to a compound that contains a proportion of deuterium atoms not higher than the content of natural deuterium isotope (0.015%).

As used herein, the term "subject" includes, but is not limited to: humans (i.e., men or women of any age group, for example, pediatric subjects (e.g., infants, children, adolescents) or adult subjects (e.g., young adults, middle-aged adults or older adults)) and/or non-human animals, for example, mammals, for example, primates (for example, cynomolgus monkeys and rhesus monkeys), cattle, pigs, horses, sheep, goats, rodents, cats and/or dogs. In some embodiments, the subject is a human. In other embodiments, the subject is a non-human animal.

"Disease", "disorder" and "condition" are used interchangeably herein.

Unless otherwise specified, the term "treatment" as used herein includes the effect that occurs when a subject suffers from a specific disease, disorder, or condition, and reduces the severity of the disease, disorder, or condition, or delays or slows the development of the disease, disorder, or condition ("therapeutic treatment"), and also includes the effect that occurs before the subject starts suffering from a specific disease, disorder or condition ("preventive treatment").

Generally, the "effective amount" of a compound refers to an amount sufficient to cause a desired biological response. As understood by those of ordinary skill in the art, the effective amount of the compound of the present invention may vary according to the following factors: for example, the biological objectives, the pharmacokinetics of the compound, the disease to be treated, the mode of administration, and the age, health conditions and symptoms of the subject. The effective amount includes therapeutically and prophylactically effective amounts.

Unless otherwise specified, the "therapeutically effective amount" of the compound used herein is an amount sufficient to provide therapeutic benefit during the treatment of a disease, disorder, or condition, or delay or minimize one or more symptoms related to the disease, disorder, or condition. The therapeutically effective amount of a compound refers to the amount of a therapeutic agent used alone or in combination with other therapies, which provides therapeutic benefits in the process of treating a disease, disorder, or condition. The term "therapeutically effective amount" can include an amount that improves overall treatment, reduces or avoids the symptoms or causes of a disease or disorder, or enhances the therapeutic efficacy of other therapeutic agents.

Unless otherwise specified, the "prophylactically effective amount" of the compound used herein is an amount sufficient to prevent a disease, disorder, or condition, prevent one or more symptoms related to a disease, disorder, or condition, or prevent recurrence of a disease, disorder, or condition. The prophylactically effective amount of a compound refers to the amount of a therapeutic agent used alone or in combination with other agents, which provides a preventive benefit in the process of preventing a disease, disorder or condition. The term "prophylactically effective amount" may include an amount that improves overall prevention, or an amount that enhances the preventive efficacy of other preventive agents.

"Combination" and related terms refer to the simultaneous or sequential administration of the therapeutic agents of the present invention. For example, the compound of the present invention may be administered simultaneously or sequentially with another therapeutic agent in separate unit dosage forms, or administered simultaneously with another therapeutic agent in a single unit dosage form.

Specific Modes for Carrying Out the Invention

Compound

Herein, "the compound of the present invention" refers to a compound of the following formula (I), formula (I-1), formula (I-2), formula (I-1a), formula (I-1b), formula (I-2a), formula (I-2b), formula (II), formula (II-1), formula (II-2), formula (II-1a), formula (II-1b), formula (II-2a) and formula (II-2b), or a tautomer, stereoisomer, prodrug, crystal form, pharmaceutically acceptable salt, hydrate or solvate thereof.

In one embodiment, the invention relates to a compound of formula (I):

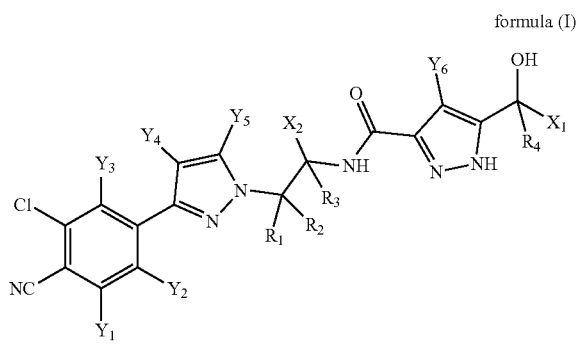

formula (I)

wherein $Y_1$, $Y_2$, $Y_3$, $Y_4$, $Y_5$ and $Y_6$ are each independently selected from hydrogen, deuterium or halogen;

$R_1$, $R_2$, $R_3$ and $R_4$ are each independently selected from hydrogen or deuterium;

$X_1$ and $X_2$ are each independently selected from $CH_3$, $CD_3$, $CHD_2$ or $CH_2D$;

provided that the compound comprises at least one deuterium atom;

or a tautomer, stereoisomer, prodrug, crystal form, pharmaceutically acceptable salt, hydrate or solvate thereof.

In a specific embodiment, the deuterium isotope content in the deuterated position is at least greater than the natural deuterium isotope content, 0.015%, preferably greater than 30%, more preferably greater than 50%, more preferably greater than 75%, more preferably greater than 95%, and more preferably greater than 99%.

Specifically, in the present invention, the deuterium isotope content of each deuterated position of $Y_1$, $Y_2$, $Y_3$, $Y_4$, $Y_5$, $Y_6$, $R_1$, $R_2$, $R_3$, $R_4$, $X_1$, and $X_2$ is at least greater than the natural deuterium isotope content, 0.015%, preferably greater than 1%, more preferably greater than 5%, more preferably greater than 10%, more preferably greater than 15%, more preferably greater than 20%, more preferably greater than 25%, more preferably greater than 30%, more preferably greater than 35%, more preferably greater than 40%, more preferably greater than 45%, more preferably greater than 50%, more preferably greater than 55%, more preferably greater than 60%, more preferably greater than 65%, more preferably greater than 70%, more preferably greater than 75%, more preferably greater than 80%, more preferably greater than 85%, more preferably greater than 90%, more preferably greater than 95%, and more preferably greater than 99%.

In another specific embodiment, the compound of the present invention comprises at least one deuterium atom, more preferably two deuterium atoms, more preferably three deuterium atoms, more preferably four deuterium atoms, more preferably five deuterium atoms, more preferably six deuterium atoms, more preferably seven deuterium atoms, more preferably eight deuterium atoms, more preferably nine deuterium atoms, more preferably ten deuterium atoms, more preferably eleven deuterium atoms, more preferably twelve deuterium atoms, more preferably thirteen deuterium atoms, more preferably fourteen deuterium atoms, more preferably fifteen deuterium atoms, and more preferably sixteen deuterium atoms.

In another specific embodiment, "$Y_1$, $Y_2$, $Y_3$, $Y_4$, $Y_5$, and $Y_6$ are each independently selected from hydrogen, deuterium or halogen" includes the embodiment where $Y_1$ is selected from hydrogen, deuterium or halogen, the embodiment where $Y_2$ is selected from hydrogen, deuterium or halogen, the embodiment where $Y_3$ is selected from hydrogen, deuterium or halogen, and so on, until the embodiment where $Y_6$ is selected from hydrogen, deuterium or halogen. More specifically, it includes the embodiment where $Y_1$ is hydrogen, $Y_1$ is deuterium or $Y_1$ is halogen (F, Cl, Br or I), the embodiment where $Y_2$ is hydrogen, $Y_2$ is deuterium or $Y_2$ is halogen (F, Cl, Br or I), the embodiment where $Y_3$ is hydrogen, $Y_3$ is deuterium or $Y_3$ is halogen (F, Cl, Br or I), and so on, until the embodiment where $Y_6$ is hydrogen, $Y_6$ is deuterium or $Y_6$ is halogen (F, Cl, Br or I).

In another specific embodiment, "$R_1$, $R_2$, $R_3$, and $R_4$ are each independently selected from hydrogen or deuterium" includes the embodiment where $R_1$ is selected from hydrogen or deuterium, the embodiment where $R_2$ is selected from hydrogen or deuterium, the embodiment where $R_3$ is selected from hydrogen or deuterium, and the embodiment where $R_4$ is selected from hydrogen or deuterium. More specifically, it includes the embodiment where $R_1$ is hydrogen or $R_1$ is deuterium, the embodiment where $R_2$ is hydrogen or $R_2$ is deuterium, the embodiment where $R_3$ is hydrogen or $R_3$ is deuterium, and the embodiment where $R_4$ is hydrogen or $R_4$ is deuterium.

In another specific embodiment, "$X_1$ and $X_2$ are each independently selected from $CH_3$, $CD_3$, $CHD_2$, or $CH_2D$" includes the embodiment where $X_1$ is selected from $CH_3$, $CD_3$, $CHD_2$, or $CH_2D$, and the embodiment where $X_2$ is selected from $CH_3$, $CD_3$, $CHD_2$, or $CH_2D$. More specifically, it includes the embodiment where $X_1$ is $CH_3$, $X_1$ is $CD_3$, $X_1$ is $CHD_2$ or $X_1$ is $CH_2D$ and the embodiment where $X_2$ is $CH_3$, $X_2$ is $CD_3$, $X_2$ is $CHD_2$ or $X_2$ is $CH_2D$.

In another embodiment, the present invention relates to a compound of formula (I-1):

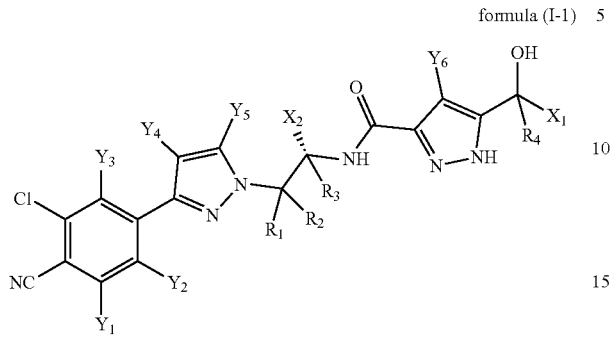

formula (I-1)

wherein $Y_1, Y_2, Y_3, Y_4, Y_5, Y_6, R_1, R_2, R_3, R_4, X_1$ and $X_2$ are as defined above;
or a tautomer, stereoisomer, prodrug, crystal form, pharmaceutically acceptable salt, hydrate or solvate thereof.

In another embodiment, the present invention relates to a compound of formula (I-1a):

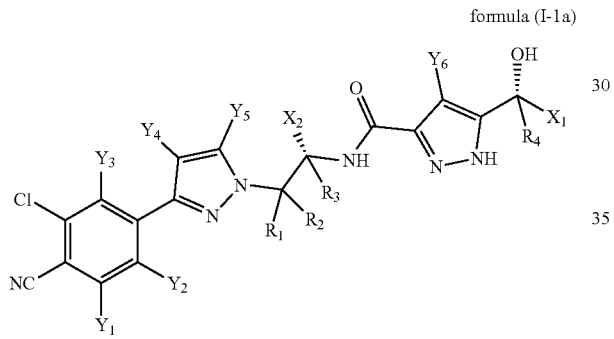

formula (I-1a)

wherein $Y_1, Y_2, Y_3, Y_4, Y_5, Y_6, R_1, R_2, R_3, R_4, X_1$ and $X_2$ are as defined above;
or a tautomer, stereoisomer, prodrug, crystal form, pharmaceutically acceptable salt, hydrate or solvate thereof.

In another embodiment, the present invention relates to a compound of formula (I-1b):

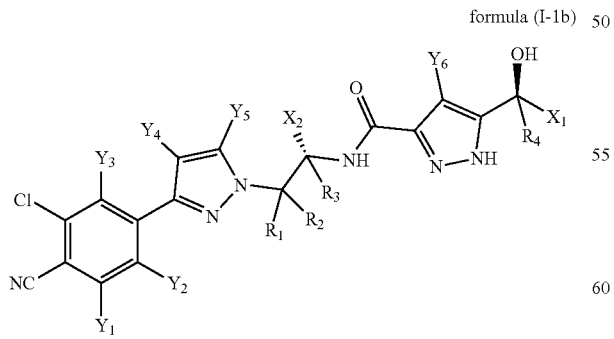

formula (I-1b)

wherein $Y_1, Y_2, Y_3, Y_4, Y_5, Y_6, R_1, R_2, R_3, R_4, X_1$ and $X_2$ are as defined above;
or a tautomer, stereoisomer, prodrug, crystal form, pharmaceutically acceptable salt, hydrate or solvate thereof.

In another embodiment, the present invention relates to a compound of formula (I-2):

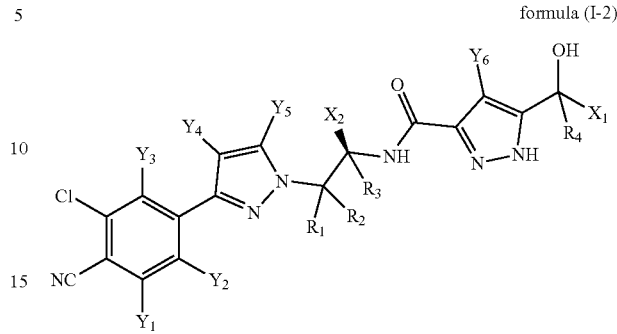

formula (I-2)

wherein $Y_1, Y_2, Y_3, Y_4, Y_5, Y_6, R_1, R_2, R_3, R_4, X_1$ and $X_2$ are as defined above;
or a tautomer, stereoisomer, prodrug, crystal form, pharmaceutically acceptable salt, hydrate or solvate thereof.

In another embodiment, the present invention relates to a compound of formula (I-2a):

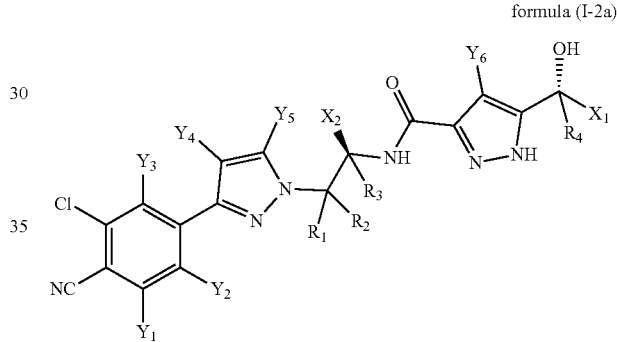

formula (I-2a)

wherein $Y_1, Y_2, Y_3, Y_4, Y_5, Y_6, R_1, R_2, R_3, R_4, X_1$ and $X_2$ are as defined above;
or a tautomer, stereoisomer, prodrug, crystal form, pharmaceutically acceptable salt, hydrate or solvate thereof.

In another embodiment, the present invention relates to a compound of formula (I-2b):

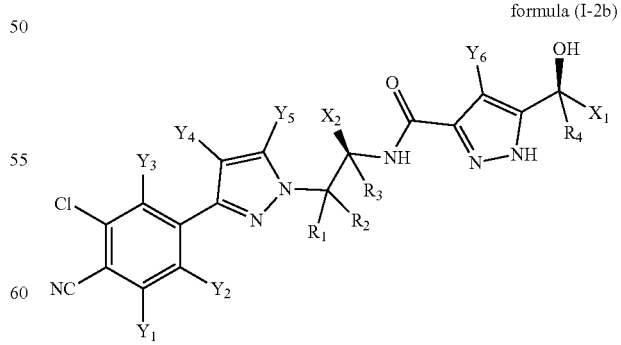

formula (I-2b)

wherein $Y_1, Y_2, Y_3, Y_4, Y_5, Y_6, R_1, R_2, R_3, R_4, X_1$ and $X_2$ are as defined above;
or a tautomer, stereoisomer, prodrug, crystal form, pharmaceutically acceptable salt, hydrate or solvate thereof.

In some embodiments of formula (I), formula (I-1), formula (I-2), formula (I-1a), formula (I-1b), formula (I-2a) and formula (I-2b), preferably, the present invention relates to the above-mentioned compound, or a tautomer, stereoisomer, prodrug, crystal form, pharmaceutically acceptable salt, hydrate or solvate thereof, wherein $R_3$ is hydrogen, $R_1$, $R_2$ and $R_4$ are each independently selected from hydrogen or deuterium, $X_1$ and $X_2$ are each independently selected from $CH_3$, $CD_3$, $CHD_2$ or $CH_2D$, and $Y_1$, $Y_2$, $Y_3$, $Y_4$, $Y_5$ and $Y_6$ are each independently selected from hydrogen or deuterium, provided that the compound comprises at least one deuterium atom.

In some embodiments of formula (I), formula (I-1), formula (I-2), formula (I-1a), formula (I-1b), formula (I-2a) and formula (I-2b), preferably, the present invention relates to the above-mentioned compound, or a tautomer, stereoisomer, prodrug, crystal form, pharmaceutically acceptable salt, hydrate or solvate thereof, wherein $R_1$ and $R_2$ are hydrogen, $R_3$ and $R_4$ are each independently selected from hydrogen or deuterium, $X_1$ and $X_2$ are each independently selected from $CH_3$, $CD_3$, $CHD_2$ or $CH_2D$, and $Y_1$, $Y_2$, $Y_3$, $Y_4$, $Y_5$ and $Y_6$ are each independently selected from hydrogen or deuterium, provided that the compound comprises at least one deuterium atom.

In some embodiments of formula (I), formula (I-1), formula (I-2), formula (I-1a), formula (I-1b), formula (I-2a) and formula (I-2b), preferably, the present invention relates to the above-mentioned compound, or a tautomer, stereoisomer, prodrug, crystal form, pharmaceutically acceptable salt, hydrate or solvate thereof, wherein $R_1$-$R_3$ are hydrogen, $R_4$ is selected from hydrogen or deuterium, $X_1$ and $X_2$ are each independently selected from $CH_3$, $CD_3$, $CHD_2$ or $CH_2D$, and $Y_1$, $Y_2$, $Y_3$, $Y_4$, $Y_5$, and $Y_6$ are each independently selected from hydrogen or deuterium, provided that the compound comprises at least one deuterium atom.

In some embodiments of formula (I), formula (I-1), formula (I-2), formula (I-1a), formula (I-1b), formula (I-2a) and formula (I-2b), preferably, the present invention relates to the above-mentioned compound, or a tautomer, stereoisomer, prodrug, crystal form, pharmaceutically acceptable salt, hydrate or solvate thereof, wherein $X_2$ is $CH_3$, $R_1$-$R_4$ are each independently selected from hydrogen or deuterium, $X_1$ is selected from $CH_3$, $CD_3$, $CHD_2$ or $CH_2D$, and $Y_1$, $Y_2$, $Y_3$, $Y_4$, $Y_5$ and $Y_6$ are each independently selected from hydrogen or deuterium, provided that the compound comprises at least one deuterium atom.

In some embodiments of formula (I), formula (I-1), formula (I-2), formula (I-1a), formula (I-1b), formula (I-2a) and formula (I-2b), preferably, the present invention relates to the above-mentioned compound, or a tautomer, stereoisomer, prodrug, crystal form, pharmaceutically acceptable salt, hydrate or solvate thereof, wherein $X_2$ is $CH_3$, $R_3$ is hydrogen, $R_1$, $R_2$ and $R_4$ are each independently selected from hydrogen or deuterium, $X_1$ is selected from $CH_3$, $CD_3$, $CHD_2$, or $CH_2D$, and $Y_1$, $Y_2$, $Y_3$, $Y_4$, $Y_5$ and $Y_6$ are each independently selected from hydrogen or deuterium, provided that the compound comprises at least one deuterium atom.

In some embodiments of formula (I), formula (I-1), formula (I-2), formula (I-1a), formula (I-1b), formula (I-2a) and formula (I-2b), preferably, the present invention relates to the above-mentioned compound, or a tautomer, stereoisomer, prodrug, crystal form, pharmaceutically acceptable salt, hydrate or solvate thereof, wherein $X_2$ is $CH_3$, $R_1$ and $R_2$ are hydrogen, $R_3$ and $R_4$ are each independently selected from hydrogen or deuterium, $X_1$ is selected from $CH_3$, $CD_3$, $CHD_2$ or $CH_2D$, and $Y_1$, $Y_2$, $Y_3$, $Y_4$, $Y_5$, and $Y_6$ are each independently selected from hydrogen or deuterium, provided that the compound comprises at least one deuterium atom.

In some embodiments of formula (I), formula (I-1), formula (I-2), formula (I-1a), formula (I-1b), formula (I-2a) and formula (I-2b), preferably, the present invention relates to the above-mentioned compound, or a tautomer, stereoisomer, prodrug, crystal form, pharmaceutically acceptable salt, hydrate or solvate thereof, wherein $X_2$ is $CH_3$, $R_1$-$R_3$ are hydrogen, $R_4$ is selected from hydrogen or deuterium, $X_1$ is selected from $CH_3$, $CD_3$, $CHD_2$ or $CH_2D$, and $Y_1$, $Y_2$, $Y_3$, $Y_4$, $Y_5$ and $Y_6$ are each independently selected from hydrogen or deuterium, provided that the compound comprises at least one deuterium atom.

In some embodiments of formula (I), formula (I-1), formula (I-2), formula (I-1a), formula (I-1b), formula (I-2a) and formula (I-2b), preferably, the present invention relates to the above-mentioned compound, or a tautomer, stereoisomer, prodrug, crystal form, pharmaceutically acceptable salt, hydrate or solvate thereof, wherein $R_4$ is hydrogen, $R_1$-$R_3$ are each independently selected from hydrogen or deuterium, $X_1$ and $X_2$ are each independently selected from $CH_3$, $CD_3$, $CHD_2$ or $CH_2D$, and $Y_1$, $Y_2$, $Y_3$, $Y_4$, $Y_5$ and $Y_6$ are each independently selected from hydrogen or deuterium, provided that the compound comprises at least one deuterium atom.

In some embodiments of formula (I), formula (I-1), formula (I-2), formula (I-1a), formula (I-1b), formula (I-2a) and formula (I-2b), preferably, the present invention relates to the above-mentioned compound, or a tautomer, stereoisomer, prodrug, crystal form, pharmaceutically acceptable salt, hydrate or solvate thereof, wherein $R_3$ and $R_4$ are hydrogen, $R_1$ and $R_2$ are each independently selected from hydrogen or deuterium, $X_1$ and $X_2$ are each independently selected from $CH_3$, $CD_3$, $CHD_2$ or $CH_2D$, and $Y_1$, $Y_2$, $Y_3$, $Y_4$, $Y_5$ and $Y_6$ are each independently selected from hydrogen or deuterium, provided that the compound comprises at least one deuterium atom.

In some embodiments of formula (I), formula (I-1), formula (I-2), formula (I-1a), formula (I-1b), formula (I-2a) and formula (I-2b), preferably, the present invention relates to the above-mentioned compound, or a tautomer, stereoisomer, prodrug, crystal form, pharmaceutically acceptable salt, hydrate or solvate thereof, wherein $R_1$, $R_2$ and $R_4$ is hydrogen, $R_3$ is selected from hydrogen or deuterium, $X_1$ and $X_2$ are each independently selected from $CH_3$, $CD_3$, $CHD_2$ or $CH_2D$, and $Y_1$, $Y_2$, $Y_3$, $Y_4$, $Y_5$ and $Y_6$ are each independently selected from hydrogen or deuterium, provided that the compound comprises at least one deuterium atom.

In some embodiments of formula (I), formula (I-1), formula (I-2), formula (I-1a), formula (I-1b), formula (I-2a) and formula (I-2b), preferably, the present invention relates to the above-mentioned compound, or a tautomer, stereoisomer, prodrug, crystal form, pharmaceutically acceptable salt, hydrate or solvate thereof, wherein $R_1$-$R_4$ are hydrogen, $X_1$ and $X_2$ are each independently selected from $CH_3$, $CD_3$, $CHD_2$, or $CH_2D$, and $Y_1$, $Y_2$, $Y_3$, $Y_4$, $Y_5$, and $Y_6$ are each independently selected from hydrogen or deuterium, provided that the compound comprises at least one deuterium atom.

In some embodiments of formula (I), formula (I-1), formula (I-2), formula (I-1a), formula (I-1b), formula (I-2a) and formula (I-2b), preferably, the present invention relates to the above-mentioned compound, or a tautomer, stereoisomer, prodrug, crystal form, pharmaceutically acceptable salt, hydrate or solvate thereof, wherein $R_4$ is hydrogen, $X_2$ is $CH_3$, $R_1$-$R_3$ are each independently selected from hydrogen or deuterium, $X_1$ is selected from $CH_3$, $CD_3$, $CHD_2$ or $CH_2D$, and $Y_1$, $Y_2$, $Y_3$, $Y_4$, $Y_5$ and $Y_6$ are each independently selected from hydrogen or deuterium, provided that the compound comprises at least one deuterium atom.

In some embodiments of formula (I), formula (I-1), formula (I-2), formula (I-1a), formula (I-1b), formula (I-2a) and formula (I-2b), preferably, the present invention relates to the above-mentioned compound, or a tautomer, stereoisomer, prodrug, crystal form, pharmaceutically acceptable salt, hydrate or solvate thereof, wherein $R_3$ and $R_4$ are hydrogen, $X_2$ is $CH_3$, $R_1$ and $R_2$ are each independently selected from hydrogen or deuterium, $X_1$ is selected from $CH_3$, $CD_3$, $CHD_2$ or $CH_2D$, and $Y_1$, $Y_2$, $Y_3$, $Y_4$, $Y_5$ and $Y_6$ are each independently selected from hydrogen or deuterium, provided that the compound comprises at least one deuterium atom.

In some embodiments of formula (I), formula (I-1), formula (I-2), formula (I-1a), formula (I-1b), formula (I-2a) and formula (I-2b), preferably, the present invention relates to the above-mentioned compound, or a tautomer, stereoisomer, prodrug, crystal form, pharmaceutically acceptable salt, hydrate or solvate thereof, wherein $R_1$, $R_2$ and $R_4$ are hydrogen, $X_2$ is $CH_3$, $R_3$ is selected from hydrogen or deuterium, $X_1$ is selected from $CH_3$, $CD_3$, $CHD_2$ or $CH_2D$, and $Y_1$, $Y_2$, $Y_3$, $Y_4$, $Y_5$ and $Y_6$ are each independently selected from hydrogen or deuterium, provided that the compound comprises at least one deuterium atom.

In some embodiments of formula (I), formula (I-1), formula (I-2), formula (I-1a), formula (I-1b), formula (I-2a) and formula (I-2b), preferably, the present invention relates to the above-mentioned compound, or a tautomer, stereoisomer, prodrug, crystal form, pharmaceutically acceptable salt, hydrate or solvate thereof, wherein $X_2$ is $CH_3$, $R_1$-$R_4$ are hydrogen, $X_1$ is selected from $CH_3$, $CD_3$, $CHD_2$, or $CH_2D$, and $Y_1$, $Y_2$, $Y_3$, $Y_4$, $Y_5$, and $Y_6$ are each independently selected from hydrogen or deuterium, provided that the compound comprises at least one deuterium atom.

In some embodiments of formula (I), formula (I-1), formula (I-2), formula (I-1a), formula (I-1b), formula (I-2a) and formula (I-2b), preferably, the present invention relates to the above-mentioned compound, or a tautomer, stereoisomer, prodrug, crystal form, pharmaceutically acceptable salt, hydrate or solvate thereof, wherein $X_1$ is $CD_3$, $R_1$-$R_4$ are each independently selected from hydrogen or deuterium, $X_2$ is selected from $CH_3$, $CD_3$, $CHD_2$, or $CH_2D$, and $Y_1$, $Y_2$, $Y_3$, $Y_4$, $Y_5$, and $Y_6$ are each independently selected from hydrogen or deuterium.

In some embodiments of formula (I), formula (I-1), formula (I-2), formula (I-1a), formula (I-1b), formula (I-2a) and formula (I-2b), preferably, the present invention relates to the above-mentioned compound, or a tautomer, stereoisomer, prodrug, crystal form, pharmaceutically acceptable salt, hydrate or solvate thereof, wherein $X_1$ is $CD_3$, $R_3$ is hydrogen, $R_1$, $R_2$, and $R_4$ are each independently selected from hydrogen or deuterium, $X_2$ is selected from $CH_3$, $CD_3$, $CHD_2$, or $CH_2D$, and $Y_1$, $Y_2$, $Y_3$, $Y_4$, $Y_5$, and $Y_6$ are each independently selected from hydrogen or deuterium.

In some embodiments of formula (I), formula (I-1), formula (I-2), formula (I-1a), formula (I-1b), formula (I-2a) and formula (I-2b), preferably, the present invention relates to the above-mentioned compound, or a tautomer, stereoisomer, prodrug, crystal form, pharmaceutically acceptable salt, hydrate or solvate thereof, wherein $X_1$ is $CD_3$, $R_1$ and $R_2$ are hydrogen, $R_3$ and $R_4$ are each independently selected from hydrogen or deuterium, $X_2$ is selected from $CH_3$, $CD_3$, $CHD_2$ or $CH_2D$, and $Y_1$, $Y_2$, $Y_3$, $Y_4$, $Y_5$ and $Y_6$ are each independently selected from hydrogen or deuterium.

In some embodiments of formula (I), formula (I-1), formula (I-2), formula (I-1a), formula (I-1b), formula (I-2a) and formula (I-2b), preferably, the present invention relates to the above-mentioned compound, or a tautomer, stereoisomer, prodrug, crystal form, pharmaceutically acceptable salt, hydrate or solvate thereof, wherein $X_1$ is $CD_3$, $R_1$-$R_3$ are hydrogen, $R_4$ is selected from hydrogen or deuterium, $X_2$ is selected from $CH_3$, $CD_3$, $CHD_2$ or $CH_2D$, and $Y_1$, $Y_2$, $Y_3$, $Y_4$, $Y_5$ and $Y_6$ are each independently selected from hydrogen or deuterium.

In some embodiments of formula (I), formula (I-1), formula (I-2), formula (I-1a), formula (I-1b), formula (I-2a) and formula (I-2b), preferably, the present invention relates to the above-mentioned compound, or a tautomer, stereoisomer, prodrug, crystal form, pharmaceutically acceptable salt, hydrate or solvate thereof, wherein $X_1$ is $CD_3$, $X_2$ is $CH_3$, $R_1$-$R_4$ are each independently selected from hydrogen or deuterium, and $Y_1$, $Y_2$, $Y_3$, $Y_4$, $Y_5$, and $Y_6$ are each independently selected from hydrogen or deuterium.

In some embodiments of formula (I), formula (I-1), formula (I-2), formula (I-1a), formula (I-1b), formula (I-2a) and formula (I-2b), preferably, the present invention relates to the above-mentioned compound, or a tautomer, stereoisomer, prodrug, crystal form, pharmaceutically acceptable salt, hydrate or solvate thereof, wherein $X_1$ is $CD_3$, $X_2$ is $CH_3$, $R_3$ is hydrogen, $R_1$, $R_2$, and $R_4$ are each independently selected from hydrogen or deuterium, and $Y_1$, $Y_2$, $Y_3$, $Y_4$, $Y_5$, and $Y_6$ are each independently selected from hydrogen or deuterium.

In some embodiments of formula (I), formula (I-1), formula (I-2), formula (I-1a), formula (I-1b), formula (I-2a) and formula (I-2b), preferably, the present invention relates to the above-mentioned compound, or a tautomer, stereoisomer, prodrug, crystal form, pharmaceutically acceptable salt, hydrate or solvate thereof, wherein $X_1$ is $CD_3$, $X_2$ is $CH_3$, $R_1$ and $R_2$ are hydrogen, $R_3$ and $R_4$ are each independently selected from hydrogen or deuterium, and $Y_1$, $Y_2$, $Y_3$, $Y_4$, $Y_5$, and $Y_6$ are each independently selected from hydrogen or deuterium.

In some embodiments of formula (I), formula (I-1), formula (I-2), formula (I-1a), formula (I-1b), formula (I-2a) and formula (I-2b), preferably, the present invention relates to the above-mentioned compound, or a tautomer, stereoisomer, prodrug, crystal form, pharmaceutically acceptable salt, hydrate or solvate thereof, wherein $X_1$ is $CD_3$, $X_2$ is $CH_3$, $R_1$-$R_3$ are hydrogen, $R_4$ is selected from hydrogen or deuterium, and $Y_1$, $Y_2$, $Y_3$, $Y_4$, $Y_5$, and $Y_6$ are each independently selected from hydrogen or deuterium.

In some embodiments of formula (I), formula (I-1), formula (I-2), formula (I-1a), formula (I-1b), formula (I-2a) and formula (I-2b), preferably, the present invention relates to the above-mentioned compound, or a tautomer, stereoisomer, prodrug, crystal form, pharmaceutically acceptable salt, hydrate or solvate thereof, wherein $X_1$ is $CD_3$, $R_4$ is hydrogen, $R_1$-$R_3$ are each independently selected from hydrogen or deuterium, $X_2$ is selected from $CH_3$, $CD_3$, $CHD_2$ or $CH_2D$, and $Y_1$, $Y_2$, $Y_3$, $Y_4$, $Y_5$ and $Y_6$ are each independently selected from hydrogen or deuterium.

In some embodiments of formula (I), formula (I-1), formula (I-2), formula (I-1a), formula (I-1b), formula (I-2a) and formula (I-2b), preferably, the present invention relates to the above-mentioned compound, or a tautomer, stereoisomer, prodrug, crystal form, pharmaceutically acceptable salt, hydrate or solvate thereof, wherein $X_1$ is $CD_3$, $R_3$ and $R_4$ are hydrogen, $R_1$ and $R_2$ are each independently selected from hydrogen or deuterium, $X_2$ is selected from $CH_3$, $CD_3$, $CHD_2$ or $CH_2D$, and $Y_1$, $Y_2$, $Y_3$, $Y_4$, $Y_5$ and $Y_6$ are each independently selected from hydrogen or deuterium.

In some embodiments of formula (I), formula (I-1), formula (I-2), formula (I-1a), formula (I-1b), formula (I-2a) and formula (I-2b), preferably, the present invention relates to the above-mentioned compound, or a tautomer, stereoisomer, prodrug, crystal form, pharmaceutically acceptable salt, hydrate or solvate thereof, wherein $X_1$ is $CD_3$, $R_1$, $R_2$ and $R_4$ are hydrogen, $R_3$ is selected from hydrogen or deuterium, $X_2$ is selected from $CH_3$, $CD_3$, $CHD_2$ or $CH_2D$, and $Y_1$, $Y_2$, $Y_3$, $Y_4$, $Y_5$ and $Y_6$ are each independently selected from hydrogen or deuterium.

In some embodiments of formula (I), formula (I-1), formula (I-2), formula (I-1a), formula (I-1b), formula (I-2a) and formula (I-2b), preferably, the present invention relates to the above-mentioned compound, or a tautomer, stereoisomer, prodrug, crystal form, pharmaceutically acceptable salt, hydrate or solvate thereof, wherein $X_1$ is $CD_3$, $R_1$-$R_4$ are hydrogen, $X_2$ is selected from $CH_3$, $CD_3$, $CHD_2$, or $CH_2D$, and $Y_1$, $Y_2$, $Y_3$, $Y_4$, $Y_5$, and $Y_6$ are each independently selected from hydrogen or deuterium.

In some embodiments of formula (I), formula (I-1), formula (I-2), formula (I-1a), formula (I-1b), formula (I-2a) and formula (I-2b), preferably, the present invention relates to the above-mentioned compound, or a tautomer, stereoisomer, prodrug, crystal form, pharmaceutically acceptable salt, hydrate or solvate thereof, wherein $X_1$ is $CD_3$, $R_4$ is hydrogen, $X_2$ is $CH_3$, $R_1$-$R_3$ are each independently selected from hydrogen or deuterium, and $Y_1$, $Y_2$, $Y_3$, $Y_4$, $Y_5$, and $Y_6$ are each independently selected from hydrogen or deuterium.

In some embodiments of formula (I), formula (I-1), formula (I-2), formula (I-1a), formula (I-1b), formula (I-2a) and formula (I-2b), preferably, the present invention relates to the above-mentioned compound, or a tautomer, stereoisomer, prodrug, crystal form, pharmaceutically acceptable salt, hydrate or solvate thereof, wherein $X_1$ is $CD_3$, $R_3$ and $R_4$ are hydrogen, $X_2$ is $CH_3$, $R_1$ and $R_2$ are each independently selected from hydrogen or deuterium, and $Y_1$, $Y_2$, $Y_3$, $Y_4$, $Y_5$, and $Y_6$ are each independently selected from hydrogen or deuterium.

In some embodiments of formula (I), formula (I-1), formula (I-2), formula (I-1a), formula (I-1b), formula (I-2a) and formula (I-2b), preferably, the present invention relates to the above-mentioned compound, or a tautomer, stereoisomer, prodrug, crystal form, pharmaceutically acceptable salt, hydrate or solvate thereof, wherein $X_1$ is $CD_3$, $R_1$, $R_2$, and $R_4$ are hydrogen, $X_2$ is $CH_3$, $R_3$ is selected from hydrogen or deuterium, and $Y_1$, $Y_2$, $Y_3$, $Y_4$, $Y_5$, and $Y_6$ are each independently selected from hydrogen or deuterium.

In some embodiments of formula (I), formula (I-1), formula (I-2), formula (I-1a), formula (I-1b), formula (I-2a) and formula (I-2b), preferably, the present invention relates to the above-mentioned compound, or a tautomer, stereoisomer, prodrug, crystal form, pharmaceutically acceptable salt, hydrate or solvate thereof, wherein $X_1$ is $CD_3$, $X_2$ is $CH_3$, $R_1$-$R_4$ are hydrogen, and $Y_1$, $Y_2$, $Y_3$, $Y_4$, $Y_5$, and $Y_6$ are each independently selected from hydrogen or deuterium.

In some embodiments of formula (I), formula (I-1), formula (I-2), formula (I-1a), formula (I-1b), formula (I-2a) and formula (I-2b), preferably, the present invention relates to the above-mentioned compound, or a tautomer, stereoisomer, prodrug, crystal form, pharmaceutically acceptable salt, hydrate or solvate thereof, wherein $X_1$ is $CD_3$, $R_1$-$R_4$ are each independently selected from hydrogen or deuterium, $X_2$ is selected from $CH_3$, $CD_3$, $CHD_2$ or $CH_2D$, and $Y_1$-$Y_6$ are each independently selected from hydrogen or deuterium.

In some embodiments of formula (I), formula (I-1), formula (I-2), formula (I-1a), formula (I-1b), formula (I-2a) and formula (I-2b), preferably, the present invention relates to the above-mentioned compound, or a tautomer, stereoisomer, prodrug, crystal form, pharmaceutically acceptable salt, hydrate or solvate thereof, wherein $X_2$ is $CD_3$, $R_1$-$R_4$ are each independently selected from hydrogen or deuterium, $X_1$ is selected from $CH_3$, $CD_3$, $CHD_2$, or $CH_2D$, and $Y_1$-$Y_6$ are each independently selected from hydrogen or deuterium.

In some embodiments of formula (I), formula (I-1), formula (I-2), formula (I-1a), formula (I-1b), formula (I-2a) and formula (I-2b), preferably, the present invention relates to the above-mentioned compound, or a tautomer, stereoisomer, prodrug, crystal form, pharmaceutically acceptable salt, hydrate or solvate thereof, wherein $X_1$ and $X_2$ are $CD_3$, $R_1$-$R_4$ are each independently selected from hydrogen or deuterium, and $Y_1$-$Y_6$ are each independently selected from hydrogen or deuterium.

In some embodiments of formula (I), formula (I-1), formula (I-2), formula (I-1a), formula (I-1b), formula (I-2a) and formula (I-2b), preferably, the present invention relates to the above-mentioned compound, or a tautomer, stereoisomer, prodrug, crystal form, pharmaceutically acceptable salt, hydrate or solvate thereof, wherein $R_3$ is deuterium, $R_1$, $R_2$, and $R_4$ are each independently selected from hydrogen or deuterium, $X_1$ and $X_2$ are each independently selected from $CH_3$, $CD_3$, $CHD_2$, or $CH_2D$, and $Y_1$-$Y_6$ are each independently selected from hydrogen or deuterium.

In some embodiments of formula (I), formula (I-1), formula (I-2), formula (I-1a), formula (I-1b), formula (I-2a) and formula (I-2b), preferably, the present invention relates to the above-mentioned compound, or a tautomer, stereoisomer, prodrug, crystal form, pharmaceutically acceptable salt, hydrate or solvate thereof, wherein $R_3$ is deuterium, $X_1$ is $CD_3$, $R_1$, $R_2$ and $R_4$ are each independently selected from hydrogen or deuterium, $X_2$ is selected from $CH_3$, $CD_3$, $CHD_2$ or $CH_2D$, and $Y_1$-$Y_6$ are each independently selected from hydrogen or deuterium.

In some embodiments of formula (I), formula (I-1), formula (I-2), formula (I-1a), formula (I-1b), formula (I-2a) and formula (I-2b), preferably, the present invention relates to the above-mentioned compound, or a tautomer, stereoisomer, prodrug, crystal form, pharmaceutically acceptable salt, hydrate or solvate thereof, wherein $R_3$ is deuterium, $X_2$ is $CD_3$, $R_1$, $R_2$ and $R_4$ are each independently selected from hydrogen or deuterium, $X_1$ is selected from $CH_3$, $CD_3$, $CHD_2$ or $CH_2D$, and $Y_1$-$Y_6$ are each independently selected from hydrogen or deuterium.

In some embodiments of formula (I), formula (I-1), formula (I-2), formula (I-1a), formula (I-1b), formula (I-2a) and formula (I-2b), preferably, the present invention relates to the above-mentioned compound, or a tautomer, stereoisomer, prodrug, crystal form, pharmaceutically acceptable salt, hydrate or solvate thereof, wherein $R_3$ is deuterium, $X_1$ and $X_2$ are $CD_3$, $R_1$, $R_2$, and $R_4$ are each independently selected from hydrogen or deuterium, and $Y_1$-$Y_6$ are each independently selected from hydrogen or deuterium.

In some embodiments of formula (I), formula (I-1), formula (I-2), formula (I-1a), formula (I-1b), formula (I-2a) and formula (I-2b), preferably, the present invention relates to the above-mentioned compound, or a tautomer, stereoisomer, prodrug, crystal form, pharmaceutically acceptable salt, hydrate or solvate thereof, wherein $R_1$ and $R_2$ are deuterium, $R_3$ and $R_4$ are each independently selected from hydrogen or deuterium, $X_1$ and $X_2$ are each independently selected from $CH_3$, $CD_3$, $CHD_2$ or $CH_2D$, and $Y_1$-$Y_6$ are each independently selected from hydrogen or deuterium.

In some embodiments of formula (I), formula (I-1), formula (I-2), formula (I-1a), formula (I-1b), formula (I-2a) and formula (I-2b), preferably, the present invention relates to the above-mentioned compound, or a tautomer, stereoisomer, prodrug, crystal form, pharmaceutically acceptable salt, hydrate or solvate thereof, wherein $R_1$ and $R_2$ are deuterium, $X_1$ is $CD_3$, $R_3$ and $R_4$ are each independently selected from hydrogen or deuterium, $X_2$ is selected from $CH_3$, $CD_3$, $CHD_2$ or $CH_2D$, and $Y_1$-$Y_6$ are each independently selected from hydrogen or deuterium.

In some embodiments of formula (I), formula (I-1), formula (I-2), formula (I-1a), formula (I-1b), formula (I-2a) and formula (I-2b), preferably, the present invention relates to the above-mentioned compound, or a tautomer, stereoisomer, prodrug, crystal form, pharmaceutically acceptable salt, hydrate or solvate thereof, wherein $R_1$ and $R_2$ are Deuterium, $X_2$ is $CD_3$, $R_3$ and $R_4$ are each independently selected from hydrogen or deuterium, $X_1$ is selected from $CH_3$, $CD_3$, $CHD_2$ or $CH_2D$, and $Y_1$-$Y_6$ are each independently selected from hydrogen or deuterium.

In some embodiments of formula (I), formula (I-1), formula (I-2), formula (I-1a), formula (I-1b), formula (I-2a) and formula (I-2b), preferably, the present invention relates to the above-mentioned compound, or a tautomer, stereoisomer, prodrug, crystal form, pharmaceutically acceptable salt, hydrate or solvate thereof, wherein $R_1$ and $R_2$ are deuterium, $X_1$ and $X_2$ are $CD_3$, $R_3$ and $R_4$ are each independently selected from hydrogen or deuterium, and $Y_1$-$Y_6$ are each independently selected from hydrogen or deuterium.

In some embodiments of formula (I), formula (I-1), formula (I-2), formula (I-1a), formula (I-1b), formula (I-2a) and formula (I-2b), preferably, the present invention relates to the above-mentioned compound, or a tautomer, stereoisomer, prodrug, crystal form, pharmaceutically acceptable salt, hydrate or solvate thereof, wherein $R_1$-$R_3$ are deuterium, $R_4$ is each independently selected from hydrogen or deuterium, $X_1$ and $X_2$ are each independently selected from $CH_3$, $CD_3$, $CHD_2$ or $CH_2D$, and $Y_1$-$Y_6$ are each independently selected from hydrogen or deuterium.

In some embodiments of formula (I), formula (I-1), formula (I-2), formula (I-1a), formula (I-1b), formula (I-2a) and formula (I-2b), preferably, the present invention relates to the above-mentioned compound, or a tautomer, stereoisomer, prodrug, crystal form, pharmaceutically acceptable salt, hydrate or solvate thereof, wherein $R_1$-$R_3$ are deuterium, $X_1$ is $CD_3$, $R_4$ is each independently selected from hydrogen or deuterium, $X_2$ is selected from $CH_3$, $CD_3$, $CHD_2$ or $CH_2D$, and $Y_1$-$Y_6$ are each independently selected from hydrogen or deuterium.

In some embodiments of formula (I), formula (I-1), formula (I-2), formula (I-1a), formula (I-1b), formula (I-2a) and formula (I-2b), preferably, the present invention relates to the above-mentioned compound, or a tautomer, stereoisomer, prodrug, crystal form, pharmaceutically acceptable salt, hydrate or solvate thereof, wherein $R_1$-$R_3$ are deuterium, $X_2$ is $CD_3$, $R_4$ is each independently selected from hydrogen or deuterium, $X_1$ is selected from $CH_3$, $CD_3$, $CHD_2$ or $CH_2D$, and $Y_1$-$Y_6$ are each independently selected from hydrogen or deuterium.

In some embodiments of formula (I), formula (I-1), formula (I-2), formula (I-1a), formula (I-1b), formula (I-2a) and formula (I-2b), preferably, the present invention relates to the above-mentioned compound, or a tautomer, stereoisomer, prodrug, crystal form, pharmaceutically acceptable salt, hydrate or solvate thereof, wherein $R_1$-$R_3$ are deuterium, $X_1$ and $X_2$ are $CD_3$, $R_4$ is each independently selected from hydrogen or deuterium, and $Y_1$-$Y_6$ are each independently selected from hydrogen or deuterium.

In some embodiments of formula (I), formula (I-1), formula (I-2), formula (I-1a), formula (I-1b), formula (I-2a) and formula (I-2b), preferably, the present invention relates to the above-mentioned compound, or a tautomer, stereoisomer, prodrug, crystal form, pharmaceutically acceptable salt, hydrate or solvate thereof, wherein $R_4$ is deuterium, $R_1$-$R_3$ are each independently selected from hydrogen or deuterium, $X_1$ and $X_2$ are each independently selected from $CH_3$, $CD_3$, $CHD_2$, or $CH_2D$, and $Y_1$-$Y_6$ are each independently selected from hydrogen or deuterium.

In some embodiments of formula (I), formula (I-1), formula (I-2), formula (I-1a), formula (I-1b), formula (I-2a) and formula (I-2b), preferably, the present invention relates to the above-mentioned compound, or a tautomer, stereoisomer, prodrug, crystal form, pharmaceutically acceptable salt, hydrate or solvate thereof, wherein $R_4$ is deuterium, $X_1$ is $CD_3$, $R_1$-$R_3$ are each independently selected from hydrogen or deuterium, $X_2$ is selected from $CH_3$, $CD_3$, $CHD_2$ or $CH_2D$, and $Y_1$-$Y_6$ are each independently selected from hydrogen or deuterium.

In some embodiments of formula (I), formula (I-1), formula (I-2), formula (I-1a), formula (I-1b), formula (I-2a) and formula (I-2b), preferably, the present invention relates to the above-mentioned compound, or a tautomer, stereoisomer, prodrug, crystal form, pharmaceutically acceptable salt, hydrate or solvate thereof, wherein $R_4$ is deuterium, $X_2$ is $CD_3$, $R_1$-$R_3$ are each independently selected from hydrogen or deuterium, $X_1$ is selected from $CH_3$, $CD_3$, $CHD_2$ or $CH_2D$, and $Y_1$-$Y_6$ are each independently selected from hydrogen or deuterium.

In some embodiments of formula (I), formula (I-1), formula (I-2), formula (I-1a), formula (I-1b), formula (I-2a) and formula (I-2b), preferably, the present invention relates to the above-mentioned compound, or a tautomer, stereoisomer, prodrug, crystal form, pharmaceutically acceptable salt, hydrate or solvate thereof, wherein $R_4$ is deuterium, $X_1$ and $X_2$ are $CD_3$, $R_1$-$R_3$ are each independently selected from hydrogen or deuterium, and $Y_1$-$Y_6$ are each independently selected from hydrogen or deuterium.

In some embodiments of formula (I), formula (I-1), formula (I-2), formula (I-1a), formula (I-1b), formula (I-2a) and formula (I-2b), preferably, the present invention relates to the above-mentioned compound, or a tautomer, stereoisomer, prodrug, crystal form, pharmaceutically acceptable salt, hydrate or solvate thereof, wherein $R_3$ and $R_4$ are deuterium, $R_1$ and $R_2$ are each independently selected from hydrogen or deuterium, $X_1$ and $X_2$ are each independently selected from $CH_3$, $CD_3$, $CHD_2$ or $CH_2D$, and $Y_1$-$Y_6$ are each independently selected from hydrogen or deuterium.

In some embodiments of formula (I), formula (I-1), formula (I-2), formula (I-1a), formula (I-1b), formula (I-2a) and formula (I-2b), preferably, the present invention relates to the above-mentioned compound, or a tautomer, stereoisomer, prodrug, crystal form, pharmaceutically acceptable salt, hydrate or solvate thereof, wherein $R_3$ and $R_4$ are deuterium, $X_1$ is $CD_3$, $R_1$ and $R_2$ are each independently selected from hydrogen or deuterium, $X_2$ is selected from $CH_3$, $CD_3$, $CHD_2$ or $CH_2D$, and $Y_1$-$Y_6$ are each independently selected from hydrogen or deuterium.

In some embodiments of formula (I), formula (I-1), formula (I-2), formula (I-1a), formula (I-1b), formula (I-2a) and formula (I-2b), preferably, the present invention relates to the above-mentioned compound, or a tautomer, stereoisomer, prodrug, crystal form, pharmaceutically acceptable salt, hydrate or solvate thereof, wherein $R_3$ and $R_4$ are deuterium, $X_2$ is $CD_3$, $R_1$ and $R_2$ are each independently selected from hydrogen or deuterium, $X_1$ is selected from $CH_3$, $CD_3$, $CHD_2$ or $CH_2D$, and $Y_1$-$Y_6$ are each independently selected from hydrogen or deuterium.

In some embodiments of formula (I), formula (I-1), formula (I-2), formula (I-1a), formula (I-1b), formula (I-2a) and formula (I-2b), preferably, the present invention relates to the above-mentioned compound, or a tautomer, stereoisomer, prodrug, crystal form, pharmaceutically acceptable salt, hydrate or solvate thereof, wherein $R_3$ and $R_4$ are deuterium, $X_1$ and $X_2$ are $CD_3$, $R_1$ and $R_2$ are each independently selected from hydrogen or deuterium, and $Y_1$-$Y_6$ are each independently selected from hydrogen or deuterium.

In some embodiments of formula (I), formula (I-1), formula (I-2), formula (I-1a), formula (I-1b), formula (I-2a) and formula (I-2b), preferably, the present invention relates to the above-mentioned compound, or a tautomer, stereoisomer, prodrug, crystal form, pharmaceutically acceptable salt, hydrate or solvate thereof, wherein $R_1$, $R_2$ and $R_4$ are deuterium, $R_3$ is selected from hydrogen or deuterium, $X_1$ and $X_2$ are each independently selected from $CH_3$, $CD_3$, $CHD_2$, or $CH_2D$, and $Y_1$-$Y_6$ are each independently selected from hydrogen or deuterium.

In some embodiments of formula (I), formula (I-1), formula (I-2), formula (I-1a), formula (I-1b), formula (I-2a) and formula (I-2b), preferably, the present invention relates to the above-mentioned compound, or a tautomer, stereoisomer, prodrug, crystal form, pharmaceutically acceptable salt, hydrate or solvate thereof, wherein $R_1$, $R_2$ and $R_4$ are deuterium, $X_1$ is $CD_3$, $R_3$ is selected from hydrogen or deuterium, $X_2$ is selected from $CH_3$, $CD_3$, $CHD_2$ or $CH_2D$, and $Y_1$-$Y_6$ are each independently selected from hydrogen or deuterium.

In some embodiments of formula (I), formula (I-1), formula (I-2), formula (I-1a), formula (I-1b), formula (I-2a) and formula (I-2b), preferably, the present invention relates to the above-mentioned compound, or a tautomer, stereoisomer, prodrug, crystal form, pharmaceutically acceptable salt, hydrate or solvate thereof, wherein $R_1$, $R_2$ and $R_4$ are deuterium, $X_2$ is $CD_3$, $R_3$ is selected from hydrogen or deuterium, $X_1$ is selected from $CH_3$, $CD_3$, $CHD_2$ or $CH_2D$, and $Y_1$-$Y_6$ are each independently selected from hydrogen or deuterium.

In some embodiments of formula (I), formula (I-1), formula (I-2), formula (I-1a), formula (I-1b), formula (I-2a) and formula (I-2b), preferably, the present invention relates to the above-mentioned compound, or a tautomer, stereoisomer, prodrug, crystal form, pharmaceutically acceptable salt, hydrate or solvate thereof, wherein $R_1$, $R_2$ and $R_4$ are deuterium, $X_1$ and $X_2$ are $CD_3$, $R_3$ is selected from hydrogen or deuterium, and $Y_1$-$Y_6$ are each independently selected from hydrogen or deuterium.

In some embodiments of formula (I), formula (I-1), formula (I-2), formula (I-1a), formula (I-1b), formula (I-2a) and formula (I-2b), preferably, the present invention relates to the above-mentioned compound, or a tautomer, stereoisomer, prodrug, crystal form, pharmaceutically acceptable salt, hydrate or solvate thereof, wherein $R_1$-$R_4$ are deuterium, $X_1$ and $X_2$ are each independently selected from $CH_3$, $CD_3$, $CHD_2$, or $CH_2D$, and $Y_1$-$Y_6$ are each independently selected from hydrogen or deuterium.

In some embodiments of formula (I), formula (I-1), formula (I-2), formula (I-1a), formula (I-1b), formula (I-2a) and formula (I-2b), preferably, the present invention relates to the above-mentioned compound, or a tautomer, stereoisomer, prodrug, crystal form, pharmaceutically acceptable salt, hydrate or solvate thereof, wherein $R_1$-$R_4$ are deuterium, $X_1$ is $CD_3$, $X_2$ is selected from $CH_3$, $CD_3$, $CHD_2$ or $CH_2D$, and $Y_1$-$Y_6$ are each independently selected from hydrogen or deuterium.

In some embodiments of formula (I), formula (I-1), formula (I-2), formula (I-1a), formula (I-1b), formula (I-2a) and formula (I-2b), preferably, the present invention relates to the above-mentioned compound, or a tautomer, stereoisomer, prodrug, crystal form, pharmaceutically acceptable salt, hydrate or solvate thereof, wherein $R_1$-$R_4$ are deuterium, $X_2$ is $CD_3$, $X_1$ is selected from $CH_3$, $CD_3$, $CHD_2$ or $CH_2D$, and $Y_1$-$Y_6$ are each independently selected from hydrogen or deuterium.

In some embodiments of formula (I), formula (I-1), formula (I-2), formula (I-1a), formula (I-1b), formula (I-2a) and formula (I-2b), preferably, the present invention relates to the above-mentioned compound, or a tautomer, stereoisomer, prodrug, crystal form, pharmaceutically acceptable salt, hydrate or solvate thereof, wherein $R_1$-$R_4$ are deuterium, $X_1$ and $X_2$ are $CD_3$, and $Y_1$-$Y_6$ are each independently selected from hydrogen or deuterium.

In another embodiment, the present invention relates to a compound of formula (II):

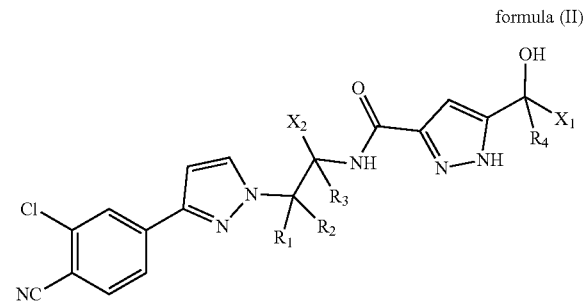

formula (II)

wherein
- $R_1$, $R_2$, $R_3$ and $R_4$ are each independently selected from hydrogen or deuterium;
- $X_1$ and $X_2$ are each independently selected from $CH_3$, $CD_3$, $CHD_2$ or $CH_2D$;
- provided that the compound comprises at least one deuterium atom;
- or a tautomer, stereoisomer, prodrug, crystal form, pharmaceutically acceptable salt, hydrate or solvate thereof.

In another embodiment, the present invention relates to a compound of formula (II-1):

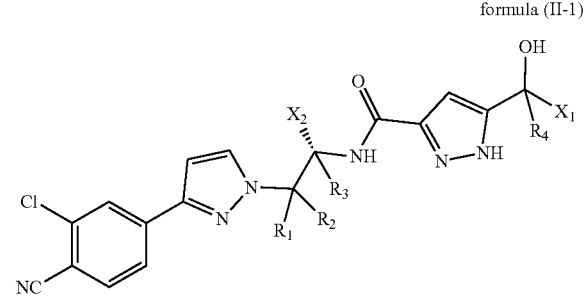

formula (II-1)

wherein $R_1$, $R_2$, $R_3$, $R_4$, $X_1$ and $X_2$ are as defined above;

or a tautomer, stereoisomer, prodrug, crystal form, pharmaceutically acceptable salt, hydrate or solvate thereof.

In another embodiment, the present invention relates to a compound of formula (II-1a):

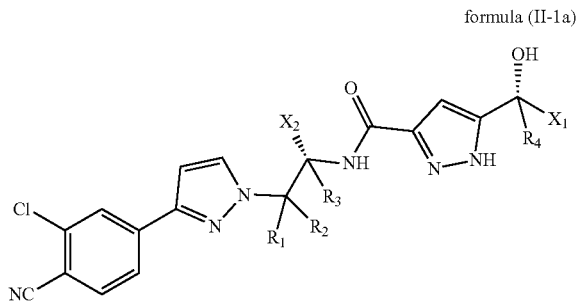

formula (II-1a)

wherein $R_1$, $R_2$, $R_3$, $R_4$, $X_1$ and $X_2$ are as defined above;

or a tautomer, stereoisomer, prodrug, crystal form, pharmaceutically acceptable salt, hydrate or solvate thereof.

In another embodiment, the present invention relates to a compound of formula (II-1b):

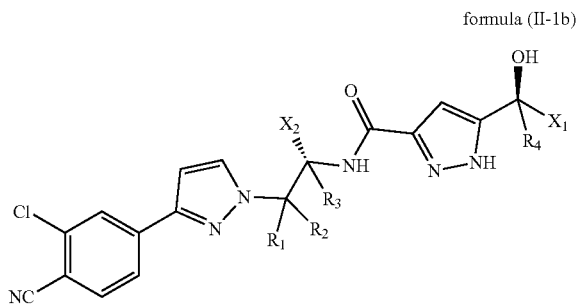

formula (II-1b)

wherein $R_1$, $R_2$, $R_3$, $R_4$, $X_1$ and $X_2$ are as defined above;

or a tautomer, stereoisomer, prodrug, crystal form, pharmaceutically acceptable salt, hydrate or solvate thereof.

In another embodiment, the present invention relates to a compound of formula (II-2):

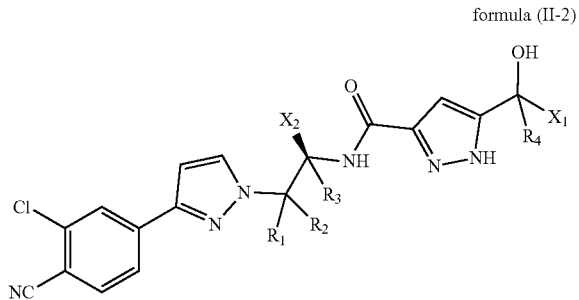

formula (II-2)

wherein $R_1$, $R_2$, $R_3$, $R_4$, $X_1$ and $X_2$ are as defined above;

or a tautomer, stereoisomer, prodrug, crystal form, pharmaceutically acceptable salt, hydrate or solvate thereof.

In another embodiment, the present invention relates to a compound of formula (II-2a):

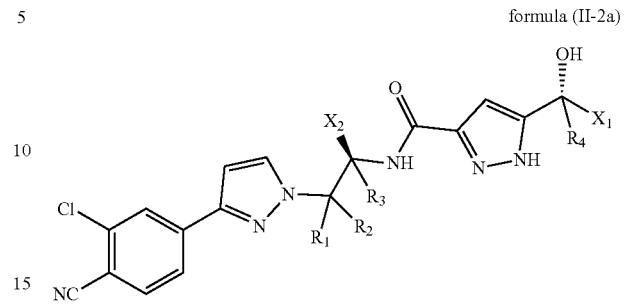

formula (II-2a)

wherein $R_1$, $R_2$, $R_3$, $R_4$, $X_1$ and $X_2$ are as defined above;

or a tautomer, stereoisomer, prodrug, crystal form, pharmaceutically acceptable salt, hydrate or solvate thereof.

In another embodiment, the present invention relates to a compound of formula (II-2b):

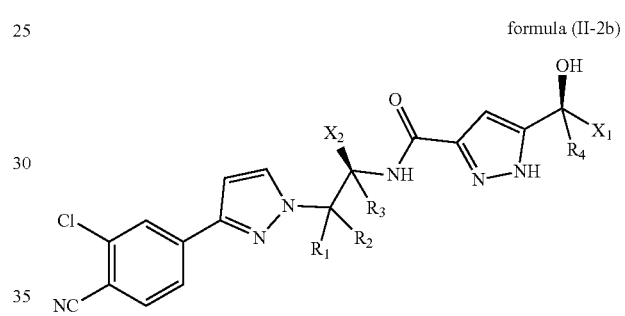

formula (II-2b)

wherein $R_1$, $R_2$, $R_3$, $R_4$, $X_1$ and $X_2$ are as defined above;

or a tautomer, stereoisomer, prodrug, crystal form, pharmaceutically acceptable salt, hydrate or solvate thereof.

In some embodiments of formula (II), formula (II-1), formula (II-2), formula (II-1a), formula (II-1b), formula (II-2a) and formula (II-2b), preferably, the present invention relates to the above-mentioned compound, or a tautomer, stereoisomer, prodrug, crystal form, pharmaceutically acceptable salt, hydrate or solvate thereof, wherein $R_3$ is hydrogen, $R_1$, $R_2$ and $R_4$ are each independently selected from hydrogen or deuterium, and $X_1$ and $X_2$ are each independently selected from $CH_3$, $CD_3$, $CHD_2$, or $CH_2D$, provided that the compound comprises at least one deuterium atom.

In some embodiments of formula (II), formula (II-1), formula (II-2), formula (II-1a), formula (II-1b), formula (II-2a) and formula (II-2b), preferably, the present invention relates to the above-mentioned compound, or a tautomer, stereoisomer, prodrug, crystal form, pharmaceutically acceptable salt, hydrate or solvate thereof, wherein $R_1$ and $R_2$ are hydrogen, $R_3$ and $R_4$ are each independently selected from hydrogen or deuterium, and $X_1$ and $X_2$ are each independently selected from $CH_3$, $CD_3$, $CHD_2$ or $CH_2D$, provided that the compound comprises at least one deuterium atom.

In some embodiments of formula (II), formula (II-1), formula (II-2), formula (II-1a), formula (II-1b), formula (II-2a) and formula (II-2b), preferably, the present invention relates to the above-mentioned compound, or a tautomer, stereoisomer, prodrug, crystal form, pharmaceutically acceptable salt, hydrate or solvate thereof, wherein $R_1$-$R_3$ are hydrogen, $R_4$ is selected from hydrogen or deuterium, and $X_1$ and $X_2$ are each independently selected from $CH_3$, $CD_3$, $CHD_2$ or $CH_2D$, provided that the compound comprises at least one deuterium atom.

In some embodiments of formula (II), formula (II-1), formula (II-2), formula (II-1a), formula (II-1b), formula (II-2a) and formula (II-2b), preferably, the present invention relates to the above-mentioned compound, or a tautomer, stereoisomer, prodrug, crystal form, pharmaceutically acceptable salt, hydrate or solvate thereof, wherein $X_2$ is $CH_3$, $R_1$-$R_4$ are each independently selected from hydrogen or deuterium, and $X_1$ is selected from $CH_3$, $CD_3$, $CHD_2$, or $CH_2D$, provided that the compound comprises at least one deuterium atom.

In some embodiments of formula (II), formula (II-1), formula (II-2), formula (II-1a), formula (II-1b), formula (II-2a) and formula (II-2b), preferably, the present invention relates to the above-mentioned compound, or a tautomer, stereoisomer, prodrug, crystal form, pharmaceutically acceptable salt, hydrate or solvate thereof, wherein $X_2$ is $CH_3$, $R_3$ is hydrogen, $R_1$, $R_2$ and $R_4$ are each independently selected from hydrogen or deuterium, and $X_1$ is selected from $CH_3$, $CD_3$, $CHD_2$ or $CH_2D$, provided that the compound comprises at least one deuterium atom.

In some embodiments of formula (II), formula (II-1), formula (II-2), formula (II-1a), formula (II-1b), formula (II-2a) and formula (II-2b), preferably, the present invention relates to the above-mentioned compound, or a tautomer, stereoisomer, prodrug, crystal form, pharmaceutically acceptable salt, hydrate or solvate thereof, wherein $X_2$ is $CH_3$, $R_1$ and $R_2$ are hydrogen, $R_3$ and $R_4$ are each independently selected from hydrogen or deuterium, and $X_1$ is selected from $CH_3$, $CD_3$, $CHD_2$ or $CH_2D$, provided that the compound comprises at least one deuterium atom.

In some embodiments of formula (II), formula (II-1), formula (II-2), formula (II-1a), formula (II-1b), formula (II-2a) and formula (II-2b), preferably, the present invention relates to the above-mentioned compound, or a tautomer, stereoisomer, prodrug, crystal form, pharmaceutically acceptable salt, hydrate or solvate thereof, wherein $X_2$ is $CH_3$, $R_1$-$R_3$ are hydrogen, $R_4$ is selected from hydrogen or deuterium, and $X_1$ is selected from $CH_3$, $CD_3$, $CHD_2$ or $CH_2D$, provided that the compound comprises at least one deuterium atom.

In some embodiments of formula (II), formula (II-1), formula (II-2), formula (II-1a), formula (II-1b), formula (II-2a) and formula (II-2b), preferably, the present invention relates to the above-mentioned compound, or a tautomer, stereoisomer, prodrug, crystal form, pharmaceutically acceptable salt, hydrate or solvate thereof, wherein $R_4$ is hydrogen, $R_1$-$R_3$ are each independently selected from hydrogen or deuterium, and $X_1$ and $X_2$ are each independently selected from $CH_3$, $CD_3$, $CHD_2$, or $CH_2D$, provided that the compound comprises at least one deuterium atom.

In some embodiments of formula (II), formula (II-1), formula (II-2), formula (II-1a), formula (II-1b), formula (II-2a) and formula (II-2b), preferably, the present invention relates to the above-mentioned compound, or a tautomer, stereoisomer, prodrug, crystal form, pharmaceutically acceptable salt, hydrate or solvate thereof, wherein $R_3$ and $R_4$ are Hydrogen, $R_1$ and $R_2$ are each independently selected from hydrogen or deuterium, and $X_1$ and $X_2$ are each independently selected from $CH_3$, $CD_3$, $CHD_2$ or $CH_2D$, provided that the compound comprises at least one deuterium atom.

In some embodiments of formula (II), formula (II-1), formula (II-2), formula (II-1a), formula (II-1b), formula (II-2a) and formula (II-2b), preferably, the present invention relates to the above-mentioned compound, or a tautomer, stereoisomer, prodrug, crystal form, pharmaceutically acceptable salt, hydrate or solvate thereof, wherein $R_1$, $R_2$ and $R_4$ are hydrogen, $R_3$ is each independently selected from hydrogen or deuterium, and $X_1$ and $X_2$ are each independently selected from $CH_3$, $CD_3$, $CHD_2$, or $CH_2D$, provided that the compound comprises at least one deuterium atom.

In some embodiments of formula (II), formula (II-1), formula (II-2), formula (II-1a), formula (II-1b), formula (II-2a) and formula (II-2b), preferably, the present invention relates to the above-mentioned compound, or a tautomer, stereoisomer, prodrug, crystal form, pharmaceutically acceptable salt, hydrate or solvate thereof, wherein $R_1$-$R_4$ are Hydrogen, $X_1$ and $X_2$ are each independently selected from $CH_3$, $CD_3$, $CHD_2$ or $CH_2D$, provided that the compound comprises at least one deuterium atom.

In some embodiments of formula (II), formula (II-1), formula (II-2), formula (II-1a), formula (II-1b), formula (II-2a) and formula (II-2b), preferably, the present invention relates to the above-mentioned compound, or a tautomer, stereoisomer, prodrug, crystal form, pharmaceutically acceptable salt, hydrate or solvate thereof, wherein $R_4$ is hydrogen, $X_2$ is $CH_3$, $R_1$-$R_3$ are each independently selected from hydrogen or deuterium, and $X_1$ is selected from $CH_3$, $CD_3$, $CHD_2$ or $CH_2D$, provided that the compound comprises at least one deuterium atom.

In some embodiments of formula (II), formula (II-1), formula (II-2), formula (II-1a), formula (II-1b), formula (II-2a) and formula (II-2b), preferably, the present invention relates to the above-mentioned compound, or a tautomer, stereoisomer, prodrug, crystal form, pharmaceutically acceptable salt, hydrate or solvate thereof, wherein $R_3$ and $R_4$ are hydrogen, $X_2$ is $CH_3$, $R_1$ and $R_2$ are each independently selected from hydrogen or deuterium, and $X_1$ is selected from $CH_3$, $CD_3$, $CHD_2$ or $CH_2D$, provided that the compound comprises at least one deuterium atom.

In some embodiments of formula (II), formula (II-1), formula (II-2), formula (II-1a), formula (II-1b), formula (II-2a) and formula (II-2b), preferably, the present invention relates to the above-mentioned compound, or a tautomer, stereoisomer, prodrug, crystal form, pharmaceutically acceptable salt, hydrate or solvate thereof, wherein $R_1$, $R_2$ and $R_4$ are hydrogen, $X_2$ is $CH_3$, $R_3$ is selected from hydrogen or deuterium, and $X_1$ is selected from $CH_3$, $CD_3$, $CHD_2$ or $CH_2D$, provided that the compound comprises at least one deuterium atom.

In some embodiments of formula (II), formula (II-1), formula (II-2), formula (II-1a), formula (II-1b), formula (II-2a) and formula (II-2b), preferably, the present invention relates to the above-mentioned compound, or a tautomer, stereoisomer, prodrug, crystal form, pharmaceutically acceptable salt, hydrate or solvate thereof, wherein $X_2$ is $CH_3$, $R_1$-$R_4$ are hydrogen, and $X_1$ is selected from $CH_3$, $CD_3$, $CHD_2$ or $CH_2D$, provided that the compound comprises at least one deuterium atom.

In some embodiments of formula (II), formula (II-1), formula (II-2), formula (II-1a), formula (II-1b), formula (II-2a) and formula (II-2b), preferably, the present invention relates to the above-mentioned compound, or a tautomer, stereoisomer, prodrug, crystal form, pharmaceutically acceptable salt, hydrate or solvate thereof, wherein $X_1$ is $CD_3$, $R_1$-$R_4$ are each independently selected from hydrogen or deuterium, and $X_2$ is selected from $CH_3$, $CD_3$, $CHD_2$, or $CH_2D$.

In some embodiments of formula (II), formula (II-1), formula (II-2), formula (II-1a), formula (II-1b), formula (II-2a) and formula (II-2b), preferably, the present invention relates to the above-mentioned compound, or a tautomer, stereoisomer, prodrug, crystal form, pharmaceutically acceptable salt, hydrate or solvate thereof, wherein $X_1$ is $CD_3$, $R_3$ is hydrogen, $R_1$, $R_2$ and $R_4$ are each independently selected from hydrogen or deuterium, and $X_2$ is selected from $CH_3$, $CD_3$, $CHD_2$, or $CH_2D$.

In some embodiments of formula (II), formula (II-1), formula (II-2), formula (II-1a), formula (II-1b), formula (II-2a) and formula (II-2b), preferably, the present invention relates to the above-mentioned compound, or a tautomer, stereoisomer, prodrug, crystal form, pharmaceutically acceptable salt, hydrate or solvate thereof, wherein $X_1$ is $CD_3$, $R_1$ and $R_2$ are hydrogen, $R_3$ and $R_4$ are each independently selected from hydrogen or deuterium, and $X_2$ is selected from $CH_3$, $CD_3$, $CHD_2$, or $CH_2D$.

In some embodiments of formula (II), formula (II-1), formula (II-2), formula (II-1a), formula (II-1b), formula (II-2a) and formula (II-2b), preferably, the present invention relates to the above-mentioned compound, or a tautomer, stereoisomer, prodrug, crystal form, pharmaceutically acceptable salt, hydrate or solvate thereof, wherein $X_1$ is $CD_3$, $R_1$-$R_3$ are hydrogen, $R_4$ is selected from hydrogen or deuterium, and $X_2$ is selected from $CH_3$, $CD_3$, $CHD_2$ or $CH_2D$, provided that the compound comprises at least one deuterium atom.

In some embodiments of formula (II), formula (II-1), formula (II-2), formula (II-1a), formula (II-1b), formula (II-2a) and formula (II-2b), preferably, the present invention relates to the above-mentioned compound, or a tautomer, stereoisomer, prodrug, crystal form, pharmaceutically acceptable salt, hydrate or solvate thereof, wherein $X_1$ is $CD_3$, $X_2$ is $CH_3$, and $R_1$-$R_4$ are each independently selected from hydrogen or deuterium.

In some embodiments of formula (II), formula (II-1), formula (II-2), formula (II-1a), formula (II-1b), formula (II-2a) and formula (II-2b), preferably, the present invention relates to the above-mentioned compound, or a tautomer, stereoisomer, prodrug, crystal form, pharmaceutically acceptable salt, hydrate or solvate thereof, wherein $X_1$ is $CD_3$, $X_2$ is $CH_3$, $R_3$ is hydrogen, and $R_1$, $R_2$ and $R_4$ are each independently selected from hydrogen or deuterium.

In some embodiments of formula (II), formula (II-1), formula (II-2), formula (II-1a), formula (II-1b), formula (II-2a) and formula (II-2b), preferably, the present invention relates to the above-mentioned compound, or a tautomer, stereoisomer, prodrug, crystal form, pharmaceutically acceptable salt, hydrate or solvate thereof, wherein $X_1$ is $CD_3$, $X_2$ is $CH_3$, $R_1$ and $R_2$ are hydrogen, and $R_3$ and $R_4$ are each independently selected from hydrogen or deuterium.

In some embodiments of formula (II), formula (II-1), formula (II-2), formula (II-1a), formula (II-1b), formula (II-2a) and formula (II-2b), preferably, the present invention relates to the above-mentioned compound, or a tautomer, stereoisomer, prodrug, crystal form, pharmaceutically acceptable salt, hydrate or solvate thereof, wherein $X_1$ is $CD_3$, $X_2$ is $CH_3$, $R_1$-$R_3$ are hydrogen, and $R_4$ is selected from hydrogen or deuterium.

In some embodiments of formula (II), formula (II-1), formula (II-2), formula (II-1a), formula (II-1b), formula (II-2a) and formula (II-2b), preferably, the present invention relates to the above-mentioned compound, or a tautomer, stereoisomer, prodrug, crystal form, pharmaceutically acceptable salt, hydrate or solvate thereof, wherein $X_1$ is $CD_3$, $R_4$ is hydrogen, $R_1$-$R_3$ are each independently selected from hydrogen or deuterium, and $X_2$ is selected from $CH_3$, $CD_3$, $CHD_2$, or $CH_2D$.

In some embodiments of formula (II), formula (II-1), formula (II-2), formula (II-1a), formula (II-1b), formula (II-2a) and formula (II-2b), preferably, the present invention relates to the above-mentioned compound, or a tautomer, stereoisomer, prodrug, crystal form, pharmaceutically acceptable salt, hydrate or solvate thereof, wherein $X_1$ is $CD_3$, $R_3$ and $R_4$ are hydrogen, $R_1$ and $R_2$ are each independently selected from hydrogen or deuterium, and $X_2$ is selected from $CH_3$, $CD_3$, $CHD_2$, or $CH_2D$.

In some embodiments of formula (II), formula (II-1), formula (II-2), formula (II-1a), formula (II-1b), formula (II-2a) and formula (II-2b), preferably, the present invention relates to the above-mentioned compound, or a tautomer, stereoisomer, prodrug, crystal form, pharmaceutically acceptable salt, hydrate or solvate thereof, wherein $X_1$ is $CD_3$, $R_1$, $R_2$ and $R_4$ are hydrogen, $R_3$ is selected from hydrogen or deuterium, and $X_2$ is selected from $CH_3$, $CD_3$, $CHD_2$ or $CH_2D$.

In some embodiments of formula (II), formula (II-1), formula (II-2), formula (II-1a), formula (II-1b), formula (II-2a) and formula (II-2b), preferably, the present invention relates to the above-mentioned compound, or a tautomer, stereoisomer, prodrug, crystal form, pharmaceutically acceptable salt, hydrate or solvate thereof, wherein $X_1$ is $CD_3$, $R_1$-$R_4$ are hydrogen, and $X_2$ is selected from $CH_3$, $CD_3$, $CHD_2$, or $CH_2D$.

In some embodiments of formula (II), formula (II-1), formula (II-2), formula (II-1a), formula (II-1b), formula (II-2a) and formula (II-2b), preferably, the present invention relates to the above-mentioned compound, or a tautomer, stereoisomer, prodrug, crystal form, pharmaceutically acceptable salt, hydrate or solvate thereof, wherein $X_1$ is $CD_3$, $R_4$ is hydrogen, $X_2$ is $CH_3$, and $R_1$-$R_3$ are each independently selected from hydrogen or deuterium.

In some embodiments of formula (II), formula (II-1), formula (II-2), formula (II-1a), formula (II-1b), formula (II-2a) and formula (II-2b), preferably, the present invention relates to the above-mentioned compound, or a tautomer, stereoisomer, prodrug, crystal form, pharmaceutically acceptable salt, hydrate or solvate thereof, wherein $X_1$ is $CD_3$, $R_3$ and $R_4$ are hydrogen, $X_2$ is $CH_3$, and $R_1$ and $R_2$ are each independently selected from hydrogen or deuterium.

In some embodiments of formula (II), formula (II-1), formula (II-2), formula (II-1a), formula (II-1b), formula (II-2a) and formula (II-2b), preferably, the present invention relates to the above-mentioned compound, or a tautomer, stereoisomer, prodrug, crystal form, pharmaceutically acceptable salt, hydrate or solvate thereof, wherein $X_1$ is $CD_3$, $R_1$, $R_2$, and $R_4$ are hydrogen, $X_2$ is $CH_3$, and $R_3$ is each independently selected from hydrogen or deuterium.

In some embodiments of formula (II), formula (II-1), formula (II-2), formula (II-1a), formula (II-1b), formula (II-2a) and formula (II-2b), preferably, the present invention relates to the above-mentioned compound, or a tautomer, stereoisomer, prodrug, crystal form, pharmaceutically acceptable salt, hydrate or solvate thereof, wherein $X_1$ is $CD_3$, $X_2$ is $CH_3$, and $R_1$-$R_4$ are hydrogen.

In some embodiments of formula (II), formula (II-1), formula (II-2), formula (II-1a), formula (II-1b), formula (II-2a) and formula (II-2b), preferably, the present invention relates to the above-mentioned compound, or a tautomer, stereoisomer, prodrug, crystal form, pharmaceutically acceptable salt, hydrate or solvate thereof, wherein X1 is CD3, R1-R4 are each independently selected from hydrogen or deuterium, X2 is selected from CH3, CD3, CHD2 or CH2D.

In some embodiments of formula (II), formula (II-1), formula (II-2), formula (II-1a), formula (II-1b), formula (II-2a) and formula (II-2b), preferably, the present invention relates to the above-mentioned compound, or a tautomer, stereoisomer, prodrug, crystal form, pharmaceutically acceptable salt, hydrate or solvate thereof, wherein X2 is CD3, R1-R4 are each independently selected from hydrogen or deuterium, X1 is selected from CH3, CD3, CHD2, or CH2D.

In some embodiments of formula (II), formula (II-1), formula (II-2), formula (II-1a), formula (II-1b), formula (II-2a) and formula (II-2b), preferably, the present invention relates to the above-mentioned compound, or a tautomer, stereoisomer, prodrug, crystal form, pharmaceutically acceptable salt, hydrate or solvate thereof, wherein X1 and X2 are CD3, R1-R4 are each independently selected from hydrogen or deuterium.

In some embodiments of formula (II), formula (II-1), formula (II-2), formula (II-1a), formula (II-1b), formula (II-2a) and formula (II-2b), preferably, the present invention relates to the above-mentioned compound, or a tautomer, stereoisomer, prodrug, crystal form, pharmaceutically acceptable salt, hydrate or solvate thereof, wherein $R_3$ is deuterium, $R_1$, $R_2$ and $R_4$ are each independently selected from hydrogen or deuterium, and $X_1$ and $X_2$ are each independently selected from $CH_3$, $CD_3$, $CHD_2$, or $CH_2D$.

In some embodiments of formula (II), formula (II-1), formula (II-2), formula (II-1a), formula (II-1b), formula (II-2a) and formula (II-2b), preferably, the present invention relates to the above-mentioned compound, or a tautomer, stereoisomer, prodrug, crystal form, pharmaceutically acceptable salt, hydrate or solvate thereof, wherein $R_3$ is deuterium, $X_1$ is $CD_3$, $R_1$, $R_2$, and $R_4$ are each independently selected from hydrogen or deuterium, and $X_2$ is selected from $CH_3$, $CD_3$, $CHD_2$, or $CH_2D$.

In some embodiments of formula (II), formula (II-1), formula (II-2), formula (II-1a), formula (II-1b), formula (II-2a) and formula (II-2b), preferably, the present invention relates to the above-mentioned compound, or a tautomer, stereoisomer, prodrug, crystal form, pharmaceutically acceptable salt, hydrate or solvate thereof, wherein $R_3$ is deuterium, $X_2$ is $CD_3$, $R_1$, $R_2$ and $R_4$ are each independently selected from hydrogen or deuterium, and $X_1$ is selected from $CH_3$, $CD_3$, $CHD_2$, or $CH_2D$.

In some embodiments of formula (II), formula (II-1), formula (II-2), formula (II-1a), formula (II-1b), formula (II-2a) and formula (II-2b), preferably, the present invention relates to the above-mentioned compound, or a tautomer, stereoisomer, prodrug, crystal form, pharmaceutically acceptable salt, hydrate or solvate thereof, wherein $R_3$ is deuterium, $X_1$ and $X_2$ are $CD_3$, and $R_1$, $R_2$ and $R_4$ are each independently selected from hydrogen or deuterium.

In some embodiments of formula (II), formula (II-1), formula (II-2), formula (II-1a), formula (II-1b), formula (II-2a) and formula (II-2b), preferably, the present invention relates to the above-mentioned compound, or a tautomer, stereoisomer, prodrug, crystal form, pharmaceutically acceptable salt, hydrate or solvate thereof, wherein $R_1$ and $R_2$ are deuterium, $R_3$ and $R_4$ are each independently selected from hydrogen or deuterium, and $X_1$ and $X_2$ are each independently selected from $CH_3$, $CD_3$, $CHD_2$, or $CH_2D$.

In some embodiments of formula (II), formula (II-1), formula (II-2), formula (II-1a), formula (II-1b), formula (II-2a) and formula (II-2b), preferably, the present invention relates to the above-mentioned compound, or a tautomer, stereoisomer, prodrug, crystal form, pharmaceutically acceptable salt, hydrate or solvate thereof, wherein $R_1$ and $R_2$ are deuterium, $X_1$ is $CD_3$, $R_3$ and $R_4$ are each independently selected from hydrogen or deuterium, and $X_2$ is selected from $CH_3$, $CD_3$, $CHD_2$ or $CH_2D$.

In some embodiments of formula (II), formula (II-1), formula (II-2), formula (II-1a), formula (II-1b), formula (II-2a) and formula (II-2b), preferably, the present invention relates to the above-mentioned compound, or a tautomer, stereoisomer, prodrug, crystal form, pharmaceutically acceptable salt, hydrate or solvate thereof, wherein $R_1$ and $R_2$ are deuterium, $X_2$ is $CD_3$, $R_3$ and $R_4$ are each independently selected from hydrogen or deuterium, and $X_1$ is selected from $CH_3$, $CD_3$, $CHD_2$ or $CH_2D$.

In some embodiments of formula (II), formula (II-1), formula (II-2), formula (II-1a), formula (II-1b), formula (II-2a) and formula (II-2b), preferably, the present invention relates to the above-mentioned compound, or a tautomer, stereoisomer, prodrug, crystal form, pharmaceutically acceptable salt, hydrate or solvate thereof, wherein $R_1$ and $R_2$ are deuterium, $X_1$ and $X_2$ are $CD_3$, and $R_3$ and $R_4$ are each independently selected from hydrogen or deuterium.

In some embodiments of formula (II), formula (II-1), formula (II-2), formula (II-1a), formula (II-1b), formula (II-2a) and formula (II-2b), preferably, the present invention relates to the above-mentioned compound, or a tautomer, stereoisomer, prodrug, crystal form, pharmaceutically acceptable salt, hydrate or solvate thereof, wherein $R_1$-$R_3$ are deuterium, $R_4$ is each independently selected from hydrogen or deuterium, and $X_1$ and $X_2$ are each independently selected from $CH_3$, $CD_3$, $CHD_2$, or $CH_2D$.

In some embodiments of formula (II), formula (II-1), formula (II-2), formula (II-1a), formula (II-1b), formula (II-2a) and formula (II-2b), preferably, the present invention relates to the above-mentioned compound, or a tautomer, stereoisomer, prodrug, crystal form, pharmaceutically acceptable salt, hydrate or solvate thereof, wherein $R_1$-$R_3$ are deuterium, $X_1$ is $CD_3$, $R_4$ is each independently selected from hydrogen or deuterium, and $X_2$ is selected from $CH_3$, $CD_3$, $CHD_2$, or $CH_2D$.

In some embodiments of formula (II), formula (II-1), formula (II-2), formula (II-1a), formula (II-1b), formula (II-2a) and formula (II-2b), preferably, the present invention relates to the above-mentioned compound, or a tautomer, stereoisomer, prodrug, crystal form, pharmaceutically acceptable salt, hydrate or solvate thereof, wherein $R_1$-$R_3$ are deuterium, $X_2$ is $CD_3$, $R_4$ is each independently selected from hydrogen or deuterium, and $X_1$ is selected from $CH_3$, $CD_3$, $CHD_2$, or $CH_2D$.

In some embodiments of formula (II), formula (II-1), formula (II-2), formula (II-1a), formula (II-1b), formula (II-2a) and formula (II-2b), preferably, the present invention relates to the above-mentioned compound, or a tautomer, stereoisomer, prodrug, crystal form, pharmaceutically acceptable salt, hydrate or solvate thereof, wherein $R_1$-$R_3$ are deuterium, $X_1$ and $X_2$ are $CD_3$, and $R_4$ is each independently selected from hydrogen or deuterium.

In some embodiments of formula (II), formula (II-1), formula (II-2), formula (II-1a), formula (II-1b), formula (II-2a) and formula (II-2b), preferably, the present invention relates to the above-mentioned compound, or a tautomer, stereoisomer, prodrug, crystal form, pharmaceutically acceptable salt, hydrate or solvate thereof, wherein $R_4$ is deuterium, $R_1$-$R_3$ are each independently selected from hydrogen or deuterium, and $X_1$ and $X_2$ are each independently selected from $CH_3$, $CD_3$, $CHD_2$, or $CH_2D$.

In some embodiments of formula (II), formula (II-1), formula (II-2), formula (II-1a), formula (II-1b), formula (II-2a) and formula (II-2b), preferably, the present invention relates to the above-mentioned compound, or a tautomer, stereoisomer, prodrug, crystal form, pharmaceutically acceptable salt, hydrate or solvate thereof, wherein $R_4$ is deuterium, $X_1$ is $CD_3$, $R_1$-$R_3$ are each independently selected from hydrogen or deuterium, and $X_2$ is selected from $CH_3$, $CD_3$, $CHD_2$, or $CH_2D$.

In some embodiments of formula (II), formula (II-1), formula (II-2), formula (II-1a), formula (II-1b), formula (II-2a) and formula (II-2b), preferably, the present invention relates to the above-mentioned compound, or a tautomer, stereoisomer, prodrug, crystal form, pharmaceutically acceptable salt, hydrate or solvate thereof, wherein $R_4$ is deuterium, $X_2$ is $CD_3$, $R_1$-$R_3$ are each independently selected from hydrogen or deuterium, and $X_1$ is selected from $CH_3$, $CD_3$, $CHD_2$, or $CH_2D$.

In some embodiments of formula (II), formula (II-1), formula (II-2), formula (II-1a), formula (II-1b), formula (II-2a) and formula (II-2b), preferably, the present invention relates to the above-mentioned compound, or a tautomer, stereoisomer, prodrug, crystal form, pharmaceutically acceptable salt, hydrate or solvate thereof, wherein $R_4$ is deuterium, $X_1$ and $X_2$ are $CD_3$, and $R_1$-$R_3$ are each independently selected from hydrogen or deuterium.

In some embodiments of formula (II), formula (II-1), formula (II-2), formula (II-1a), formula (II-1b), formula (II-2a) and formula (II-2b), preferably, the present invention relates to the above-mentioned compound, or a tautomer, stereoisomer, prodrug, crystal form, pharmaceutically acceptable salt, hydrate or solvate thereof, wherein $R_3$ and $R_4$ are deuterium, $R_1$ and $R_2$ are each independently selected from hydrogen or deuterium, and $X_1$ and $X_2$ are each independently selected from $CH_3$, $CD_3$, $CHD_2$, or $CH_2D$.

In some embodiments of formula (II), formula (II-1), formula (II-2), formula (II-1a), formula (II-1b), formula (II-2a) and formula (II-2b), preferably, the present invention relates to the above-mentioned compound, or a tautomer, stereoisomer, prodrug, crystal form, pharmaceutically acceptable salt, hydrate or solvate thereof, wherein $R_3$ and $R_4$ are deuterium, $X_1$ is $CD_3$, $R_1$ and $R_2$ are each independently selected from hydrogen or deuterium, and $X_2$ is selected from $CH_3$, $CD_3$, $CHD_2$ or $CH_2D$.

In some embodiments of formula (II), formula (II-1), formula (II-2), formula (II-1a), formula (II-1b), formula (II-2a) and formula (II-2b), preferably, the present invention relates to the above-mentioned compound, or a tautomer, stereoisomer, prodrug, crystal form, pharmaceutically acceptable salt, hydrate or solvate thereof, wherein $R_3$ and $R_4$ are deuterium, $X_2$ is $CD_3$, $R_1$ and $R_2$ are each independently selected from hydrogen or deuterium, and $X_1$ is selected from $CH_3$, $CD_3$, $CHD_2$ or $CH_2D$.

In some embodiments of formula (II), formula (II-1), formula (II-2), formula (II-1a), formula (II-1b), formula (II-2a) and formula (II-2b), preferably, the present invention relates to the above-mentioned compound, or a tautomer, stereoisomer, prodrug, crystal form, pharmaceutically acceptable salt, hydrate or solvate thereof, wherein $R_3$ and $R_4$ are deuterium, $X_1$ and $X_2$ are $CD_3$, and $R_1$ and $R_2$ are each independently selected from hydrogen or deuterium.

In some embodiments of formula (II), formula (II-1), formula (II-2), formula (II-1a), formula (II-1b), formula (II-2a) and formula (II-2b), preferably, the present invention relates to the above-mentioned compound, or a tautomer, stereoisomer, prodrug, crystal form, pharmaceutically acceptable salt, hydrate or solvate thereof, wherein $R_1$, $R_2$ and $R_4$ are deuterium, $R_3$ is selected from hydrogen or deuterium, and $X_1$ and $X_2$ are each independently selected from $CH_3$, $CD_3$, $CHD_2$, or $CH_2D$.

In some embodiments of formula (II), formula (II-1), formula (II-2), formula (II-1a), formula (II-1b), formula (II-2a) and formula (II-2b), preferably, the present invention relates to the above-mentioned compound, or a tautomer, stereoisomer, prodrug, crystal form, pharmaceutically acceptable salt, hydrate or solvate thereof, wherein $R_1$, $R_2$ and $R_4$ is deuterium, $X_1$ is $CD_3$, $R_3$ is selected from hydrogen or deuterium, and $X_2$ is selected from $CH_3$, $CD_3$, $CHD_2$ or $CH_2D$.

In some embodiments of formula (II), formula (II-1), formula (II-2), formula (II-1a), formula (II-1b), formula (II-2a) and formula (II-2b), preferably, the present invention relates to the above-mentioned compound, or a tautomer, stereoisomer, prodrug, crystal form, pharmaceutically acceptable salt, hydrate or solvate thereof, wherein $R_1$, $R_2$ and $R_4$ are deuterium, $X_2$ is $CD_3$, $R_3$ is selected from hydrogen or deuterium, and $X_1$ is selected from $CH_3$, $CD_3$, $CHD_2$ or $CH_2D$.

In some embodiments of formula (II), formula (II-1), formula (II-2), formula (II-1a), formula (II-1b), formula (II-2a) and formula (II-2b), preferably, the present invention relates to the above-mentioned compound, or a tautomer, stereoisomer, prodrug, crystal form, pharmaceutically acceptable salt, hydrate or solvate thereof, wherein $R_1$, $R_2$ and $R_4$ is deuterium, $X_1$ and $X_2$ are $CD_3$, and $R_3$ is selected from hydrogen or deuterium.

In some embodiments of formula (II), formula (II-1), formula (II-2), formula (II-1a), formula (II-1b), formula (II-2a) and formula (II-2b), preferably, the present invention relates to the above-mentioned compound, or a tautomer, stereoisomer, prodrug, crystal form, pharmaceutically acceptable salt, hydrate or solvate thereof, wherein $R_1$-$R_4$ are deuterium, and $X_1$ and $X_2$ are each independently selected from $CH_3$, $CD_3$, $CHD_2$, or $CH_2D$.

In some embodiments of formula (II), formula (II-1), formula (II-2), formula (II-1a), formula (II-1b), formula (II-2a) and formula (II-2b), preferably, the present invention relates to the above-mentioned compound, or a tautomer, stereoisomer, prodrug, crystal form, pharmaceutically acceptable salt, hydrate or solvate thereof, wherein $R_1$-$R_4$ are deuterium, $X_1$ is $CD_3$, $X_2$ is selected from $CH_3$, $CD_3$, $CHD_2$ or $CH_2D$.

In some embodiments of formula (II), formula (II-1), formula (II-2), formula (II-1a), formula (II-1b), formula (II-2a) and formula (II-2b), preferably, the present invention relates to the above-mentioned compound, or a tautomer, stereoisomer, prodrug, crystal form, pharmaceutically acceptable salt, hydrate or solvate thereof, wherein $R_1$-$R_4$ are deuterium, $X_2$ is $CD_3$, and $X_1$ is selected from $CH_3$, $CD_3$, $CHD_2$ or $CH_2D$.

In some embodiments of formula (II), formula (II-1), formula (II-2), formula (II-1a), formula (II-1b), formula (II-2a) and formula (II-2b), preferably, the present invention relates to the above-mentioned compound, or a tautomer, stereoisomer, prodrug, crystal form, pharmaceutically acceptable salt, hydrate or solvate thereof, wherein $R_1$-$R_4$ are deuterium, and $X_1$ and $X_2$ are $CD_3$.

As a preferred embodiment of the present invention, the compound is of any of the following structures, or a pharmaceutically acceptable salt thereof, but is not limited to the following structures:

29
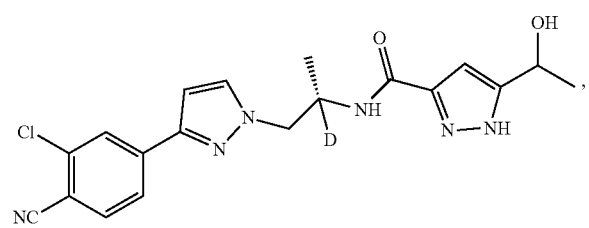
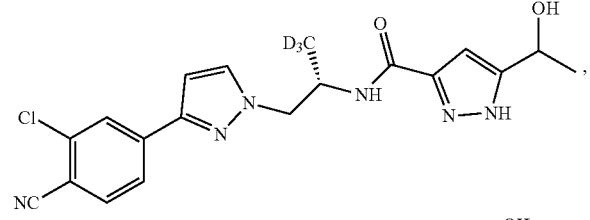
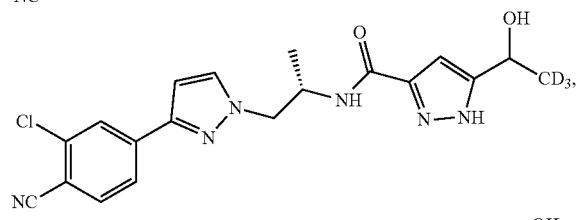
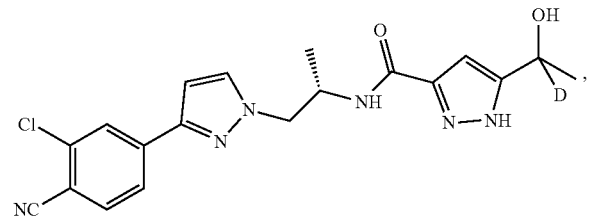
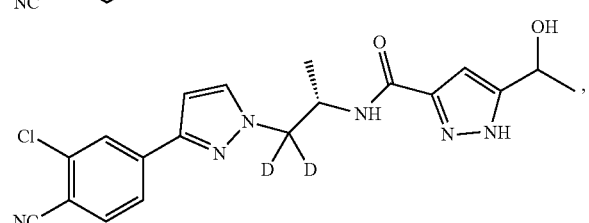
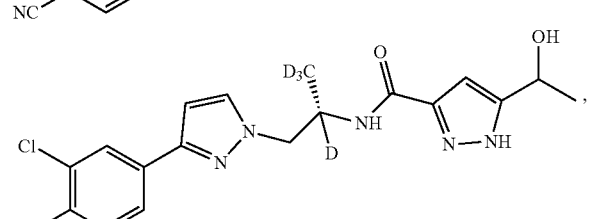
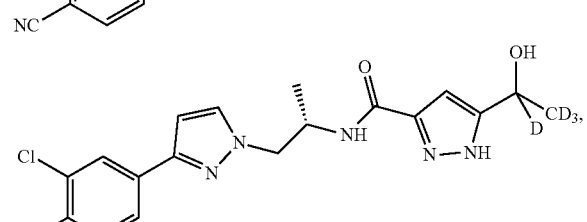
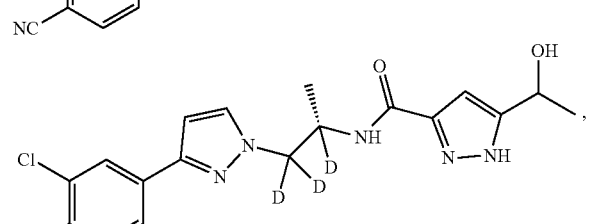
30
-continued
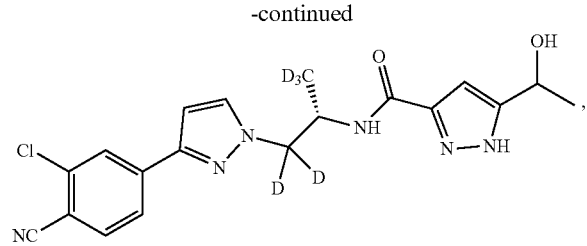
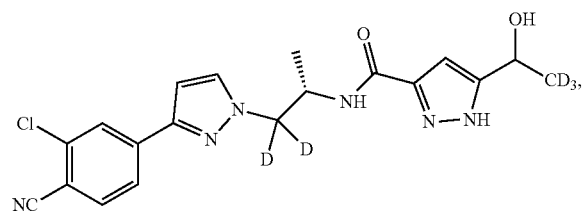
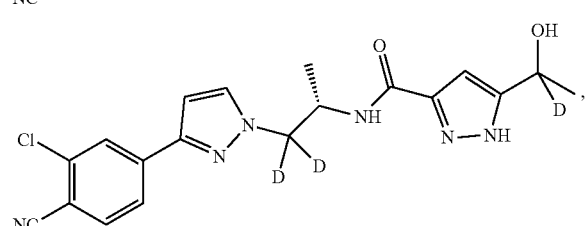
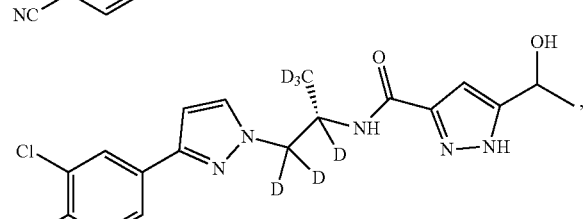
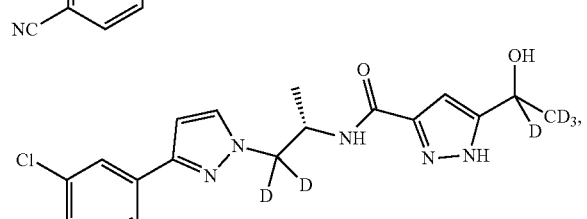
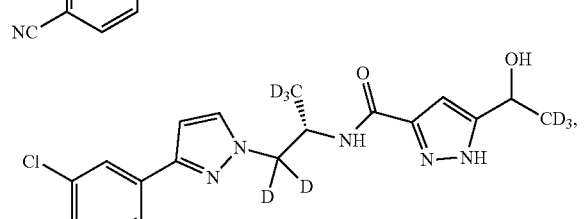
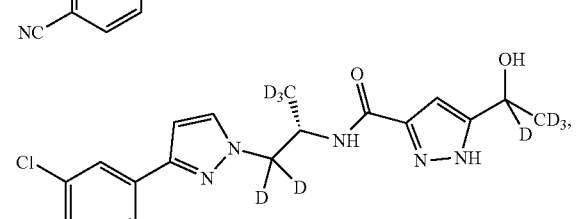
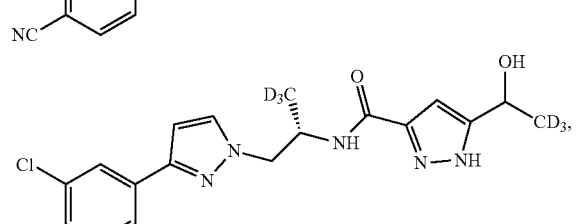

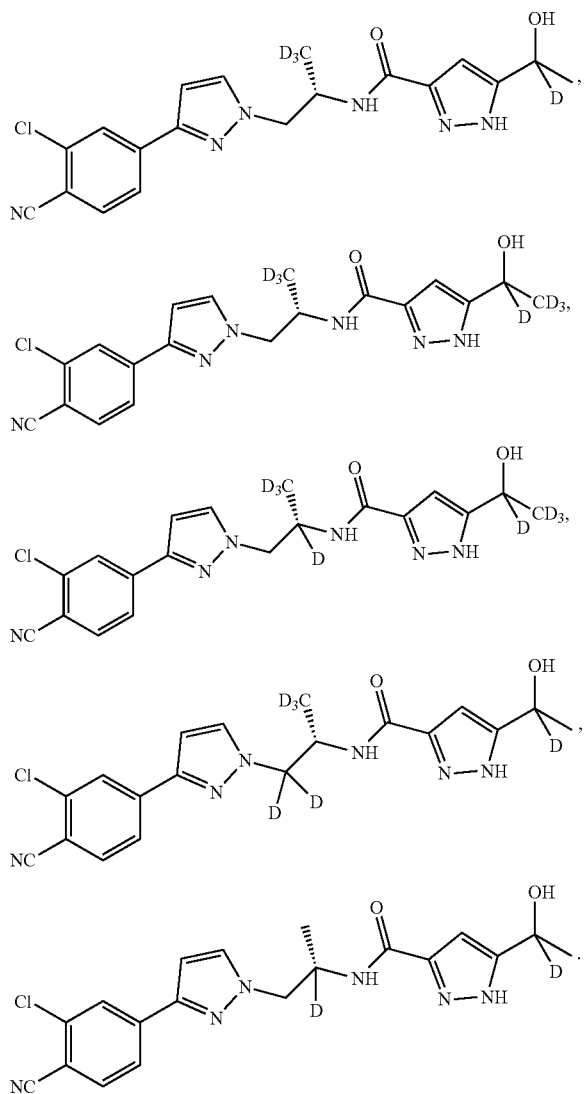

Tautomers: Since the hydrogen atom of the pyrazole ring can exist in a tautomeric equilibrium between the 1-position and the 2-position, those skilled in the art recognize that the formulas and chemical names as disclosed herein comprising the hydrogen atom in pyrazole comprise tautomers of the compounds. For example, the compound of formula (I):

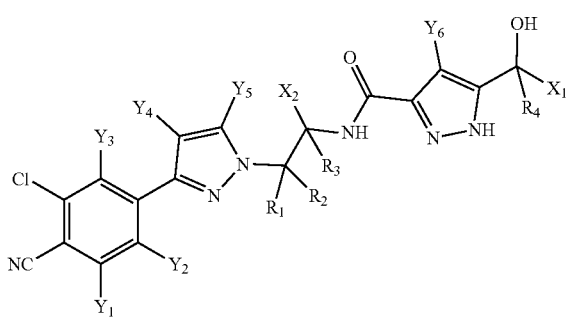

comprises the corresponding tautomer of the compound of formula (I):

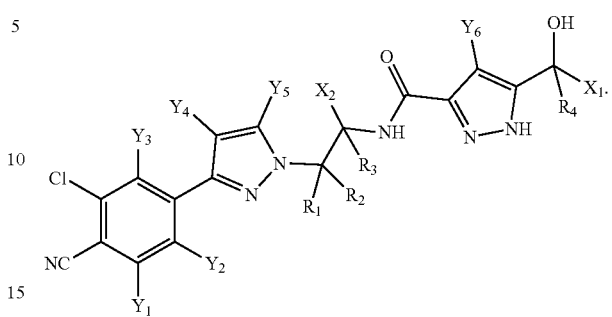

The compounds of the present invention may comprise one or more asymmetric centers, and therefore may exist in various stereoisomeric forms, for example, enantiomeric and/or diastereomeric forms. For example, the compounds of the present invention may be individual enantiomers, diastereomers or geometric isomers (such as cis and trans isomers), or may be in the form of mixtures of stereoisomers, including racemate mixtures and mixtures rich in one or more stereoisomers. An isomer can be separated from a mixture by a method known to those skilled in the art.

The method includes: chiral high pressure liquid chromatography (HPLC) and the formation and crystallization of chiral salts; or the preferred isomers can be prepared by asymmetric synthesis.

Those skilled in the art will understand that an organic compound can form a complex with a solvent, react in the solvent, or precipitate or crystallize out of the solvent. These complexes are called "solvates". When the solvent is water, the complex is called "hydrate". The present invention covers all solvates of the compounds of the present invention.

The term "solvate" refers to the form of a compound or a salt thereof combined with a solvent, usually formed by a solvolysis reaction. This physical association may include hydrogen bonding. Conventional solvents include water, methanol, ethanol, acetic acid, DMSO, THF, ether and the like. The compounds described herein can be prepared, for example, in crystalline forms, and can be solvated. Suitable solvates include pharmaceutically acceptable solvates and further include stoichiometric solvates and non-stoichiometric solvates. In some cases, the solvate will be able to be separated, for example, when one or more solvent molecules are incorporated into the crystal lattice of a crystalline solid. "Solvate" includes solvates in a solution state and isolatable solvates. Representative solvates include hydrates, ethanolates, and methanolates.

The term "hydrate" refers to a compound that is combined with water. Generally, the ratio of the number of water molecules contained in the hydrate of a compound to the number of molecules of the compound in the hydrate is definite. Therefore, the hydrate of a compound can be represented by, for example, the general formula $R \cdot x\, H_2O$, where R is the compound and x is a number greater than zero. A given compound can form more than one type of hydrate, including, for example, monohydrate (x is 1), lower hydrate (x is a number greater than 0 and less than 1, for example, hemihydrate ($R \cdot 0.5H_2O$)) and polyhydrate (x is a number greater than 1, for example, dihydrate ($R \cdot 2H_2O$) and hexahydrate ($R \cdot 6H_2O$)).

The compounds of the invention may be in amorphous or crystalline form (polymorphs). In addition, the compounds of the present invention may exist in one or more crystalline forms. Therefore, the present invention includes all amorphous or crystalline forms of the compounds of the present invention within its scope. The term "polymorph" refers to a crystalline form of a compound (or a salt, hydrate or solvate thereof) in a specific crystal packing arrangement. All polymorphs have the same elemental composition. Different crystalline forms usually have different X-ray diffraction patterns, infrared spectra, melting points, density, hardness, crystal shape, photoelectric properties, stability and solubility. Recrystallization solvent, crystallization rate, storage temperature and other factors can cause one crystalline form to dominate. Various polymorphs of a compound can be prepared by crystallization under different conditions.

The present invention also includes isotopically-labeled compounds, which are equivalent to those of the present invention, but have one or more atoms replaced by atoms whose atomic mass or mass number is different from the atomic mass or mass number common in nature. Examples of isotopes that can be introduced into the compounds of the present invention include isotopes of hydrogen, carbon, nitrogen, oxygen, phosphorus, sulfur, fluorine, and chlorine, such as $^2H$, $^3H$, $^{13}C$, $^{11}C$, $^{14}C$, $^{15}N$, $^{18}O$, $^{17}O$, $^{31}P$, $^{32}P$, $^{35}S$, $^{18}F$, and $^{36}Cl$, respectively. The compounds of the present invention containing the above isotopes and/or other isotopes of other atoms, their prodrugs, and pharmaceutically acceptable salts of the compounds or the prodrugs all fall within the scope of the present invention. Certain isotope-labeled compounds of the present invention, such as those incorporating radioisotopes (such as $^3H$ and $^{14}C$), can be used for drug and/or substrate tissue distribution determination. Tritium, i.e. $^3H$ and carbon-14, i.e. $^{14}C$ isotopes are particularly preferred, because they are easy to prepare and detect. Furthermore, substitution by heavier isotopes, such as deuterium, i.e. $^2H$, may provide therapeutic benefits due to higher metabolic stability, such as prolonged half-life in vivo or reduced dosage requirements, and may therefore be preferable in some cases. Isotope-labeled compounds of formula (I) of the present invention and their prodrugs can generally be prepared by replacing the non-isotope-labeled reagents with readily available isotope-labeled reagents when performing the processes disclosed in the following procedures and/or examples and preparation examples.

In addition, prodrugs are also included in the context of the present invention. The term "prodrug" as used herein refers to a compound that is converted into its active form with medical effects by, for example, hydrolysis in the blood in the body. Pharmaceutically acceptable prodrugs are described in T. Higuchi and V. Stella, Prodrugs as Novel Delivery Systems, A.C.S. Symposium Series, Vol. 14, Edward B. Roche, ed., Bioreversible Carriers in Drug Design, American Pharmaceutical Association and Pergamon Press, 1987, and D. Fleisher, S. Ramon, and H. Barbra "Improved oral drug delivery: solubility limitations overcome by the use of prodrugs", Advanced Drug Delivery Reviews (1996) 19(2) 115-130, each incorporated herein by reference.

A prodrug is any covalently bonded compound of the invention. When such a prodrug is administered to a patient, it releases the parent compound in the body. Prodrugs are usually prepared by modifying functional groups, and the modification is performed in such a way that the parent compound can be produced by conventional operations or cleavage in vivo. Prodrugs include, for example, the compounds of the present invention in which a hydroxyl, amino, or sulfhydryl group is bonded to any group, which can be cleaved to form the hydroxyl, amino, or sulfhydryl group when administered to a patient. Therefore, representative examples of prodrugs include, but are not limited to, acetate/acetamide, formate/formamide, and benzoate/benzamide derivatives of the hydroxyl, sulfhydryl, and amino functional groups of the compounds of formula (I). In addition, in the case of carboxylic acid (—COOH), esters such as methyl esters, ethyl esters and the like can be used. The ester itself can be active and/or can be hydrolyzed in vivo. Suitable pharmaceutically acceptable ester groups hydrolyzable in vivo include those groups that are easily decomposed in the human body to release the parent acid or salt thereof.

Methods of Preparing the Compounds of the Present Invention

The compounds of the present invention (including their salts) can be prepared using known organic synthesis techniques, and can be synthesized according to any of a variety of possible synthetic routes, such as those in the schemes below. The reaction for preparing the compound of the present invention can be carried out in a suitable solvent, and those skilled in the art of organic synthesis can easily select the solvent. A suitable solvent may be substantially non-reactive with the starting material (reactant), intermediate or product at the temperature at which the reaction proceeds (for example, a temperature in the range from the freezing temperature of the solvent to the boiling point of the solvent). The intended reaction can be carried out in one solvent or a mixture of more than one solvent. The skilled person can select the solvent used in a specific reaction step according to the specific reaction step.

The preparation of the compounds of the present invention may involve the protection and deprotection of different chemical groups. Those skilled in the art can easily determine whether protection and deprotection are required and select an appropriate protecting group. For the chemical properties of the protecting groups, see, for example, Wuts and Greene, Protective Groups in Organic Synthesis, 4th edition, John Wiley & Sons: New Jersey, (2006), which is incorporated herein by reference in its entirety.

The compound of the present invention can be prepared as individual stereoisomers by reacting a racemic mixture of the compound with an optically active resolving agent to form a pair of diastereomeric compounds, separating the diastereomers and recovering the optically pure enantiomers. Resolution of enantiomers can be carried out using diastereomeric derivatives of the compounds of the present invention, preferably dissociable complexes (for example, crystalline diastereomeric salts). Diastereomers have significantly different physical properties (for example, melting point, boiling point, solubility, reactivity, etc.), and can be easily separated by virtue of the dissimilarity. Diastereomers can be separated by chromatography, preferably by separation/resolution techniques based on difference in solubility. Then the optically pure enantiomers are recovered by any practical means without racemization, together with the resolution reagents. A more detailed description of the techniques applicable to the resolution of a racemic mixture to obtain stereoisomers of compounds can be found in Jean Jacques, Andre Collet, Samuel H. Wilen, "Enantiomers, Racemates and Resolutions", John Wiley And Sons, Inc., 1981.

The reaction can be monitored according to any suitable method known in the art. For example, spectroscopic means (such as nuclear magnetic resonance (NMR) spectroscopy (for example, $^1H$ or $^{13}C$), infrared (IR) spectroscopy, spectrophotometry (for example, UV-vis), mass spectrometry (MS)) or chromatographic methods such as high performance liquid chromatography (HPLC) or thin layer chromatography (TLC) can be used to monitor product formation.

Pharmaceutical Compositions, Preparations and Kits

In another aspect, the invention provides a pharmaceutical composition comprising a compound of the invention (also referred to as an "active ingredient") and a pharmaceutically acceptable excipient. In some embodiments, the pharmaceutical composition comprises an effective amount of active ingredient. In some embodiments, the pharmaceutical composition comprises a therapeutically effective amount of the active ingredient. In some embodiments, the pharmaceutical composition comprises a prophylactically effective amount of the active ingredient.

The pharmaceutically acceptable excipient used in the present invention refers to a non-toxic carrier, adjuvant or vehicle that does not damage the pharmacological activity of the compound formulated together. Pharmaceutically acceptable carriers, adjuvants or vehicles that can be used in the composition of the present invention include, but are not limited to, ion exchangers, alumina, aluminum stearate, lecithin, serum proteins (such as human serum albumin), buffer substances (such as phosphate), glycine, sorbic acid, potassium sorbate, partial glyceride mixtures of saturated plant fatty acids, water, salts or electrolytes (such as protamine sulfate), disodium hydrogen phosphate, potassium hydrogen phosphate, sodium chloride, zinc salt, silica gel, magnesium trisilicate, polyvinylpyrrolidone, cellulose-based substances, polyethylene glycol, sodium carboxymethyl cellulose, polyacrylate, wax, polyethylene-polyoxypropylene block polymers, polyethylene glycol and lanolin.

The present invention also includes kits (e.g., pharmaceutical packaging). The kit provided may include the compound of the present invention, other therapeutic agents, and the first and second containers (for example, vials, ampoules, bottles, syringes, and/or dispersible packaging or other suitable containers) containing the compound of the present invention and the other therapeutic agents. In some embodiments, the kit provided may also optionally include a third container, which contains pharmaceutical excipients for diluting or suspending the compound of the present invention and/or other therapeutic agents. In some embodiments, the compound of the present invention and the other therapeutic agent provided in the first container and the second container are combined to form a unit dosage form.

The pharmaceutical composition provided by the present invention can be administered by many routes, including but not limited to: oral administration, parenteral administration, inhalation administration, topical administration, rectal administration, nasal administration, buccal administration, vaginal administration, administration via implants or other modes of administration. For example, parenteral administration as used herein includes subcutaneous administration, intradermal administration, intravenous administration, intramuscular administration, intraarticular administration, intraarterial administration, intrasynovial administration, intrasternal administration, intracerebrospinal administration, intralesional administration, and intracranial injection or infusion technology.

Generally, an effective amount of a compound provided herein is administered. According to relevant circumstances, including the condition being treated, the route of administration selected, the compound actually administered, the age, weight and response of the individual patient, the severity of the patient's symptoms, etc., the amount of the compound actually administered can be determined by a doctor.

When used to prevent the condition of the present invention, the compound provided herein is administered to a subject at risk of developing the condition, typically based on the doctor's advice and under the supervision of the doctor, at the dosage level as described above. Subjects at risk of developing a specific condition generally include subjects with a family history of the condition, or those subjects who are particularly sensitive to the formation of the condition as determined by genetic testing or screening.

The pharmaceutical compositions provided herein can also be administered chronically ("long-term administration"). Long-term administration refers to the administration of the compound or its pharmaceutical composition over a long period of time, for example, 3 months, 6 months, 1 year, 2 years, 3 years, 5 years, etc., or the administration can be continued indefinitely, for example, for the rest of the subject's life. In some embodiments, long-term administration is intended to provide a constant level of the compound, for example, within a therapeutic window, in the blood over a long period of time.

Various administration methods can be used to further deliver the pharmaceutical composition of the present invention. For example, in some embodiments, the pharmaceutical composition may be administered by bolus injection, for example, in order to rapidly increase the concentration of the compound in the blood to an effective level. The bolus dose depends on the target systemic level of the active ingredient. For example, an intramuscular or subcutaneous bolus dose releases the active ingredient slowly, while a bolus injection delivered directly into a vein (for example, by IV infusion) allows a more rapid delivery to rapidly increase the concentration of the active ingredient in the blood to an effective level. In other embodiments, the pharmaceutical composition may be administered in the form of a continuous infusion, for example, by IV infusion, so as to provide a steady concentration of the active ingredient in the subject's body. Furthermore, in other embodiments, a bolus dose of the pharmaceutical composition may be administered first, followed by continuous infusion.

Oral compositions can take the form of bulk liquid solutions or suspensions or bulk powders. However, more generally, in order to facilitate precise dosing, the composition is provided in unit dosage forms. The term "unit dosage form" refers to a physically discrete unit suitable as a unit dose for human patients and other mammals, each unit containing a predetermined amount of active substance suitable for producing the desired therapeutic effect and suitable pharmaceutical excipients. Typical unit dosage forms include pre-filled, pre-measured ampoules or syringes of liquid compositions, or pills, tablets, capsules, etc. in the case of solid compositions. In this composition, the compound is usually a minor component (in about 0.1 to about 50% by weight, or preferably about 1 to about 40% by weight), and the remainder is various carriers or excipients and processing aids useful for forming the desired administration form.

For oral doses, the representative regimen is one to five oral doses per day, especially two to four oral doses, typically three oral doses. Using these dosing modes, each dose provides about 0.01 to about 20 mg/kg of the compound of the present invention, with preferred doses each providing about 0.1 to about 10 mg/kg, especially about 1 to about 5 mg/kg.

In order to provide a blood level similar to or lower than the injected dose, the transdermal dose is usually selected in an amount of about 0.01 to about 20% by weight, preferably about 0.1 to about 20% by weight, and preferably about 0.1 to about 10% by weight, and more preferably about 0.5 to about 15% by weight.

From about 1 to about 120 hours, especially 24 to 96 hours, the injection dose level is in the range of about 0.1 mg/kg/hour to at least 10 mg/kg/hour. In order to obtain a sufficient steady level, a preload bolus of about 0.1 mg/kg to about 10 mg/kg or more can also be administered. For human patients of 40 to 80 kg, the maximum total dose cannot exceed approximately 2 g/day.

Liquid forms suitable for oral administration may include suitable aqueous or non-aqueous carriers as well as buffers, suspending and dispersing agents, coloring agents, flavoring agents, and the like. The solid form may include, for example, any of the following components, or compounds with similar properties: binders, for example, microcrystalline cellulose, tragacanth, or gelatin; excipients, for example, starch or lactose, disintegrants, for example, alginic acid, Primogel or corn starch; lubricants, for example, magnesium stearate; glidants, for example, colloidal silicon dioxide; sweeteners, for example, sucrose or saccharin; or flavoring agents, for example, mint, methyl salicylate or orange flavoring agent.

Injectable compositions are typically based on injectable sterile saline or phosphate buffered saline, or other injectable excipients known in the art. As mentioned earlier, in such compositions, the active compound is typically a minor component, often of about 0.05 to 10% by weight, with the remainder being injectable excipients and the like.

The transdermal composition is typically formulated as a topical ointment or cream containing the active ingredients. When formulated as an ointment, the active ingredient is typically combined with paraffin or a water-miscible ointment base. Alternatively, the active ingredient can be formulated as a cream with, for example, an oil-in-water cream base. Such transdermal formulations are well known in the art, and generally include other components for enhancing stable skin penetration of the active ingredient or the formulation. All such known transdermal formulations and components are included within the scope provided by the present invention.

The compounds of the present invention can also be administered via transdermal devices. Therefore, transdermal administration can be achieved using a reservoir or porous membrane type, or a variety of solid matrix patches.

The above-mentioned components of the composition for oral administration, injection or topical administration are only representative. Other materials and processing technologies are described in Part 8 in Remington's Pharmaceutical Sciences, 17th edition, 1985, Mack Publishing Company, Easton, Pennsylvania, which is incorporated herein by reference.

The compounds of the present invention can also be administered in a sustained release form or from a sustained release drug delivery system. A description of representative sustained-release materials can be found in Remington's Pharmaceutical Sciences.

The invention also relates to pharmaceutically acceptable formulations of the compounds of the invention. In one embodiment, the formulation contains water. In another embodiment, the formulation comprises a cyclodextrin derivative. The most common cyclodextrins are α-, β- and γ-cyclodextrins composed of 6, 7 and 8 α-1,4-linked glucose units, respectively, which optionally include one or more substituents on the linked sugar moieties, including but not limited to: methylated, hydroxyalkylated, acylated, and sulfoalkyl ether substituted. In some embodiments, the cyclodextrin is a sulfoalkyl ether β-cyclodextrin, for example, sulfobutyl ether β-cyclodextrin, also known as Captisol. See, for example, U.S. Pat. No. 5,376,645. In some embodiments, the formulation comprises hexapropyl-β-cyclodextrin (e.g., 10-50% in water).

Indications

The present invention encompasses a method for treating and/or preventing androgen receptor (AR) dependent diseases, including administering to a subject a therapeutically effective amount of a compound as defined by formula (I), formula (I-1), formula (I-2), formula (I-1a), formula (I-1b), formula (I-2a), formula (I-2b), formula (II), formula (II-1), formula (II-2), formula (II-1a), formula (II-1b), formula (II-2a) or formula (II-2b). The androgen receptor-dependent disease is cancer. The cancer is selected from: prostate cancer (PCa), breast cancer (such as triple negative breast cancer (TNBC)), testicular cancer, cancers related to partial androgen insensitivity syndrome (PAIS) (such as gonadal tumors and seminoma), uterine cancer, ovarian cancer, fallopian tube cancer or peritoneal cancer, salivary gland cancer, bladder cancer, genitourinary system cancer, brain cancer, skin cancer, lymphoma, mantle cell lymphoma, liver cancer, hepatocellular carcinoma, kidney cancer, renal cell carcinoma, osteosarcoma, pancreatic cancer, endometrial cancer, lung cancer, non-small cell lung cancer, gastric cancer, colon cancer, perianal adenoma, or central nervous system cancer. In another embodiment, the breast cancer is triple negative breast cancer (TNBC).

The present invention encompasses a method for treating prostate cancer (PCa) in a male subject in need thereof or increasing the survival period of the subject, including administering to the subject a therapeutically effective amount of a compound as defined by formula (I), formula (I-1), formula (I-2), formula (I-1a), formula (I-1b), formula (I-2a), formula (I-2b), formula (II), formula (II-1), formula (II-2), formula (II-1a), formula (II-1b), formula (II-2a) or formula (II-2b). Prostate cancer includes, but is not limited to, advanced prostate cancer, castration resistant prostate cancer (CRPC), metastatic CRPC (mCRPC), non-metastatic CRPC (nmCRPC), high-risk nmCRPC, or any combination thereof. Another embodiment of the present invention encompasses a method further comprising administering androgen deprivation therapy (ADT). Alternatively, the method may treat prostate cancers that are resistant to treatment with a known androgen receptor antagonist or ADT, or other AR antagonist-resistant cancers, wherein the androgen receptor antagonist is at least one of the following: enzalutamide, bicalutamide, abiraterone, ARN-509, ODM-201, EPI-001, EPI-506, AZD-3514, galeterone, ASCJ-9, flutamide, hydroxyflutamide, nilutamide, cyproterone acetate, ketoconazole or spironolactone.

The normal level of prostate specific antigen (PSA) depends on several factors, such as age and prostate size of a male subject. PSA levels between 2.5 and 10 ng/mL are considered "critically high", while levels above 10 ng/mL are considered "high". A rate change or "PSA rate" of greater than 0.75/year is considered high. Despite persistent ADT or ADT history, surgical castration, or treatment with antiandrogens and/or LHRH agonists, PSA levels may still increase.

Patients at high risk of progression to castration-resistant prostate cancer (CRPC) comprise men with advanced prostate cancer who undergo androgen deprivation therapy (ADT) and have a serum total testosterone concentration greater than 20 ng/dL, or men with advanced prostate cancer who have any of the following when starting ADT: (1) prostate cancer with Confirmed Gleason pattern 4 or 5; (2) metastatic prostate cancer; (3) PSA doubling time <3 months; (4) PSA≥20 ng/dL; or (5) PSA recurrence <3 years after confirmed local therapy (radical prostatectomy or radiotherapy).

Men at high risk of non-metastatic castration-resistant prostate cancer (high-risk nmCRPC) may include those with a rapid PSA doubling time, who have an expected progression-free survival period of about 18 months or less.

The method of the present invention can treat a subject with a PSA level greater than 8 ng/mL, where the subject suffers from high-risk nmCRPC. The patient population includes subjects with nmCRPC, where PSA doubles in less than 8 months or less than 10 months. The method can also treat a patient population having total serum testosterone levels greater than 20 ng/mL in subjects with high-risk nmCRPC. In one instance, serum-free testosterone levels are greater than the serum-free testosterone levels observed in orchiectomy male subjects with high-risk nmCRPC.

The pharmaceutical composition of the present invention may further include at least one anti-androgen, anti-apoptotic receptor 1 (anti-PD-1) drug or anti-PD-L1 drug. Anti-androgens include (but are not limited to) bicalutamide, flutamide, finasteride, dutasteride, enzalutamide, nilutamide, chlordigesterone, abiraterone, or any combination thereof. Anti-PD-1 drugs include (but are not limited to) AMP-224, nivolumab, pembrolizumab, pidilizumab, and AMP-554. Anti-PD-L1 drugs include (but are not limited to) BMS-936559, atezolizumab, durvalumab, avelumab and MPDL3280. Anti-CTLA-4 drugs include (but are not limited to) ipilimumab and tremelimumab.

The treatment of prostate cancer, advanced prostate cancer, CRPC, mCRPC, and/or nmCRPC can cause clinically meaningful improvements in prostate cancer-related symptoms, function, and/or survival. If the cancer is metastatic, then a clinically meaningful improvement can be determined by increasing the radiation progression-free survival (rPFS), or if the cancer is non-metastatic, then by increasing the metastasis-free survival (MFS), and so on.

The present invention encompasses a method for reducing serum prostate-specific antigen (PSA) levels in male subjects suffering from prostate cancer, advanced prostate cancer, CRPC, mCRPC and/or nmCRPC, including administering a therapeutically effective amount of AR antagonistic compound, wherein the compound is represented by a structure of formula (I), formula (I-1), formula (I-2), formula (I-1a), formula (I-1b), formula (I-2a), formula (I-2b), formula (II), formula (II-1), formula (II-2), formula (II-1a), formula (II-1b), formula (II-2a) or formula (II-2b).

The present invention encompasses a method of adjuvant hormone therapy for reducing serum PSA in male subjects suffering from CRPC, comprising administering a therapeutically effective amount of a compound of formula (I), formula (I-1), formula (I-2), formula (I-1a), formula (I-1b), formula (I-2a), formula (I-2b), formula (II), formula (II-1), formula (II-2), formula (II-1a), formula (II-1b), formula (II-2a) or formula (II-2b) for reducing serum PSA in male subjects suffering from CRPC.

The method can increase rPFS or MFS.

The subject may have non-metastatic cancer, have got failed androgen deprivation therapy (ADT), have undergone orchiectomy, or have a high or increased PSA level; and the subject may have prostate cancer, advanced prostate cancer, refractory prostate cancer, CRPC, mCRPC, or nmCRPC. In these subjects, the refractory prostate cancer may be enzalutamide-resistant prostate cancer. In these subjects, nmCRPC may be a high-risk nmCRPC. In addition, subjects can undergo androgen deprivation therapy (ADT) with or without castration levels of total T.

As used herein, the phrase "subject with castration-resistant prostate cancer" refers to a subject who has at least one of the following characteristics: having been previously treated with androgen deprivation therapy (ADT); being responsive to ADT and having the current serum PSA>2 ng/mL, or having the current serum PSA>2 ng/mL and representing a 25% increase higher than the lowest point obtained by ADT; still being diagnosed with serum PSA progression, despite androgen deprivation therapy; and having a castration level of <50 ng/dL of serum total testosterone, or a castration level of <20 ng/dL of serum total testosterone. The subject may have elevated serum PSA in two consecutive assessments at least 2 weeks apart; be effectively treated with ADT; or have a history of serum PSA response after starting ADT.

As used herein, the term "serum PSA progression" refers to an increase in serum PSA by 25% or more and an absolute increase of 2 ng/mL or more from the lowest point; or serum PSA greater than 2 ng/mL after starting androgen deprivation therapy (ADT), or PSA greater than 2 ng/mL and a 25% increase higher than the lowest point obtained by ADT. The term "lowest point" refers to the lowest PSA level when a patient undergoes ADT.

The term "serum PSA response" refers to at least one of the following: at least a 90% reduction in the serum PSA value before the start of ADT; an undetectable level of serum PSA<10 ng/mL at any time (<2 ng/mL); a decrease of at least 50% in serum PSA from baseline; a decrease of at least 40% in serum PSA from baseline; a decrease of at least 30% in serum PSA from baseline; or a decrease of at least 10% in serum PSA from baseline.

The term "advanced prostate cancer" refers to a metastatic cancer that originates in the prostate and has extensively metastasized beyond the prostate to such as surrounding tissues, including seminal vesicles, pelvic lymph nodes or bones, or other parts of the body. Prostate cancer lesions are graded by Gleason grades of 1 to 5 with increasing malignancy. Patients with a significant risk of progressive disease and/or death of prostate disease should be included in the definition, and any patients with cancer outside the prostate capsule with a disease stage as low as IIB clearly have "advanced" disease. "Advanced prostate cancer" can refer to locally advanced prostate cancer.

The term "refractory" can refer to cancers that do not respond to treatment. For example, prostate cancer may be resistant at the beginning of treatment or it may become resistant during treatment. "Refractory cancer" may also be referred to as "resistant cancer" herein.

The term "castration-resistant prostate cancer" (CRPC) refers to advanced prostate cancer that is getting worse or progressing when the patient maintains ADT or other therapies to reduce testosterone, or prostate cancer that is considered hormone refractory, hormone resting, androgen independent or resistant to chemical or surgical castration. CRPC may be the result of AR activation through endocrine androgen synthesis, expression of AR splice variants (AR-SV) without ligand binding domain (LBD), or expression of AR-LBD or other AR mutations that have the potential to resist antagonists. CRPC is an advanced prostate cancer that is still developing despite the ongoing ADT and/or surgical castration. CRPC is defined as prostate cancer that continues to progress or worsen or adversely affect the patient's health despite previous surgical castration and the continuous treatment with gonadotropin-releasing hormone agonists (e.g., leuprolide) or antagonists (e.g., degarelix or abarelix), anti-androgen, chemical agents or other prostate cancer therapies, as evidenced by increased or higher serum levels of PSA, cancer metastasis, bone cancer metastasis, pain, lymph node involvement, increased size or serum markers of tumor growth, prognostic diagnostic markers of worsening, or patient condition.

The term "androgen deprivation therapy (ADT)" may include orchiectomy; administration of luteinizing hormone releasing hormone (LHRH) analogs; administration of luteinizing hormone releasing hormone antagonists; administration of 5-reductase inhibitors; administration of antiandrogens; administration of testosterone biosynthesis inhibitors; administration of estrogen; administration of 17α-hydroxylase/C17,20 lyase (CYP17A1) inhibitors. LHRH drugs reduce the amount of testosterone produced by the testicles.

The present invention encompasses a method of treating anti-androgen resistant prostate cancer. Antiandrogens may include, but are not limited to, bicalutamide, hydroxyflutamide, flutamide, enzalutamide, or abiraterone.

EXAMPLE

The present invention will be further illustrated below in conjunction with specific examples. It should be understood that these examples are only used to illustrate the present invention and not to limit the scope of the present invention. The experimental methods that do not indicate specific conditions in the following examples usually follow the conventional conditions or the conditions suggested by the manufacturer. Unless otherwise specified, parts and percentages are parts by weight and percentages by weight.

The abbreviations used herein have the following meanings:

| | |
|---|---|
| DIAD | diisopropyl azodicarboxylate |
| EDCI | 1-ethyl-(3-dimethylaminopropyl)carbodiimide hydrochloride |
| HBTU | benzotriazol-N,N,N',N'-tetramethyluronium hexafluorophosphate |
| EDTA | ethylenediamine tetraacetic acid |
| DTT | dithiothreitol |
| Pd(OAc)$_2$ | palladium acetate |
| PPh$_3$ | triphenylphosphine |
| Boc | t-butoxycarbonyl |
| NaH | potassium hydride |
| K$_2$CO$_3$ | potassium carbonate |
| NaBH$_4$ | sodium borohydride |
| DIPEA | N,N-diisopropylethylamine |
| HCl | hydrochloric acid |
| ACN | acetonitrile |
| MeOH | methanol |
| EA | ethyl acetate |
| PE | petroleum ether |
| THF | tetrahydrofuran |
| DCM | dichloromethane |
| DMF | N,N-dimethylformamide |
| DMSO | dimethyl sulfoxide |
| Dioxane | 1,4-dioxane |
| CDCl$_3$ | deuterated chloroform |

Preparation of Intermediate A1 (S)-4-O-(2-aminopropyl)-1H-pyrazol-3-yl)-2-chlorobenzonitrile

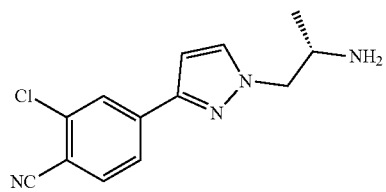

The following synthetic route was used.

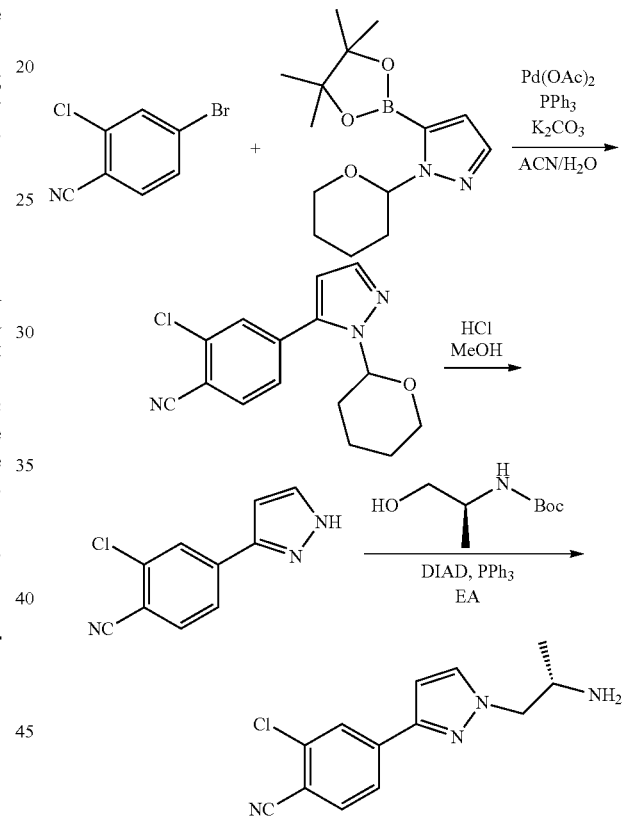

Step 1: Synthesis of Compound 2-chloro-4-(1-(tetrahydro-2H-pyran-2-yl)-1H-pyrazol-5-yl)benzonitrile Under nitrogen protection, Pd(OAc)$_2$ (400 mg) and PPh$_3$ (800 mg) were added to a mixture of 4-bromo-2-chlorobenzonitrile (14.0 g, 65.1 mmol), 1-(tetrahydro-2H-pyran-2-yl)-5-(4,4,5,5-tetramethyl-1,3,2-dioxaborolan-2-yl)-1H-pyrazole (21.0 g, 76.2 mmol) and potassium carbonate (18.6 g, 135 mmol) in acetonitrile (50 mL) and water (50 mL) at room temperature. The reaction was stirred at 60-70° C. for 3.5 h. The aqueous layer was separated while it was hot. The organic layer was added with 25% ammonia (2 mL), cooled to room temperature, and slowly added with water (80 mL). The reaction was stirred overnight. The solid was filtered out, washed with acetonitrile and water (20 mL, 1:1), and vacuum dried to yield 17.8 g of off-white solid. Yield: 95.6%. LC-MS (APCI): m/z=288.1 (M+1)$^+$.

Step 2: Synthesis of Compound 2-chloro-4-(1H-pyrazol-3-yl)benzonitrile

At 10±3° C., concentrated hydrochloric acid (0.54 mL) was added to a solution of 2-chloro-4-(1-(tetrahydro-2H-pyran-2-yl)-1H-pyrazol-5-yl)benzonitrile (17.8 g) in methanol (70 mL), and the reaction was stirred at 10±3° C. for 2.5 h. The reaction was added with ammonia (25%, 3 mL) and then water (20 mL), stirred overnight at room temperature and then stirred at 0-5° C. for 4 h. The solid was filtered out, washed with cold water and methanol (3:1, 40 mL), and vacuum dried to obtain 9.8 g of off-white solid. Yield: 78%. LC-MS (APCI): m/z=204.1 (M+1)$^+$.

Step 3: Synthesis of Intermediate A1

At 10±5° C., DIAD (2.97 mL, 14.8 mmol) was slowly added dropwise to a solution of 2-chloro-4-(1H-pyrazol-3-yl)benzonitrile (1.5 g, 7.4 mmol), N-Boc-L-alaninol (2.65 g, 14.8 mmol) and PPh$_3$ (3.96 g, 14.8 mmol) in anhydrous ethyl acetate (20 mL) under nitrogen protection. After the addition, the reaction was stirred overnight at room temperature. Concentrated hydrochloric acid (3.1 mL) was slowly added, with the temperature of the reaction system not exceeding 35° C. during the addition process. After the addition was complete, the reaction was carried out at 45±5° C. until the reaction was complete. The reaction was adjusted to alkaline pH with concentrated ammonia, extracted with DCM, and dried with anhydrous sodium sulfate. 1.5 g of white solid was obtained after filtration, concentration under reduced pressure, and purification of the concentrated liquid by column chromatography (DCM/MeOH=8%). Yield: 78%. LC-MS (APCI): m/z=261.2 (M+1)$^+$.

Preparation of Intermediate A2 (S)-4-(1-(2-amino-propyl-1,1-d$_2$)-1H-pyrazol-3-yl)-2-chlorobenzonitrile

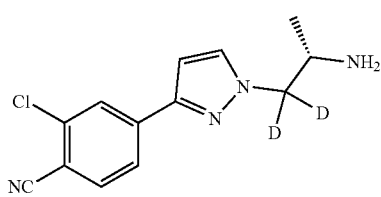

A2

The following synthetic route was used.

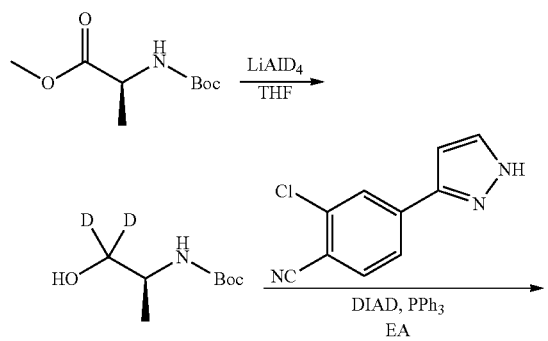

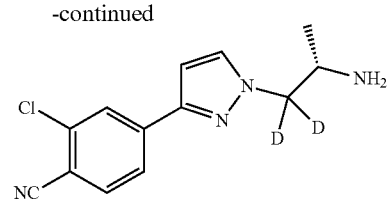

Step 1: Synthesis of Compound tert-butyl (S)-(1-hydroxyprop-2-yl-1,1-d$_2$)carbamate Under ice bath, LiAlD$_4$ (1.0 g, 23.8 mmol) was added in portions to Boc-L-alanine methyl ester (4.03 g, 19.8 mmol) in anhydrous THF (40 ml), and reacted at room temperature for 1 hr. It was quenched with NaSO$_4$.10H$_2$O, filtered, and washed twice with THF (30 mL×2), and the filtrate was rotation-dried to obtain 3.2 g of off-white solid. Yield: 91%. LC-MS (APCI): m/z=178.2 (M+1)$^+$, $^1$H NMR (500 MHz, CDCl$_3$) δ 4.66 (s, 1H), 3.77 (s, 1H), 2.61 (s, 1H), 1.45 (s, 9H), 1.15 (d, J=6.8 Hz, 3H).

Step 2: Synthesis of Intermediate A2

At 10±5° C., DIAD (2.97 mL, 14.8 mmol) was slowly added dropwise to a solution of 2-chloro-4-(1H-pyrazol-3-yl)benzonitrile (1.5 g, 7.4 mmol), tert-butyl (S)-(1-hydroxyprop-2-yl-1,1-d$_2$)carbamate (2.68 g, 14.8 mmol) and PPh$_3$ (3.96 g, 14.8 mmol) in anhydrous ethyl acetate (20 mL) under nitrogen protection. After the addition, the reaction was stirred overnight at room temperature. Concentrated hydrochloric acid (3.1 mL) was slowly added, with the temperature of the reaction system not exceeding 35° C. during the addition process. After the addition was complete, the reaction was carried out at 45±5° C. until the reaction was complete. The reaction was adjusted to alkaline pH with concentrated ammonia, extracted with DCM, and dried with anhydrous sodium sulfate. 1.52 g of white solid was obtained after filtration, concentration under reduced pressure, and purification of the concentrated liquid by column chromatography (DCM/MeOH=8%). Yield: 79%. LC-MS (APCI): m/z=263.2 (M+1)$^+$.

Preparation of Intermediate A3 (S)-4-(1-(2-amino-propyl-2-d)-1H-pyrazol-3-yl)-2-chlorobenzonitrile

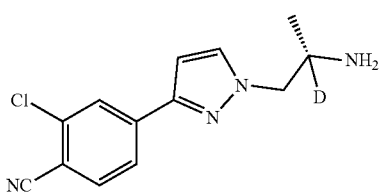

A3

The following synthetic route was used.

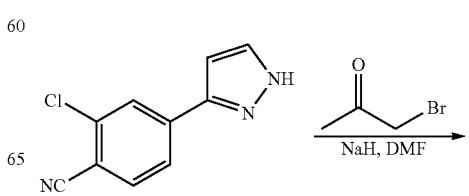

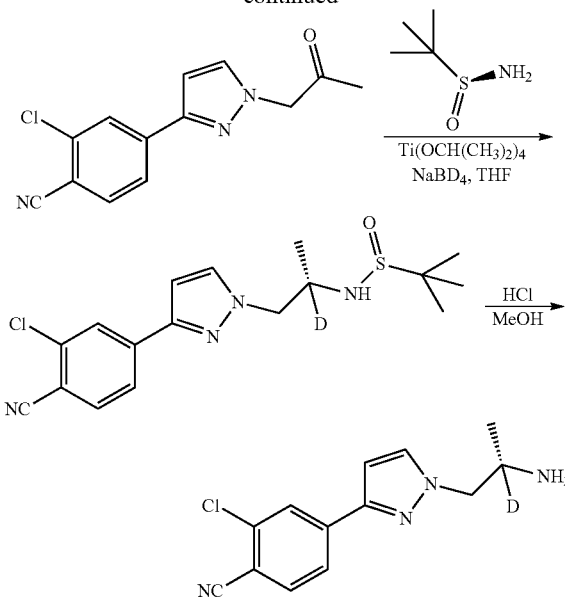

Step 1: Synthesis of Compound 2-chloro-4-(1-(2-oxopropyl)-1H-pyrazol-3-yl)benzonitrile Under ice bath, NaH (600 mg, 15 mmol) was added in portions to a solution of 2-chloro-4-(1H-pyrazol-3-yl)benzonitrile (2.0 g, 9.85 mmol) in DMF (20 ml), and reacted at room temperature for 0.5 h. The above system was added with bromoacetone (2.56 g, 18.8 mmol), and reacted at room temperature for 2 h. The system was quenched with water, extracted with EA (100 mL×3), and dried with anhydrous sodium sulfate. Filtration, concentration under reduced pressure, and purification of the concentrated liquid by column chromatography (PE/EA=22%) provided 1.1 g of white solid. Yield: 43%. LC-MS (APCI): m/z=260.1 (M+1)$^+$.

Step 2: Synthesis of Compound N—((S)-1-(3-(3-chloro-4-cyanophenyl)-1H-pyrazol-1-yl)prop-2-yl-2-d)-2-methylpropan-2-sulfinamide At room temperature, (S)-tert-butylsulfinamide (185 mg, 1.53 mmol) and tetraisopropyl titanate (789 mg, 2.78 mmol) were added to a solution of 2-chloro-4-(1-(2-oxopropyl)-1H-pyrazol-3-yl)benzonitrile (360 mg, 1.39 mmol) in THF (10 mL), and reacted at 72° C. overnight. At −20° C., NaBD$_4$ (168 mg, 5.56 mmol) was added in portions, and reacted for 2 h at room temperature. It was quenched with water, extracted with EA (100 mL×3), and dried with anhydrous sodium sulfate. Filtration, concentration under reduced pressure, and purification of the concentrated liquid by column chromatography (PE/EtOAc=64%) provided 360 mg of white solid. Yield: 65%. LC-MS (APCI): m/z=364.1 (M+1)$^+$.

Step 3: Synthesis of Intermediate A3

At room temperature, HCl (4M, MeOH solution) (3 ml) was added to a solution of N—((S)-1-(3-(3-chloro-4-cyanophenyl)-1H-pyrazol-1-yl)prop-2-yl)-2-methylpropan-2-sulfinamide (360 mg, 0.99 mmol) in methanol (5 ml), and reacted at room temperature for 1 h. Rotation-drying and purification by column chromatography (DCM/MeOH=8%) provided 116 mg of white solid. Yield: 45%. LC-MS (APCI): m/z=262.1 (M+1)$^+$.

Preparation of Intermediate A4 (S)-4-(1-(2-aminopropyl-1,1,3,3,3-d$_5$)-1H-pyrazol-3-yl)-2-chlorobenzonitrile

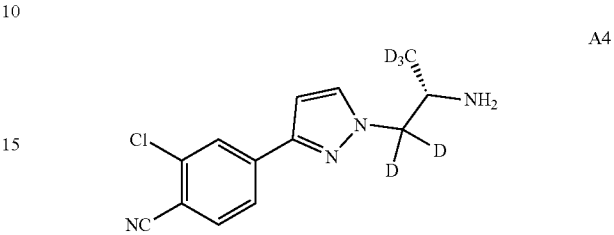

The following synthetic route was used.

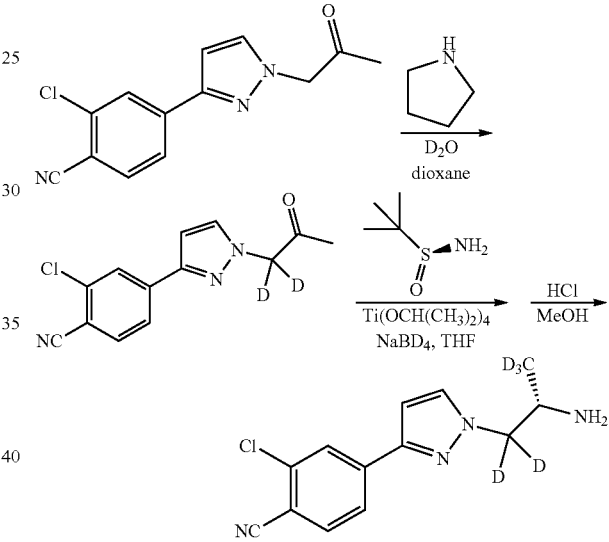

Step 1: Synthesis of Compound 2-chloro-4-(1-(2-oxopropyl-1,1,3,3,3-d$_5$)-1H-pyrazol-3-yl)benzonitrile At room temperature, tetrahydropyrrole (5 mg) was added to a solution of 2-chloro-4-(1-(2-oxopropyl)-1H-pyrazol-3-yl)benzonitrile (1 g, 3.85 mmol) in a mixture of 1,4-dioxane (15 mL) and D$_2$O (15 mL), and reacted for 72 h at room temperature. Rotation drying, concentration under reduced pressure, and purification of the concentrated liquid by column chromatography (PE/EA=23%) provided 850 mg of white solid. Yield: 86%. LC-MS (APCI): m/z=265.1 (M+1)+, $^1$H NMR (300 MHz, DMSO-d$_6$) δ 8.08 (d, J=1.2 Hz, 1H), 8.00-7.90 (m, 2H), 7.77 (d, J=2.4 Hz, 1H), 7.01 (d, J=2.4 Hz, 1H).

Step 2: Synthesis of Intermediate A4

At room temperature, (S)-tert-butylsulfinamide (358 mg, 2.96 mmol) and tetraisopropyl titanate (1.53 g, 5.38 mmol) were added to a solution of 2-chloro-4-(1-(2-oxopropyl-1,1,3,3,3-d$_5$)-1H-pyrazol-3-yl)benzonitrile (710 mg, 2.69 mmol) in THF (10 mL), and reacted overnight at 72° C. At −20° C., NaBD₄ (500 mg, 13.45 mmol) was added in portions, and reacted for 2 h at room temperature. It was quenched with water, extracted with EA (100 mL×3), and dried with anhydrous sodium sulfate. Filtration, concentration under reduced pressure, and purification of the concentrated liquid by column chromatography (PE/EA=64%) provided 750 mg of white solid.

At room temperature, HCl (4M, MeOH solution) (3 mL) was added to a solution of the above product in methanol (5 mL), and reacted for 1 h at room temperature. Rotation drying and purification by column chromatography (DCM/MeOH=8%) provided 420 mg of white solid. Yield: 45%. LC-MS (APCI): m/z=266.1 (M+1)⁺.

Preparation of Intermediate B
5-acetyl-1H-pyrazole-3-carboxylic Acid

The following synthetic route was used.

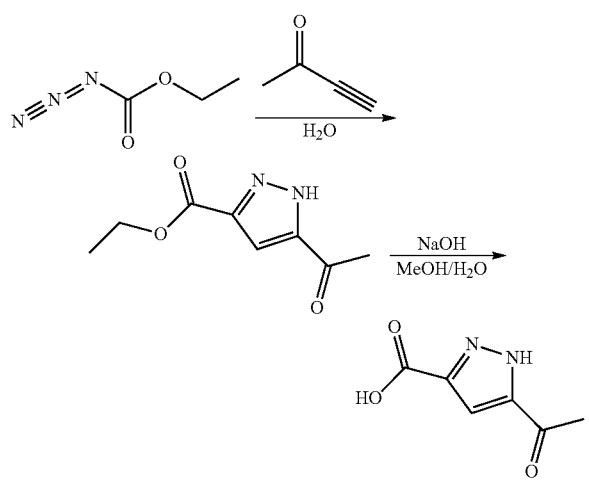

Step 1: Synthesis of Compound
5-acetyl-1H-pyrazole-3-carboxylic acid ethyl ester At room temperature, ethyl azidoacetate (12.5 g, 110 mmol) was slowly added dropwise to a solution of 3-Butyn-2-one (5 g, 73 mmol) in water (80 mL). The reaction was stirred at room temperature for 4 hours, and the solid was filtered out to obtain 11 g of light yellow solid. Yield: 81%. LC-MS (APCI): m/z=183.2, 1H NMR (300 MHz, CDCl3) δ 11.69 (s, 1H), 7.33 (s, 1H), 4.43 (q, J=7.1 Hz, 2H), 2.61 (s, 3H), 1.41 (t, J=7.1 Hz, 3H).

Step 2: Synthesis of Intermediate B

At room temperature, NaOH (4.4 g, 108 mmol) was added to a solution of 5-acetyl-1H-pyrazole-3-carboxylic acid ethyl ester (4.0 g, 22 mmol) in a mixture of methanol (20 mL) and water (20 mL). The reaction was stirred at room temperature for 2 hours, and adjusted to pH 2 with concentrated hydrochloric acid. The solid was filtered out to obtain 3.2 g of off-white solid. Yield: 94%. LC-MS (APCI): m/z=155.1.

Example 1

Preparation of N—((S)-1-(3-(3-chloro-4-cyanophenyl)-1H-pyrazol-1-yl)prop-2-yl)-5-(1-hydroxylethyl-1-d)-1H-pyrazole-3-carboxamide

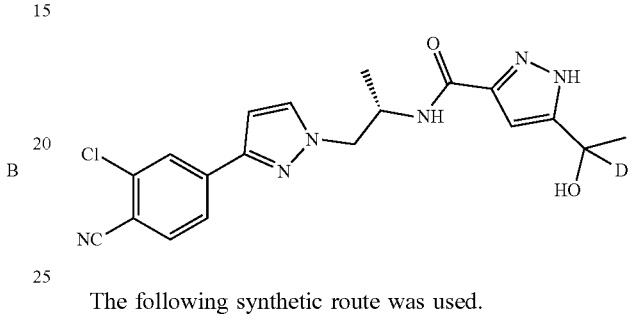

The following synthetic route was used.

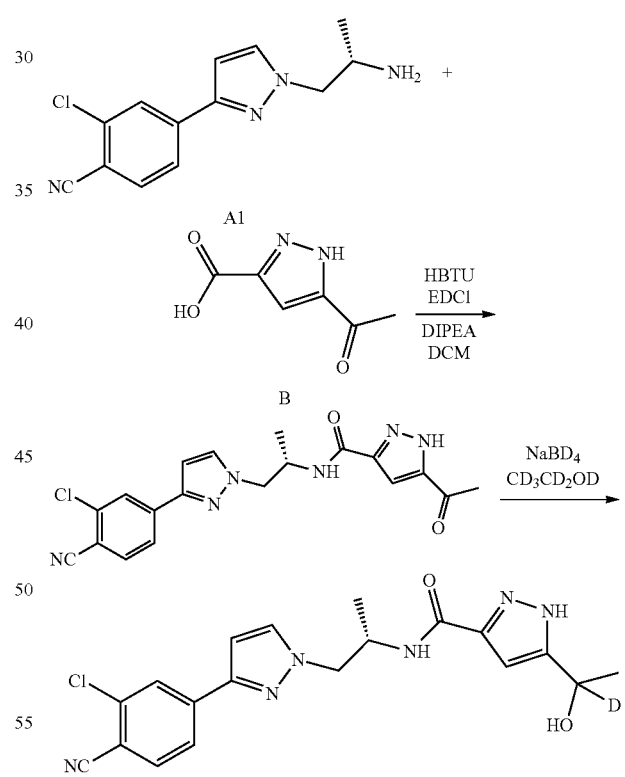

Step 1: Synthesis of Compound (S)-5-acetyl-N-(1-(3-(3-chloro-4-cyanophenyl)-1H-pyrazol-1-yl)prop-2-yl)-1H-pyrazole-3-carboxamide At room temperature, HBTU (1.53 g, 4.04 mmol), EDCI (775 mg, 4.04 mmol) and Intermediate A1 (700 mg, 2.69 mmol) were added to a solution of Intermediate B (500 mg, 3.23 mmol) and DIPEA (748 mg, 5.38 mmol) in anhydrous DCM (10 mL), and the reaction was stirred at room temperature overnight. The reaction was quenched with water, extracted with EA (100×3), and dried with anhydrous sodium sulfate. Filtration, concentration under reduced pressure, and purification of the concentrated liquid by column chromatography (PE/EA=80%) provided 534 mg of white solid. Yield: 50%. LC-MS (APCI): m/z=397.1 (M+1)$^+$.

Step 2: Synthesis of Compound N—((S)-1-(3-(3-chloro-4-cyanophenyl)-1H-pyrazol-1-yl)prop-2-yl)-5-(1-hydroxylethyl-1-d)-1H-pyrazole-3-carboxamide At room temperature, NaBD$_4$ (32 mg, 0.76 mmol) was added to a solution of (S)-5-acetyl-N-(1-(3-(3-chloro-4-cyanophenyl)-1H-pyrazol-1-yl)prop-2-yl)-1H-pyrazole-3-carboxamide (150 mg, 0.38 mmol) in anhydrous CD$_3$CD$_2$OD (5 mL), and the reaction was stirred at room temperature for 2.5 h. The reaction was quenched by H$_2$O (20 mL) and HCl (0.5M, 0.3 mL). CD$_3$CD$_2$OD was removed under reduced pressure, and the residue was dissolved in DCM, washed with 1M sodium bicarbonate solution and water, dried over anhydrous sodium sulfate, filtered, and concentrated under reduced pressure. Purification of the concentrated liquid by column chromatography (DCM/MeOH=6%) provided 56 mg of white solid. Yield: 51.85%, purity: 99.46%. LC-MS (APCI): m/z=400.1 (M+1)$^+$, $^1$H NMR (300 MHz, DMSO-d$_6$) δ 13.04 (s, 1H), 8.21 (d, J=7.7 Hz, 1H), 8.07 (s, 1H), 7.98 (s, 2H), 7.80 (d, J=2.2 Hz, 1H), 6.93 (d, J=2.2 Hz, 1H), 6.38 (s, 1H), 5.41 (s, 1H), 4.48-4.28 (m, 3H), 1.36 (d, J=6.3 Hz, 3H), 1.09 (d, J=5.7 Hz, 3H).

Example 2

Preparation of N—((S)-1-(3-(3-chloro-4-cyanophenyl)-1H-pyrazol-1-yl)prop-2-yl)-5-(1-hydroxylethyl-2,2,2-d$_3$)-1H-pyrazole-3-carboxamide

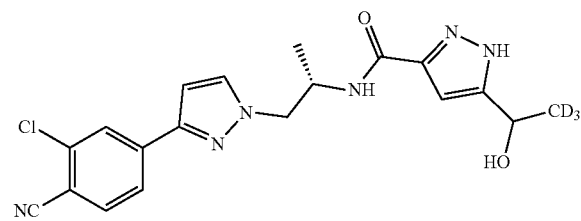 [SMILES: [2H]C([2H])([2H])C(O)c1cc(C(=O)N[C@@H](C)Cn2ccc(-c3ccc(C#N)c(Cl)c3)n2)n[nH]1]

The following synthetic route was used.

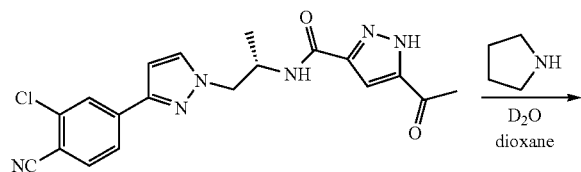

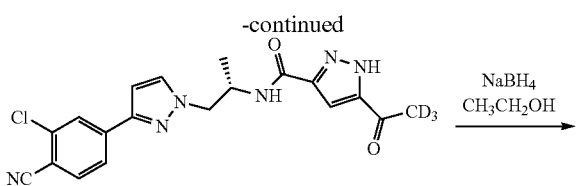

Step 1: Synthesis of Compound (S)-5-(acetyl-d$_3$)-N-(1-(3-(3-chloro-4-cyanophenyl)-1H-pyrazol-1-yl)prop-2-yl)-1H-pyrazole-3-carboxamide At room temperature, tetrahydropyrrole (5 mg) was added to a solution of (S)-5-acetyl-N-(1-(3-(3-chloro-4-cyanophenyl)-1H-pyrazol-1-yl)prop-2-yl)-1H-pyrazole-3-carboxamide (400 mg, 1.0 mmol) in a mixture of 1,4-dioxane (10 mL) and D$_2$O (10 mL), and reacted for 72 h at room temperature. Rotation drying, concentration under reduced pressure, and purification of the concentrated liquid by column chromatography (PE/EA=81%) provided 380 mg of white solid. Yield: 95%. LC-MS (APCI): m/z=400.1 (M+1)$^+$, $^1$H NMR (500 MHz, DMSO-d$_6$) δ 14.18 (d, J=39.3 Hz, 1H), 8.51 (s, 1H), 8.00 (d, J=28.9 Hz, 2H), 7.82 (d, J=2.3 Hz, 1H), 7.62 (s, 1H) 7.32 (s, 1H), 6.94 (d, J=2.1 Hz, 1H), 4.44-4.29 (m, 3H), 1.19-1.13 (m, 3H).

Step 2: Synthesis of Compound N—((S)-1-(3-(3-chloro-4-cyanophenyl)-1H-pyrazol-1-yl)prop-2-yl)-5-(1-hydroxylethyl-2,2,2-d$_3$)-1H-pyrazole-3-carboxamide

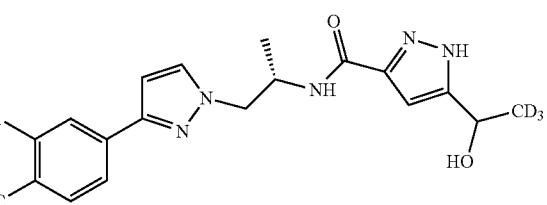

At room temperature, NaBH$_4$ (28 mg, 74 mmol) was added to (S)-5-(acetyl-d$_3$)-N-(1-(3-(3-chloro-4-cyanophenyl)-1H-pyrazol-1-yl)prop-2-yl)-1H-pyrazole-3-carboxamide (150 mg, 0.37 mmol) in absolute ethanol (5 mL), and the reaction was stirred at room temperature for 2.5 h. The reaction was quenched by H$_2$O (10 mL) and HCl (0.5M, 0.3 mL). Ethanol was removed under reduced pressure, and the residue was dissolved in DCM, washed with 1M sodium bicarbonate solution and water, dried over anhydrous sodium sulfate, filtered, and concentrated under reduced pressure. Purification of the concentrated liquid by column chromatography (DCM/MeOH=6%) provided 78 mg of white solid. Yield: 52%, purity: 99.44%. m/z=402.1 (M+1)+, $^1$H NMR (300 MHz, DMSO-d$_6$) δ 13.04 (s, 1H), 8.21 (d, J=7.7 Hz, 1H), 8.07 (s, 1H), 7.98 (s, 2H), 7.80 (d, J=2.2 Hz, 1H), 6.93 (d, J=2.2 Hz, 1H), 6.38 (s, 1H), 5.41 (s, 1H), 4.77 (s, 1H), 4.48-4.40 (s, 3H), 1.09 (d, J=5.7 Hz, 3H).

Example 3

Preparation of N—((S)-1-(3-(3-chloro-4-cyanophenyl)-1H-pyrazol-1-yl)prop-2-yl)-5-(1-hydroxylethyl-1,2,2,2-d₄)-1H-pyrazole-3-carboxamide

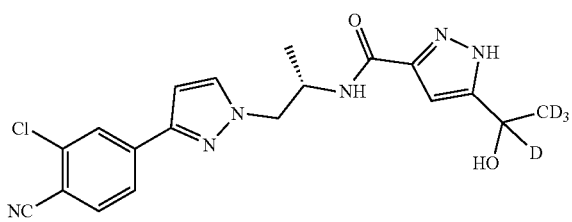 [SMILES: [2H]C([2H])([2H])C([2H])(O)c1cc(C(=O)N[C@@H](C)Cn2ccc(-c3ccc(C#N)c(Cl)c3)n2)n[nH]1]

The following synthetic route was used.

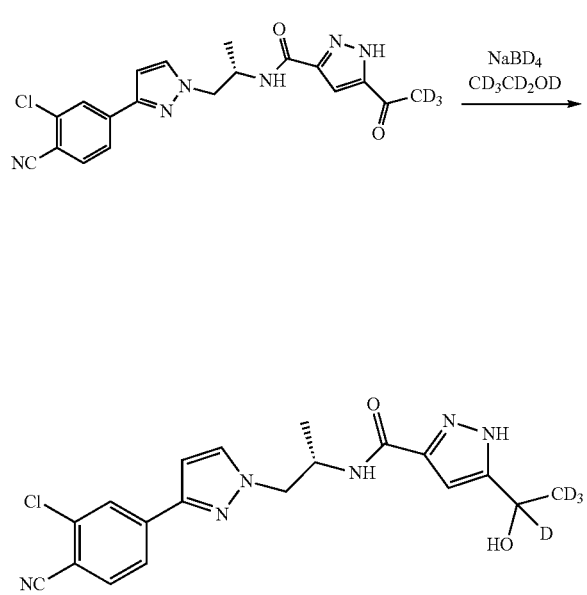

At room temperature, NaBD₄ (31 mg, 74 mmol) was added to (S)-5-(acetyl-d₃)-N-(1-(3-(3-chloro-4-cyanophenyl)-1H-pyrazol-1-yl)prop-2-yl)-1H-pyrazole-3-carboxamide (150 mg, 0.37 mmol) in anhydrous CD₃CD₂OD (5 mL), and the reaction was stirred at room temperature for 2.5 h. The reaction was quenched by H₂O (10 mL) and HCl (0.5M, 0.3 mL). CD₃CD₂OD was removed under reduced pressure, and the residue was dissolved in DCM, washed with 1M sodium bicarbonate solution and water, dried over anhydrous sodium sulfate, filtered, and concentrated under reduced pressure. Purification of the concentrated liquid by column chromatography (DCM/MeOH=6%) provided 69 mg of white solid. Yield: 46%, purity: 99.37%. LC-MS (APCI): m/z=403.1 (M+1)⁺, ¹H NMR (300 MHz, DMSO-d₆) δ 13.04 (s, 1H), 8.21 (d, J=7.7 Hz, 1H), 8.07 (s, 1H), 7.98 (s, 2H), 7.80 (d, J=2.2 Hz, 1H), 6.93 (d, J=2.2 Hz, 1H), 6.38 (s, 1H), 5.41 (s, 1H), 4.48-4.40 (s, 3H), 1.09 (d, J=5.7 Hz, 3H).

Example 4

Preparation of N—((S)-1-(3-(3-chloro-4-cyanophenyl)-1H-pyrazol-1-yl)prop-2-yl-1,1-d₂)-5-(1-hydroxyethyl)-1H-pyrazole-3-carboxamide

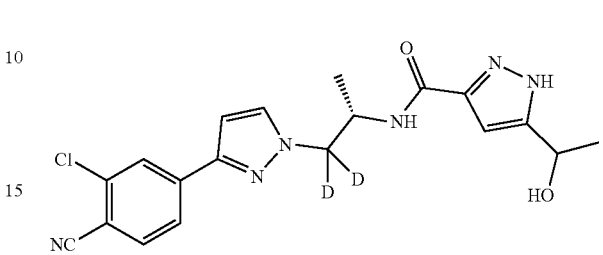

The following synthetic route was used.

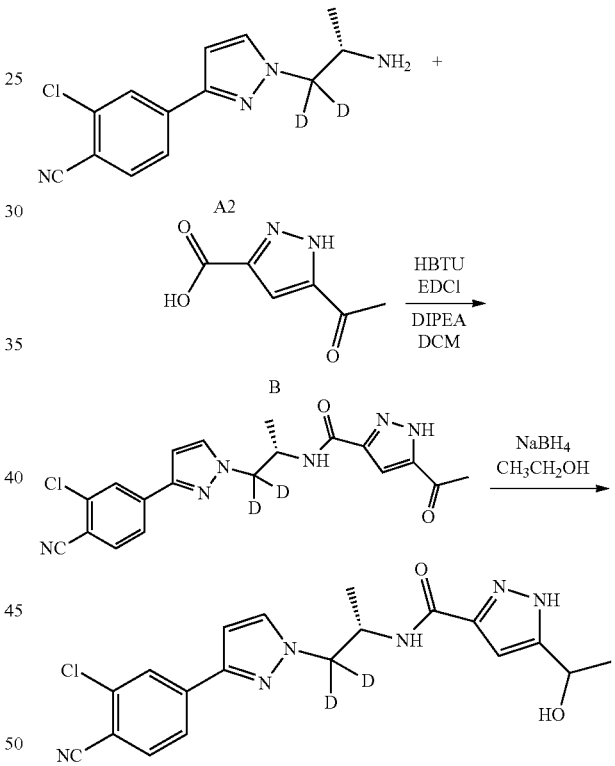

Step 1: Synthesis of Compound (S)-5-acetyl-N-(1-(3-(3-chloro-4-cyanophenyl)-1H-pyrazol-1-yl)prop-2-yl-1,1-d₂)-1H-pyrazole-3-carboxamide At room temperature, HBTU (1215 mg, 3.21 mmol), EDCI (616 mg, 3.21 mmol) and Intermediate A2 (560 mg, 2.14 mmol) were added to a solution of Intermediate B (658 mg, 4.28 mmol) and DIPEA (594 mg, 4.28 mmol) in anhydrous DCM (10 mL), and the reaction was stirred at room temperature overnight. The reaction was quenched with water, extracted with EA (50×3), and dried with anhydrous sodium sulfate. Filtration, concentration under reduced pressure, and purification of the concentrated liquid by column chromatography (PE/EtOAc=81%) provided 500 mg of white solid. Yield: 58.2%. LC-MS (APCI): m/z=399.1 (M+1)+.

Step 2: Synthesis of Compound N—((S)-1-(3-(3-chloro-4-cyanophenyl)-1H-pyrazol-1-yl)prop-2-yl-1,1-d$_2$)-5-(1-hydroxyethyl)-1H-pyrazole-3-carboxamide At room temperature, NaBH$_4$ (48 mg, 1.25 mmol) was added to (S)-5-acetyl-N-(1-(3-(3-chloro-4-cyanophenyl)-1H-pyrazol-1-yl)prop-2-yl-1,1-d$_2$)-1H-pyrazole-3-carboxamide (250 mg, 0.628 mmol) in anhydrous ethanol (5 mL), and the reaction was stirred at room temperature for 2.5 h. The reaction was quenched by H$_2$O (10 mL) and HCl (0.5M, 0.3 mL). Ethanol was removed under reduced pressure, and the residue was dissolved in DCM, washed with 1M sodium bicarbonate solution and water, dried over anhydrous sodium sulfate, filtered, and concentrated under reduced pressure. Purification of the concentrated liquid by column chromatography (DCM/MeOH=6%) provided 90 mg of white solid. Yield: 36%, purity: 92.67%. LC-MS (APCI): m/z=401.1 (M+1)+, $^1$H NMR (300 MHz, DMSO-d$_6$) δ 13.04 (s, 1H), 8.21 (d, J=7.7 Hz, 1H), 8.07 (s, 1H), 7.98 (s, 2H), 7.80 (d, J=2.2 Hz, 1H), 6.93 (d, J=2.2 Hz, 1H), 6.38 (s, 1H), 5.41 (s, 1H), 5.09 (s, OH), 4.77 (s, 1H), 4.48-4.40 (s, 1H), 1.36 (d, J=6.3 Hz, 3H), 1.09 (d, J=5.7 Hz, 3H).

Example 5

Preparation of N—((S)-1-(3-(3-chloro-4-cyanophenyl)-1H-pyrazol-1-yl)prop-2-yl-1,1-d$_2$)-5-(1-hydroxyethyl-1-d)-1H-pyrazole-3-carboxamide amide (250 mg, 0.628 mmol) in anhydrous CD$_3$CD$_2$OD (5 mL), and the reaction was stirred at room temperature for 2.5 h. The reaction was quenched by H$_2$O (10 mL) and HCl (0.5M, 0.3 mL). Ethanol was removed under reduced pressure, and the residue was dissolved in DCM, washed with 1M sodium bicarbonate solution and water, dried over anhydrous sodium sulfate, filtered, and concentrated under reduced pressure. Purification of the concentrated liquid by column chromatography (DCM/MeOH=6%) provided 135 mg of white solid. Yield: 54%, purity: 97.78%. LC-MS (APCI): m/z=402.1 (M+1)+, $^1$H NMR (300 MHz, DMSO-d$_6$) δ 13.04 (s, 1H), 8.21 (d, J=7.7 Hz, 1H), 8.07 (s, 1H), 7.98 (s, 2H), 7.80 (d, J=2.2 Hz, 1H), 6.93 (d, J=2.2 Hz, 1H), 6.38 (s, 1H), 5.41 (s, 1H), 5.09 (s, OH), 4.48-4.40 (s, 1H), 1.36 (d, J=6.3 Hz, 3H), 1.09 (d, J=5.7 Hz, 3H).

Example 6

Preparation of N—((S)-1-(3-(3-chloro-4-cyanophenyl)-1H-pyrazol-1-yl)prop-2-yl-1,1-d$_2$)-5-(1-hydroxyethyl-2,2,2-d$_3$)-1H-pyrazole-3-carboxamide

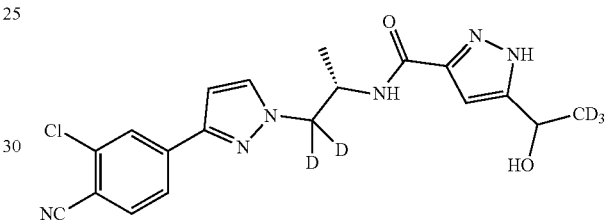

The following synthetic route was used.

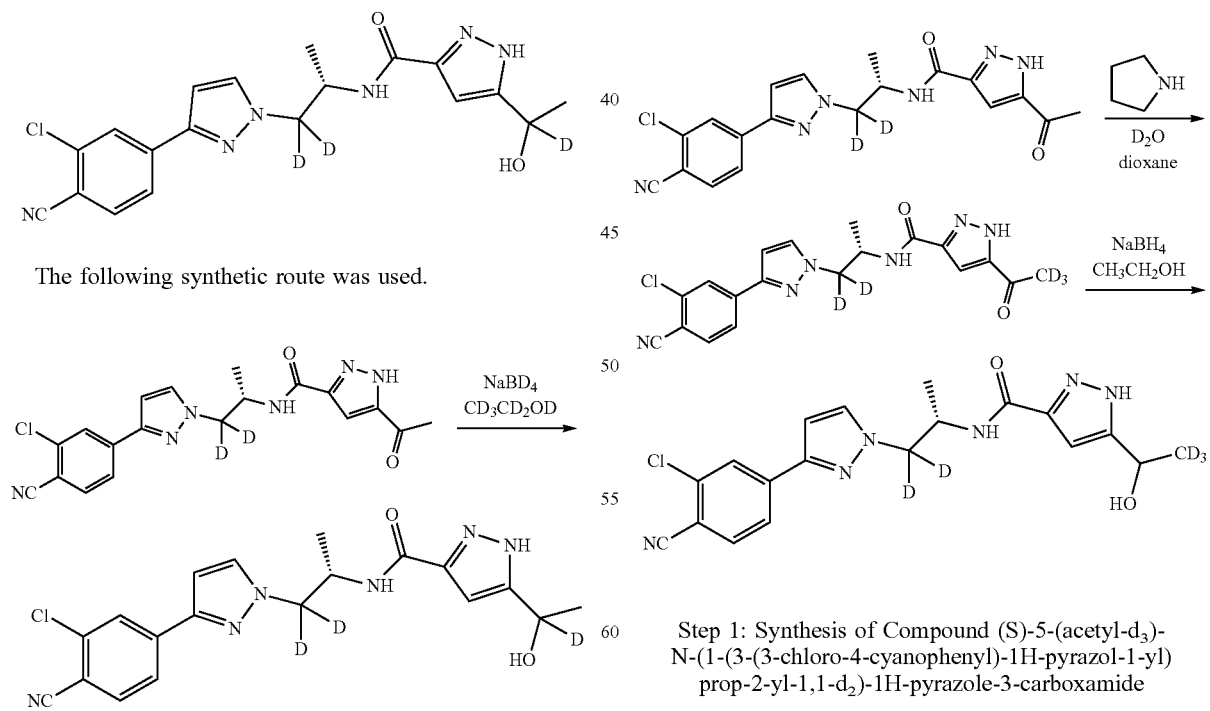

At room temperature, NaBD$_4$ (53 mg, 1.25 mmol) was added to (S)-5-acetyl-N-(1-(3-(3-chloro-4-cyanophenyl)-1H-pyrazol-1-yl)prop-2-yl-1,1-d$_2$)-1H-pyrazole-3-carbox- Step 1: Synthesis of Compound (S)-5-(acetyl-d$_3$)-N-(1-(3-(3-chloro-4-cyanophenyl)-1H-pyrazol-1-yl)prop-2-yl-1,1-d$_2$)-1H-pyrazole-3-carboxamide At room temperature, tetrahydropyrrole (5 mg) was added to a solution of (S)-5-(acetyl)-N-(1-(3-(3-chloro-4-cyanophenyl)-1H-pyrazol-1-yl)prop-2-yl-1,1-d$_2$)-1H-pyrazole-3-carboxamide (400 mg, 1.0 mmol) in a mixture of 1,4- dioxane (10 mL) and D₂O (10 mL), and reacted for 72 h at room temperature. Rotation drying, concentration under reduced pressure, and purification of the concentrated liquid by column chromatography (PE/EA=81%) provided 380 mg of white solid. Yield: 95%. LC-MS (APCI): m/z=402.1 (M+1)⁺, ¹H NMR (500 MHz, DMSO-d₆) δ 14.18 (d, J=39.3 Hz, 1H), 8.51 (s, 1H), 8.00 (d, J=28.9 Hz, 2H), 7.82 (d, J=2.3 Hz, 1H), 7.62 (s, 1H), 7.32 (s, 1H), 6.94 (d, J=2.1 Hz, 1H), 4.44 (s, 1H), 1.19-1.13 (m, 3H).

Step 2: Synthesis of Compound N—((S)-1-(3-(3-chloro-4-cyanophenyl)-1H-pyrazol-1-yl)prop-2-yl-1,1-d₂)-5-(1-hydroxyethyl-2,2,2-d₃)-1H-pyrazole-3-carboxamide At room temperature, NaBH₄ (28 mg, 74 mmol) was added to (S)-5-(acetyl-d₃)-N-(1-(3-(3-chloro-4-cyanophenyl)-1H-pyrazol-1-yl)prop-2-yl-1,1-d₂)-1H-pyrazole-3-carboxamide (150 mg, 0.37 mmol) in absolute ethanol (5 mL), and the reaction was stirred at room temperature for 2.5 h. The reaction was quenched by H₂O (10 mL) and HCl (0.5M, 0.3 mL). Ethanol was removed under reduced pressure, and the residue was dissolved in DCM, washed with 1M sodium bicarbonate solution and water, dried over anhydrous sodium sulfate, filtered, and concentrated under reduced pressure. Purification of the concentrated liquid by column chromatography (DCM/MeOH=6%) provided 100 mg of white solid. Yield: 67%, purity: 99.6%. LC-MS (APCI): m/z=402.1 (M+1)⁺, ¹H NMR (300 MHz, DMSO-d₆) δ 13.04 (s, 1H), 8.21 (d, J=7.7 Hz, 1H), 8.07 (s, 1H), 7.98 (s, 2H), 7.80 (d, J=2.2 Hz, 1H), 6.93 (d, J=2.2 Hz, 1H), 6.38 (s, 1H), 5.41 (s, 1H), 4.77 (s, 1H), 4.48-4.40 (s, 1H), 1.09 (d, J=5.7 Hz, 3H).

Example 7

Preparation of N—((S)-1-(3-(3-chloro-4-cyanophenyl)-1H-pyrazol-1-yl)prop-2-yl-1,1-d₂)-5-(1-hydroxyethyl-1,2,2,2-d₄)-1H-pyrazole-3-carboxamide

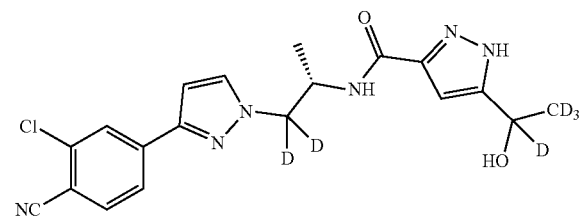 [SMILES: [2H]C([2H])([C@H](C)NC(=O)c1cc(C([2H])(O)C([2H])([2H])[2H])[nH]n1)n1ccc(-c2ccc(C#N)c(Cl)c2)n1]

The following synthetic route was used.

At room temperature, NaBD₄ (31 mg, 74 mmol) was added to (S)-5-(acetyl-d₃)-N-(1-(3-(3-chloro-4-cyanophenyl)-1H-pyrazol-1-yl)prop-2-yl-1,1-d₂)-1H-pyrazole-3-carboxamide (150 mg, 0.37 mmol) in anhydrous CD₃CD₂OD (5 mL), and the reaction was stirred at room temperature for 2.5 h. The reaction was quenched by H₂O (10 mL) and HCl (0.5M, 0.3 mL). Ethanol was removed under reduced pressure, and the residue was dissolved in DCM, washed with 1M sodium bicarbonate solution and water, dried over anhydrous sodium sulfate, filtered, and concentrated under reduced pressure. Purification of the concentrated liquid by column chromatography (DCM/MeOH=6%) provided 104 mg of white solid. Yield: 69%, purity: 97.89%. LC-MS (APCI): m/z=402.1 (M+1)⁺, ¹H NMR (300 MHz, DMSO-d₆) δ 13.04 (s, 1H), 8.21 (d, J=7.7 Hz, 1H), 8.07 (s, 1H), 7.98 (s, 2H), 7.80 (d, J=2.2 Hz, 1H), 6.93 (d, J=2.2 Hz, 1H), 6.38 (s, 1H), 5.41 (s, 1H), 4.48-4.40 (s, 1H), 1.09 (d, J=5.7 Hz, 3H).

Example 8

Preparation of N—((S)-1-(3-(3-chloro-4-cyanophenyl)-1H-pyrazol-1-yl)prop-2-yl-2-d)-5-(1-hydroxyethyl)-1H-pyrazole-3-carboxamide

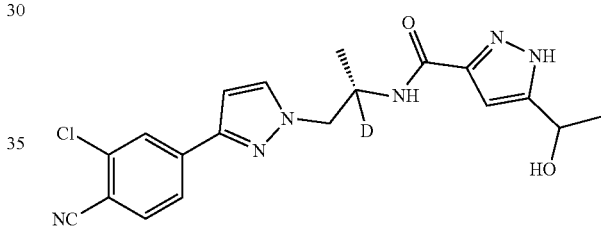

The following synthetic route was used.

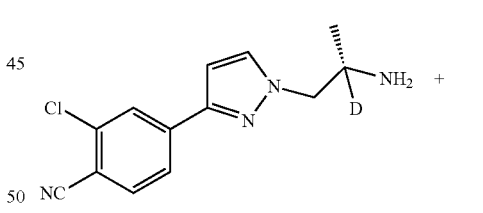

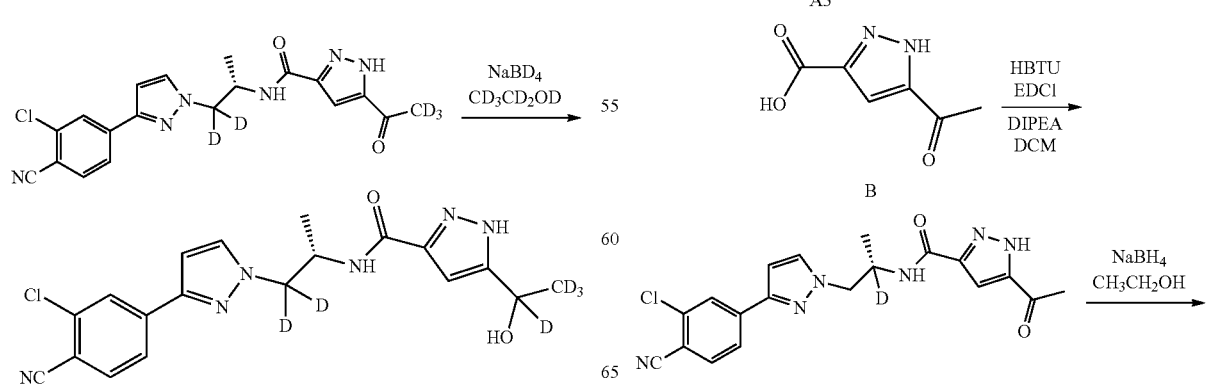

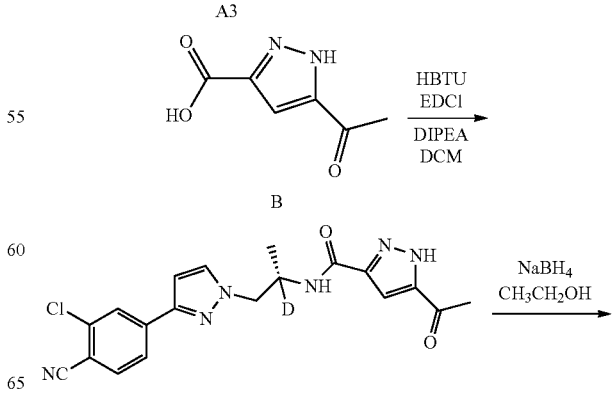

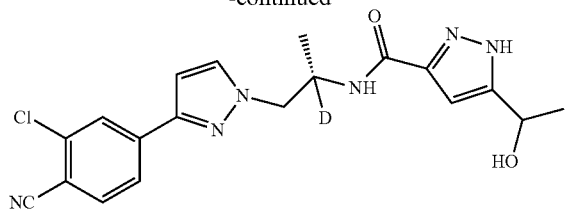

Step 1: Synthesis of Compound (S)-5-(acetyl)-N-(1-(3-(3-chloro-4-cyanophenyl)-1H-pyrazol-1-yl)prop-2-yl-2-d)-1H-pyrazole-3-carboxamide At room temperature, HBTU (253 mg, 0.66 mmol), EDCI (128 mg, 0.66 mmol) and Intermediate A3 (116 mg, 0.44 mmol) were added to a solution of Intermediate B (136 mg, 0.88 mmol) and DIPEA (124 mg, 0.88 mmol) in anhydrous DCM (10 mL), and the reaction was stirred at room temperature overnight. The reaction was quenched with water, extracted with EA (30×3), and dried with anhydrous sodium sulfate. Filtration, concentration under reduced pressure, and purification of the concentrated liquid by column chromatography (PE/EA=83%) provided 150 mg of white solid. Yield: 85%. LC-MS (APCI): m/z=398.1 (M+1)⁺.

Step 2: Synthesis of Compound N—((S)-1-(3-(3-chloro-4-cyanophenyl)-1H-pyrazol-1-yl)prop-2-yl-2-d)-5-(1-hydroxyethyl)-1H-pyrazole-3-carboxamide At room temperature, NaBH₄ (29 mg, 7.2 mmol) was added to (S)-5-(acetyl)-N-(1-(3-(3-chloro-4-cyanophenyl)-1H-pyrazol-1-yl)prop-2-yl-2-d)-1H-pyrazole-3-carboxamide (150 mg, 0.38 mmol) in absolute ethanol (5 mL), and the reaction was stirred at room temperature for 2.5 h. The reaction was quenched by H₂O (10 mL) and HCl (0.5M, 0.3 mL). Ethanol was removed under reduced pressure, and the residue was dissolved in DCM, washed with 1M sodium bicarbonate solution and water, dried over anhydrous sodium sulfate, filtered, and concentrated under reduced pressure. Purification of the concentrated liquid by column chromatography (DCM/MeOH=6%) provided 46 mg of white solid. Yield: 31%, purity: 97.81%. LC-MS (APCI): m/z=400.1 (M+1)⁺, ¹H NMR (300 MHz, DMSO-d₆) δ 13.04 (s, 1H), 8.21 (d, J=7.7 Hz, 1H), 8.07 (s, 1H), 7.98 (s, 2H), 7.80 (d, J=2.2 Hz, 1H), 6.93 (d, J=2.2 Hz, 1H), 6.38 (s, 1H), 5.41 (s, 1H), 4.77 (s, 1H), 4.45-4.40 (s, 2H), 1.36 (d, J=6.3 Hz, 3H), 1.09 (d, J=5.7 Hz, 3H).

Example 9

Preparation of N—((S)-1-(3-(3-chloro-4-cyanophenyl)-1H-pyrazol-1-yl)prop-2-yl-1,1,3,3,3-d₅)-5-(1-hydroxyethyl)-1H-pyrazole-3-carboxamide

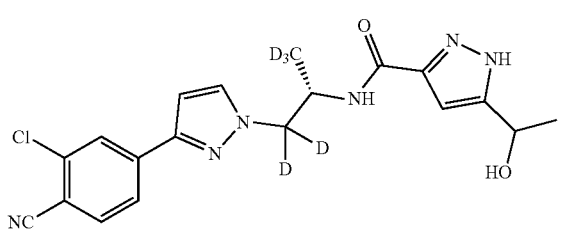 [SMILES: [2H]C([2H])([2H])[C@H](NC(=O)c1cc(C(C)O)[nH]n1)C([2H])([2H])n1ccc(-c2ccc(C#N)c(Cl)c2)n1]

The following synthetic route was used.

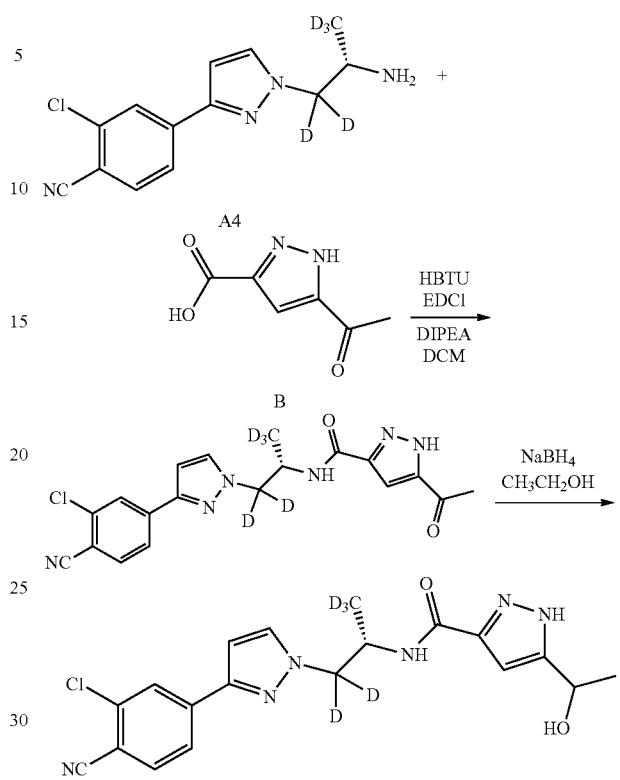

Step 1: Synthesis of Compound (S)-5-(acetyl)-N-(1-(3-(3-chloro-4-cyanophenyl)-1H-pyrazol-1-yl)prop-2-yl-1,1,3,3,3-d₅)-1H-pyrazole-3-carboxamide At room temperature, HBTU (921 mg, 2.33 mmol), EDCI (446 mg, 2.33 mmol) and Intermediate A4 (410 mg, 1.55 mmol) were added to a solution of Intermediate B (284 mg, 1.86 mmol) and DIPEA (430 mg, 2.33 mmol) in anhydrous DCM (10 mL), and the reaction was stirred at room temperature overnight. The reaction was quenched with water, extracted with EA (30×3), and dried with anhydrous sodium sulfate. Filtration, concentration under reduced pressure, and purification of the concentrated liquid by column chromatography (PE/EtOAc=83%) provided 300 mg of white solid. Yield: 85%. LC-MS (APCI): m/z=402.1 (M+1)⁺.

Step 2: Synthesis of Compound N—((S)-1-(3-(3-chloro-4-cyanophenyl)-1H-pyrazol-1-yl)prop-2-yl-1,1,3,3,3-d₅)-5-(1-hydroxyethyl)-1H-pyrazole-3-carboxamide At room temperature, NaBH₄ (29 mg, 7.2 mmol) was added to (S)-5-(acetyl)-N-(1-(3-(3-chloro-4-cyanophenyl)-1H-pyrazol-1-yl)prop-2-yl-1,1,3,3,3-d₅)-1H-pyrazole-3-carboxamide (150 mg, 0.38 mmol) in absolute ethanol (5 mL), and the reaction was stirred at room temperature for 2.5 h. The reaction was quenched by H₂O (10 mL) and HCl (0.5M, 0.3 mL). Ethanol was removed under reduced pressure, and the residue was dissolved in DCM, washed with 1M sodium bicarbonate solution and water, dried over anhydrous sodium sulfate, filtered, and concentrated under reduced pressure. Purification of the concentrated liquid by column chromatography (DCM/MeOH=6%) provided 56 mg of white solid. Yield: 37%, purity: 97.81%. LC-MS (APCI): m/z=404.1 (M+1)+, 1H NMR (300 MHz, DMSO-d6) δ 13.04 (s, 1H), 8.21 (d, J=7.7 Hz, 1H), 8.07 (s, 1H), 7.98 (s, 2H), 7.80 (d, J=2.2 Hz, 1H), 6.93 (d, J=2.2 Hz, 1H), 6.38 (s, 1H), 5.41 (s, 1H), 4.77 (s, 1H), 4.45-4.40 (s, 1H), 1.36 (d, J=6.3 Hz, 3H).

Example 10

Preparation of N—((S)-1-(3-(3-chloro-4-cyanophenyl)-1H-pyrazol-1-yl)prop-2-yl-1,1,3,3,3-d5)-5-(1-hydroxyethyl-1-d)-1H-pyrazole-3-carboxamide

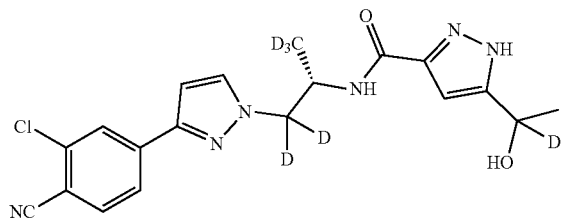 [SMILES: [2H]C(C)(O)c1cc(C(=O)N[C@@H](C([2H])([2H])[2H])C([2H])([2H])n2ccc(-c3ccc(C#N)c(Cl)c3)n2)n[nH]1]

The following synthetic route was used.

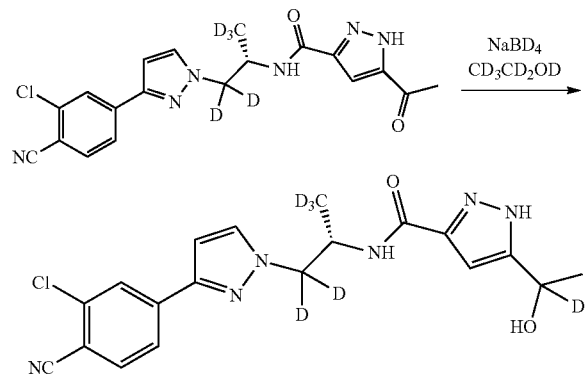

At room temperature, NaBD4 (31 mg, 7.2 mmol) was added to (S)-5-(acetyl)-N-(1-(3-(3-chloro-4-cyanophenyl)-1H-pyrazol-1-yl)prop-2-yl-1,1,3,3,3-d5)-1H-pyrazole-3-carboxamide (150 mg, 0.38 mmol) in anhydrous CD3CD2OD (5 mL), and the reaction was stirred at room temperature for 2.5 h. The reaction was quenched by H2O (10 mL) and HCl (0.5M, 0.3 mL). Ethanol was removed under reduced pressure, and the residue was dissolved in DCM, washed with 1M sodium bicarbonate solution and water, dried over anhydrous sodium sulfate, filtered, and concentrated under reduced pressure. Purification of the concentrated liquid by column chromatography (DCM/MeOH=6%) provided 48 mg of white solid. Yield: 32%. LC-MS (APCI): m/z=405.1 (M+1)+, 1H NMR (300 MHz, DMSO-d6) δ 13.04 (s, 1H), 8.21 (d, J=7.7 Hz, 1H), 8.07 (s, 1H), 7.98 (s, 2H), 7.80 (d, J=2.2 Hz, 1H), 6.93 (d, J=2.2 Hz, 1H), 6.38 (s, 1H), 5.41 (s, 1H), 4.45-4.40 (s, 1H), 1.36 (d, J=6.3 Hz, 3H).

Biological Activity Test
(1) Inhibition of Cellular PSA Protein Secretion
Experimental Steps:
1. Replacing the original medium with a medium containing 10% Charcoal Stripped FBS, and starving the cells in the culture flask for 24 hours;
2. Digesting the cells, counting them, seeding LNcaP cells in a 96-well plate at 10,000/well and incubating them overnight;
3. Adding DHT and the compound to the existing medium according to the set concentration, the final concentration of DHT being 1 nM and the initial concentration of compound being 50000 nM, 5-fold dilution, 8 concentration gradients, and incubating them for 48 hours; and
4. Collecting the cell culture supernatant, and detecting the PSA protein level according to the ELISA kit instructions.

According to the inhibition rate at each concentration, the IC50 was calculated with GraphPad Prism, and the results were shown in the table below.

It can be seen from the above table that the compounds of the present invention have a high inhibitory activity on cellular PSA protein, and thus can be used as medicines for treating prostate cancer.

(2) Androgen Receptor AR Affinity Test
The cytoplasm extracted from LNCap cells and commercial radioisotopes were used for AR affinity experiments.
The highest concentration of the drug to be tested was 1 μM, with 4-fold dilution and 8 concentrations. 1 μL of drug solution was added to each well of a 96-well plate (Agilent, 5042-1385) in duplicate. Each well was added with 100 μL of cytoplasm extracted from LNCap cells (600 ug/well), and 100 μL of radioisotope-labeled 3H-methyltrienone (final concentration 1.0 nM, PerkinElmer, Cat: NET590250UC, Lot: 2133648). The plate was sealed and shaken at 300 rpm at 4° C. for 24 h. 100 μL of radioligand adsorption buffer (Tris-HCl (10 mM), pH 7.4; EDTA (1.5 mM); DTT (1 mM); 0.25% activated carbon; 0.0025% dextran) was added, followed by shaking for 15 min at 4° C., and then centrifugation at 4° C., 3000 rpm for 30 min. 150 μL of the supernatant was transferred to a 6 ml Scint-tube (PerkinElmer, 6000192), and 2 mL of Ultima Gold cocktail (PerkinElmer, Cat: 6013329, Lot: 77-16371) was added. Tri-Carb 2910 TR (PerkinElmer) was used for isotope labeling reading, and the inhibition rate was calculated. Data was analyzed with GraphPad Prism 5.0 software, and fitted using nonlinear curve regression to produce the dose-effect curve and thereby calculate the IC50 value.

The compounds of the present invention were tested in the above AR affinity experiment. Compared with the non-deuterated compound Darolutamide, the compounds of the present invention have a comparable affinity and have an antagonistic effect on AR.

(3) DU145 Cell Proliferation Experiment (Negative Control)
The cell concentration was adjusted. 50 μL cell suspension was added to a 384-well plate, and incubated overnight at 37° C. and 5% CO2. Tecan D300E program was set up. The drug was added using a Tecan D300E instrument, the highest concentration of the drug to be tested being 10 μM, with a 3-fold gradient dilution, 9 concentrations, in duplicate, and the incubation was continued for 72 hours. The 384-well plate was taken out and equilibrated at room temperature for 30 minutes. Each well was added with 30 μL of CTG (Promega, G7573) reagent, and settled at room temperature for 10 minutes. After the signal was stable, the luminescence value was read on EnVision (Perkin Elmer 2104). Inhibition rate (%)=(1−Lum$_{test\ drug}$/Lum$_{negative\ control}$)×100. The negative control group was 0.667% DMSO. XL-fit software was used for calculation of IC50.

The compounds of the present invention were tested in the above-mentioned DU145 cell proliferation experiment. Compared with the non-deuterated compound Darolutamide, the compounds of the present invention have a comparable inhibitory effect on the proliferation of DU145 cells.

(4) Metabolic Stability Evaluation

Microsome experiment: human liver microsome: 0.5 mg/mL, Xenotech; rat liver microsome: 0.5 mg/mL, Xenotech; coenzyme (NADPH/NADH): 1 mM, Sigma Life Science; magnesium chloride: 5 mM, 100 mM phosphate buffer (pH 7.4).

Preparation of stock solution: a certain amount of the example compound powder and control compound powder were accurately weighed, and respectively dissolved to 5 mM with DMSO.

Preparation of phosphate buffer (100 mM, pH7.4): 150 mL of 0.5M potassium dihydrogen phosphate and 700 mL of 0.5M dipotassium hydrogen phosphate prepared beforehand were mixed, with pH of the mixture adjusted to 7.4 with 0.5M dipotassium hydrogen phosphate solution. Before use, the mixture was diluted by 5 folds with ultrapure water and magnesium chloride was added to obtain the phosphate buffer (100 mM), which contains 100 mM potassium phosphate, 3.3 mM magnesium chloride, and has pH 7.4.

NADPH regeneration system solution (containing 6.5 mM NADP, 16.5 mM G-6-P, 3 U/mL G-6-P D, 3.3 mM magnesium chloride) was prepared, and placed on wet ice before use.

Preparation of stop solution: a solution of 50 ng/mL propranolol hydrochloride and 200 ng/mL tolbutamide (internal standard) in acetonitrile. 25057.5 µL of phosphate buffer (pH 7.4) was taken into a 50 mL centrifuge tube, added with 812.5 µL of human liver microsome, and mixed well to obtain a liver microsome diluent with a protein concentration of 0.625 mg/mL. 25057.5 µL of phosphate buffer (pH 7.4) was taken into a 50 mL centrifuge tube, added with 812.5 µL of SD rat liver microsome, and mixed well to obtain a liver microsome diluent with a protein concentration of 0.625 mg/mL.

Incubation of the samples: the stock solutions of the corresponding compounds were respectively diluted to 0.25 mM with an aqueous solution containing 70% acetonitrile to obtain working solutions for later use. 398 µL of human liver microsome and rat liver microsome diluents were respectively taken and added to a 96-well incubation plate (N=2), added with 2 µL of 0.25 mM working solution respectively, and mixed well.

Determination of metabolic stability: 300 µL of pre-cooled stop solution was added to each well of a 96-well deep-well plate, and the plate was placed on ice as a stop plate. The 96-well incubation plate and the NADPH regeneration system were placed in a 37° C. water bath, shaken at 100 rpm, and pre-incubated for 5 minutes. 80 µL of incubation solution was taken out of each well of the incubation plate and added to the stop plate, mixed well, and supplemented with 20 µL of NADPH regeneration system solution to obtain the 0 min sample. Then 80 µL of NADPH regeneration system solution was added to each well of the incubation plate to initiate the reaction and start timing. The reaction concentration of the corresponding compound was 1 µM, and the protein concentration was 0.5 mg/mL. At 10, 30, and 90 minutes of reaction, 100 µL of the reaction solution was taken and added to the stop plate, and vortexed for 3 minutes to stop the reaction. The stop plate was centrifuged at 5000×g for 10 min at 4° C. 100 µL of supernatant was taken to a 96-well plate pre-added with 100 µL of distilled water, mixed well, and subjected to sample analysis by LC-MS/MS.

Data analysis: the peak areas of the corresponding compound and internal standard were detected through the LC-MS/MS system, and the ratio of the peak area of the compound to the internal standard was calculated. The natural logarithm of the remaining percentage of the compound was plotted against time to measure the slope and calculate $t_{1/2}$ and $CL_{int}$ according to the following equations, where V/M is equal to 1/protein concentration.

$$t_{1/2} = -\frac{0.693}{\text{Slope}},\ CL_{int} = \frac{0.693}{t_{1/2}} \cdot \frac{V}{M},\ t_{1/2}(\text{min});\ CL_{int}(\mu L/\text{min/mg})$$

The compounds of the present invention and the corresponding non-deuterated compounds were simultaneously tested for comparison and evaluated for the metabolic stability in human and rat liver microsomes. The non-deuterated compound Darolutamide was used as the control. In human and rat liver microsomal experiments, the compounds of the present invention significantly improved the metabolic stability, as compared with the non-deuterated compound Darolutamide. The results of representative example compounds are summarized in Table 1 below.

TABLE 1

| Example Compounds | HLM T$_{1/2}$ (min) | HLM CL (µL/min/mg) | RLM T$_{1/2}$ (min) | RLM CL (µL/min/mg) |
|---|---|---|---|---|
| Darolutamide | 163.0 | 8.5 | 113.7 | 12.2 |
| 1 | 222.1 | 6.2 | NA | NA |
| 2 | 152.8 | 9.1 | NA | NA |
| 3 | 349.9 | 4.0 | NA | NA |
| 4 | 162.2 | 8.5 | NA | NA |
| 5 | 321.3 | 4.3 | NA | NA |
| 6 | 217.0 | 6.4 | NA | NA |
| 7 | 201.5 | 6.9 | 194.8 | 7.1 |
| 8 | 190.5 | 7.3 | NA | NA |
| 9 | 171.2 | 8.1 | NA | NA |
| 10 | 317.2 | 4.4 | NA | NA |

(5) Rat Pharmacokinetics Experiment 6 male Sprague-Dawley rats, 7-8 weeks old, weighing about 210 g, were divided into 2 groups, 3 rats in each group, and a single dose of the compound (10 mg/kg orally) was administered intravenously or orally to compare the pharmacokinetics.

The rats were fed with standard feed and given water, and fasting began 16 hours before the test. The drug was dissolved with PEG400 and dimethyl sulfoxide. Blood was collected from the orbit. The time points for blood collection were 0.083, 0.25, 0.5, 1, 2, 4, 6, 8, 12, and 24 hours after administration.

The rats were briefly anesthetized after inhaling ether, and a blood sample of 300 µL was collected from the orbit in a test tube. There was 30 µL of 1% heparin salt solution in the test tube. Before use, the test tube was dried overnight at 60° C. After the blood sample was collected at the last time point, the rats were anesthetized with ether and sacrificed.

Immediately after the blood sample was collected, the test tube was gently inverted at least 5 times to ensure thorough mixing and then placed on ice. The blood sample was centrifuged at 5000 rpm for 5 minutes at 4° C. to separate the plasma from the red blood cells. 100 μL of plasma was transferred with a pipette into a clean plastic centrifuge tube, labeled with the name of the compound and the time point. The plasma was stored at −80° C. before analysis. The concentration of the compound of the invention in the plasma was determined by LC-MS/MS. The pharmacokinetic parameters were calculated based on the blood drug concentrations of each animal at different time points.

Experiments showed that the compounds of the present invention had better pharmacokinetic properties in animals and thus had better pharmacodynamics and therapeutic effects.

The above content is a further detailed description of the present invention in conjunction with specific preferred embodiments, and it cannot be considered that the specific implementation of the present invention is just limited to the description. For those of ordinary skill in the technical field to which the present invention belongs, a number of simple deductions or substitutions can be made without departing from the concept of the present invention, which should be regarded as falling within the protection scope of the present invention.

What is claimed is:

1. A compound of formula (I), or a tautomer, stereoisomer, prodrug, crystal form, pharmaceutically acceptable salt, hydrate or solvate thereof:

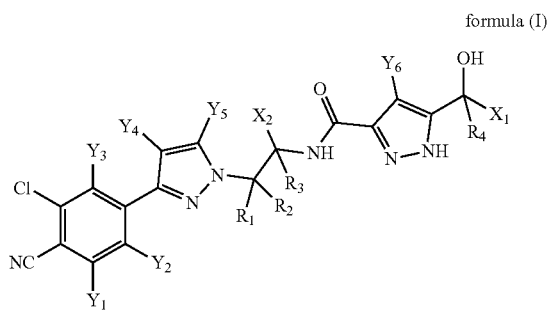

formula (I)

wherein $Y_1$, $Y_2$, $Y_3$, $Y_4$, $Y_5$ and $Y_6$ are each independently selected from hydrogen, deuterium or halogen;

$R_1$, $R_2$, $R_3$ and $R_4$ are each independently selected from hydrogen or deuterium;

$X_1$ and $X_2$ are each independently selected from $CH_3$, $CD_3$, $CHD_2$ or $CH_2D$;

provided that the compound comprises at least one deuterium atom.

2. The compound of claim 1, which is a compound of formula (I-1):

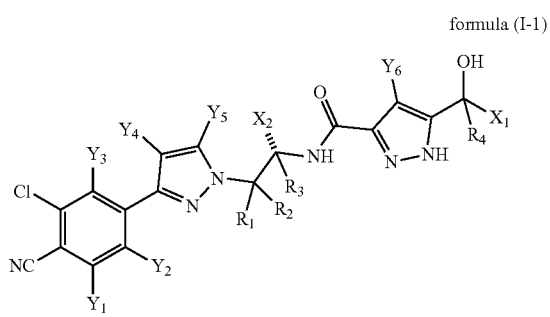

formula (I-1)

wherein $Y_1$, $Y_2$, $Y_3$, $Y_4$, $Y_5$, $Y_6$, $R_1$, $R_2$, $R_3$, $R_4$, $X_1$ and $X_2$ are as defined in claim 1;

or a tautomer, stereoisomer, prodrug, crystal form, pharmaceutically acceptable salt, hydrate or solvate thereof.

3. The compound according to claim 1, which is a compound of formula (II-1):

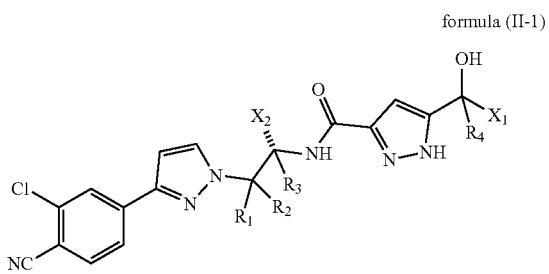

formula (II-1)

wherein $R_1$, $R_2$, $R_3$ and $R_4$ are each independently selected from hydrogen or deuterium;

$X_1$ and $X_2$ are each independently selected from $CH_3$, $CD_3$, $CHD_2$ or $CH_2D$;

provided that the compound comprises at least one deuterium atom;

or a tautomer, stereoisomer, prodrug, crystal form, pharmaceutically acceptable salt, hydrate or solvate thereof.

4. The compound according to claim 1, wherein $X_1$ is $CD_3$.

5. The compound according to claim 1, wherein $X_2$ is $CD_3$.

6. The compound according to claim 1, wherein $R_3$ is deuterium.

7. The compound according to claim 1, wherein $R_1$ and $R_2$ are deuterium.

8. The compound according to claim 1, wherein $R_4$ is deuterium.

9. The compound according to claim 1, which is selected from:

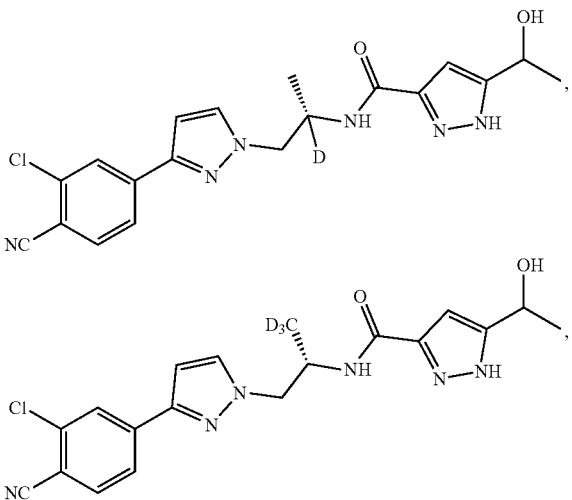

65
-continued
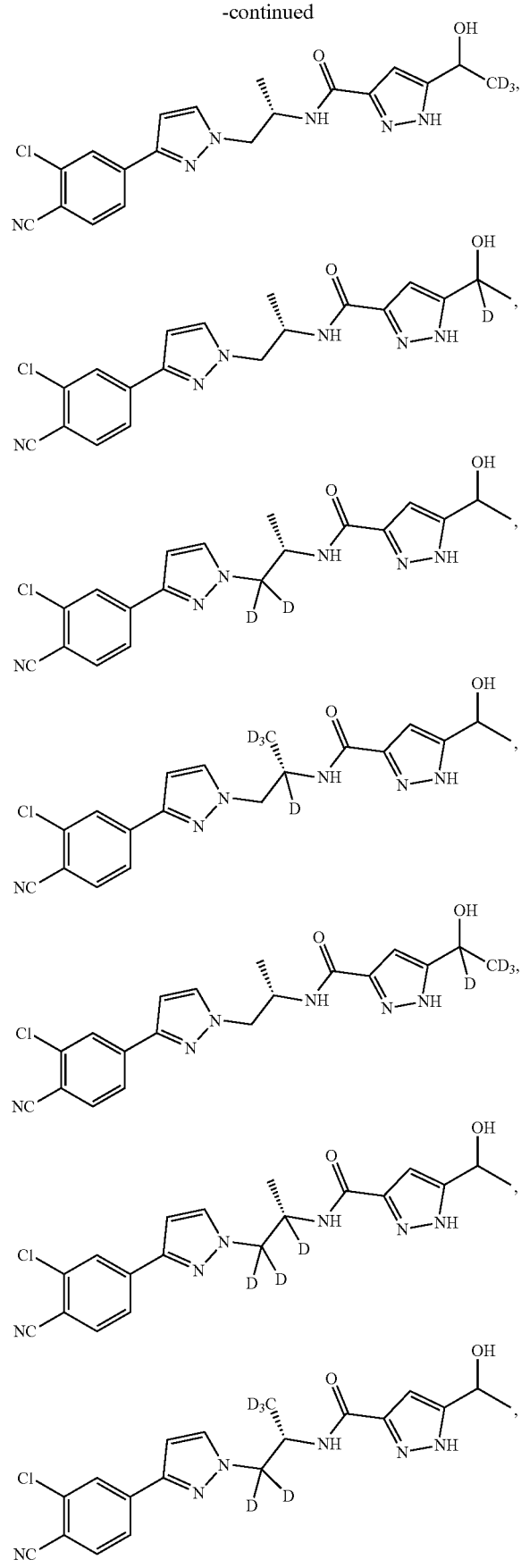
66
-continued
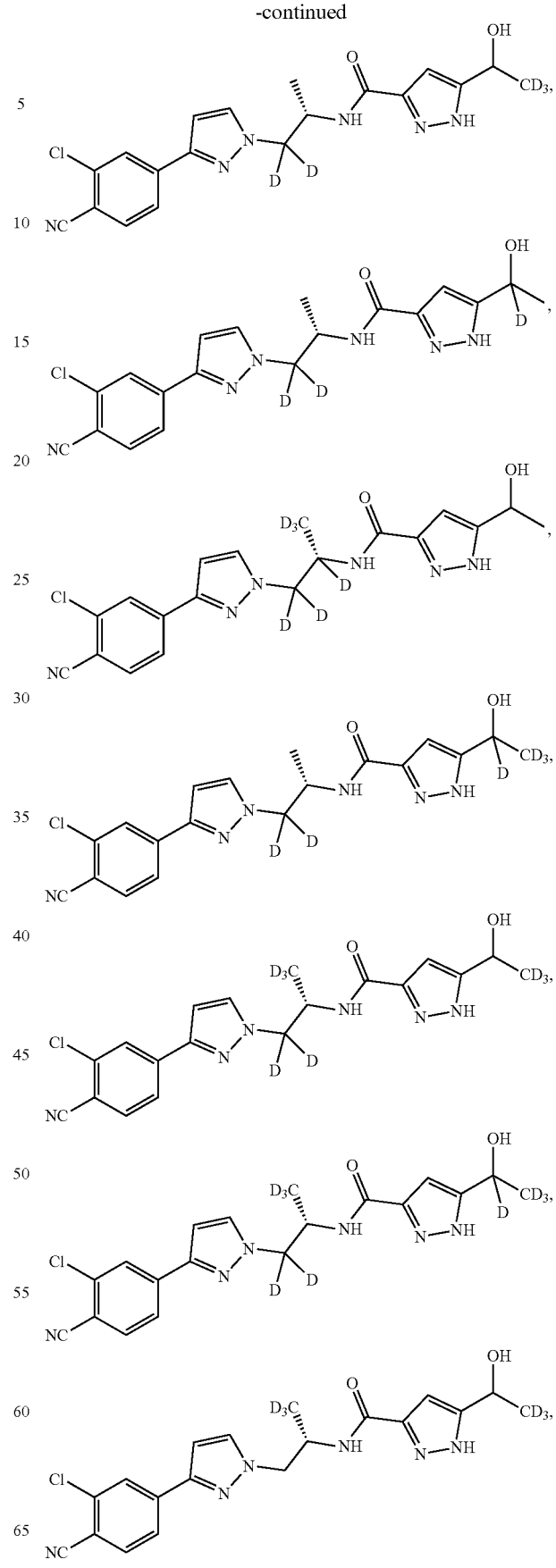

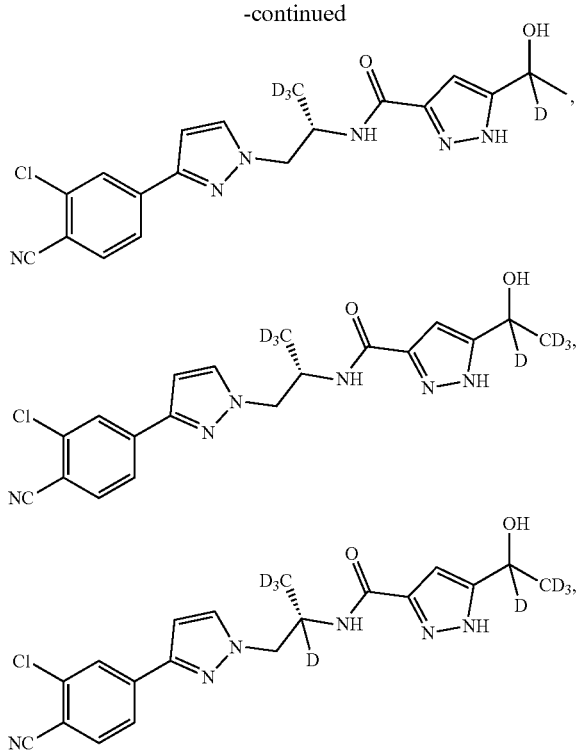
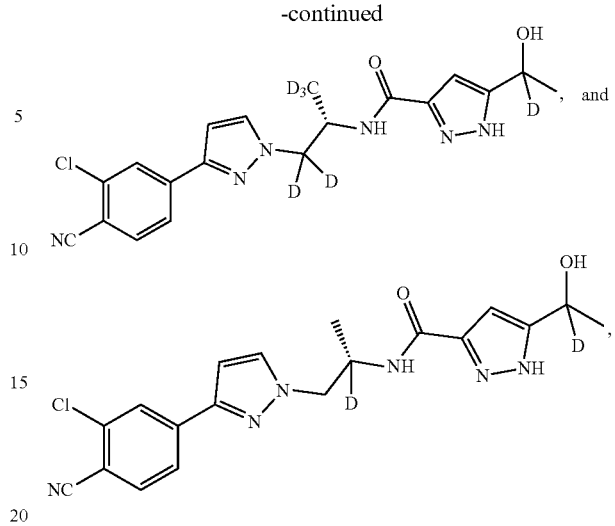
or a tautomer, stereoisomer, prodrug, crystal form, pharmaceutically acceptable salt, hydrate or solvate thereof.
10. A pharmaceutical composition, comprising a pharmaceutically acceptable excipient and the compound according to claim 1, or a tautomer, stereoisomer, prodrug, crystal form, pharmaceutically acceptable salt, hydrate or solvate thereof.
* * * * *